(12) United States Patent
Pedersen et al.

(10) Patent No.: US 7,413,854 B2
(45) Date of Patent: Aug. 19, 2008

(54) METHOD FOR SYNTHESISING TEMPLATED MOLECULES

(75) Inventors: Henrik Pedersen, Bagsvaerd (DK);
Anette Holtmann, Ballerup (DK);
Thomas Franch, Copenhagen N. (DK);
Alex Haahr Gouliaev, Veksoe Sjaelland (DK); Jakob Felding, Charlottenlund (DK)

(73) Assignee: Nuevolution A/S, Copenhagen (DK)

( * ) Notice: Subject to any disclaimer, the term of this patent is extended or adjusted under 35 U.S.C. 154(b) by 237 days.

(21) Appl. No.: 10/507,121

(22) PCT Filed: Mar. 14, 2003

(86) PCT No.: PCT/DK03/00172

§ 371 (c)(1),
(2), (4) Date: Mar. 17, 2005

(87) PCT Pub. No.: WO03/078625

PCT Pub. Date: Sep. 25, 2003

(65) Prior Publication Data

US 2005/0221316 A1    Oct. 6, 2005

Related U.S. Application Data

(60) Provisional application No. 60/409,968, filed on Sep. 12, 2002, provisional application No. 60/389,885, filed on Jun. 20, 2002, provisional application No. 60/364,056, filed on Mar. 15, 2002.

(30) Foreign Application Priority Data

| Mar. 15, 2002 | (DK) | PA 2002 00415 |
| Jun. 20, 2002 | (DK) | PA 2002 00952 |
| Jun. 20, 2002 | (WO) | PCT/DK02/00419 |
| Sep. 12, 2002 | (DK) | PA 2002 01347 |

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search .............. 435/6; 536/22.1, 25.3
See application file for complete search history.

(56) References Cited

U.S. PATENT DOCUMENTS 4,822,731 A    4/1989    Watson et al.
(Continued)

FOREIGN PATENT DOCUMENTS

DE    19642751    4/1998
(Continued)

OTHER PUBLICATIONS

Doyon, J.B et al. "Highly sensitive in vitro selections for DNA-linked synthetic small molecules with protein binding affinity and specificity" *J. Am. Chem. Soc*, Sep. 16, 2003, pp. 1-2 and S1-S8.
(Continued)

*Primary Examiner*—Ethan Whisenant
(74) *Attorney, Agent, or Firm*—Iver P. Cooper

(57) ABSTRACT

The invention relates to a method for synthesizing templated molecules attached to the templated which directed the synthesis thereof. The method involves a template, a scaffold functional entity and a functional entity attached to a building block, which, in turn, is attached the template. The scaffold functional entity and the functional entity of the building block are both provided with complementary dimerization domains allowing the functional entities to come into close proximity when the complementary domains interact with to each other. The method may be used for generating libraries of templated molecules which may be selected for biological activity.

145 Claims, 21 Drawing Sheets

U.S. PATENT DOCUMENTS

| | | | |
|---|---|---|---|
| 5,047,519 A | 9/1991 | Hobbs, Jr. et al. | |
| 5,451,503 A * | 9/1995 | Hogan et al. | 435/6 |
| 5,476,930 A | 12/1995 | Letsinger et al. | |
| 5,503,805 A | 4/1996 | Sugarman et al. | |
| 5,571,903 A | 11/1996 | Gryaznov et al. | |
| 5,573,905 A | 11/1996 | Lerner et al. | |
| 5,639,603 A | 6/1997 | Dower et al. | |
| 5,665,975 A | 9/1997 | Kedar et al. | |
| 5,681,943 A | 10/1997 | Letsinger et al. | |
| 5,708,153 A | 1/1998 | Dower et al. | |
| 5,723,598 A | 3/1998 | Lerner et al. | |
| 5,741,643 A | 4/1998 | Gryaznov et al. | |
| 5,763,263 A | 6/1998 | Dehlinger | |
| 5,770,358 A | 6/1998 | Dower et al. | |
| 5,780,613 A | 7/1998 | Letsinger et al. | |
| 5,789,162 A | 8/1998 | Dower et al. | |
| 5,830,658 A | 11/1998 | Gryaznov et al. | |
| 5,843,650 A | 12/1998 | Segev | |
| 5,948,648 A | 9/1999 | Khan et al. | |
| 6,056,926 A | 5/2000 | Sugarman et al. | |
| 6,060,596 A | 5/2000 | Lerner et al. | |
| 6,096,875 A | 8/2000 | Khan et al. | |
| 6,140,493 A | 10/2000 | Dower et al. | |
| 6,143,497 A | 11/2000 | Dower et al. | |
| 6,143,503 A | 11/2000 | Baskerville et al. | |
| 6,165,717 A | 12/2000 | Dower et al. | |
| 6,165,778 A | 12/2000 | Kedar et al. | |
| 6,197,555 B1 | 3/2001 | Khan et al. | |
| 6,207,446 B1 | 3/2001 | Szostak et al. | |
| 6,235,889 B1 * | 5/2001 | Ulanovsky | 536/24.3 |
| 6,248,568 B1 | 6/2001 | Khan et al. | |
| 6,297,053 B1 | 10/2001 | Stemmer | |
| 6,416,949 B1 | 7/2002 | Dower et al. | |
| 6,429,300 B1 | 8/2002 | Kurz et al. | |
| 6,593,088 B1 | 7/2003 | Saito et al. | |
| 6,620,587 B1 | 9/2003 | Taussig et al. | |
| 7,070,928 B2 * | 7/2006 | Liu et al. | 435/6 |
| 2003/0004122 A1 | 1/2003 | Beigelman et al. | |
| 2005/0025766 A1 | 2/2005 | Liu et al. | |
| 2005/0042669 A1 | 2/2005 | Liu et al. | |

FOREIGN PATENT DOCUMENTS

| | | |
|---|---|---|
| EP | 0324616 | 7/1989 |
| EP | 0604552 | 4/1993 |
| EP | 0643778 | 10/1993 |
| EP | 0604552 | 7/1994 |
| EP | 0695305 | 10/1994 |
| EP | 0776330 | 10/1996 |
| EP | 0773227 | 5/1997 |
| EP | 0776330 | 6/1997 |
| EP | 1533385 | 5/2005 |
| WO | 9005785 | 5/1990 |
| WO | 9303172 | 2/1991 |
| WO | 9105058 | 4/1991 |
| WO | WO 93/06121 A1 | 4/1993 |
| WO | 9512608 | 5/1995 |
| WO | 9609316 | 3/1996 |
| WO | 9612014 | 4/1996 |
| WO | 9635699 | 11/1996 |
| WO | 9735198 | 9/1997 |
| WO | 9831700 | 7/1998 |
| WO | WO9856904 A | 12/1998 |
| WO | 0021909 | 4/2000 |
| WO | 0023458 | 4/2000 |
| WO | WO 00/23458 A1 | 4/2000 |
| WO | 0032823 | 6/2000 |
| WO | 0047775 | 8/2000 |
| WO | WO 00/61775 A1 | 10/2000 |
| WO | WO 0061775 A | 10/2000 |
| WO | 0100876 | 1/2001 |
| WO | WO 02/074929 A2 | 9/2002 |
| WO | WO 02074929 A | 9/2002 |
| WO | 02102820 | 12/2002 |
| WO | 02103008 | 12/2002 |
| WO | 03078050 | 9/2003 |
| WO | 03078445 | 9/2003 |
| WO | 03078446 | 9/2003 |
| WO | 03078625 | 9/2003 |
| WO | 03078626 | 9/2003 |
| WO | 03078627 | 9/2003 |
| WO | 03082901 | 10/2003 |
| WO | 04001042 | 12/2003 |
| WO | 2004009814 | 1/2004 |
| WO | 2004013070 | 2/2004 |
| WO | 2004016767 | 2/2004 |
| WO | 2004024929 | 3/2004 |
| WO | 2004039825 | 5/2004 |
| WO | 2005003778 | 5/2004 |
| WO | 2004056994 | 7/2004 |
| WO | 2004074429 | 9/2004 |
| WO | 2004074501 | 9/2004 |
| WO | 2004083427 | 9/2004 |
| WO | 2004099441 | 11/2004 |
| WO | 2004110964 | 12/2004 |
| WO | 2005003778 | 1/2005 |
| WO | 2005026387 | 3/2005 |

OTHER PUBLICATIONS

Kanan, M.W et al. "Reaction discovery enabled by DNA-templated synthesis and in vitro selection" *Nature*, vol. 431, Sep. 30, 2004, pp. 545-549.

"Finding reactions in a haystack: Try'em all, see what works" *Meeting American Chemical Society*, Sep. 10, 2004, vol. 305, Science.

Nemoto, N et al. "In vitro virus: bonding of mRNA bearing puromycin at the 3'-terminal end to the C-terminal end of its encoded protein on the ribosome in vitro". FEBS Lett. Sep. 8, 1997;414(2):405-8.

Roberts, RW et al. "RNA-peptide fusions for the in vitro selection of peptides and proteins". Proc Natl Acad Sci U S A. Nov. 11, 1997;94(23):12297-302.

Kurz, M et al. "An efficient synthetic strategy for the preparation of nucleic acid-encoded peptide and protein libraries for in vitro evolution protocols" Fourth International Electronic Conference on Synthetic Organic Chemistry (ECSOC-4), www.mdpi.org/ecsoc-4.htm, Sep. 1-30, 2000.

Kurz, M et al. Psoralen photo-crosslinked mRNA-puromycin conjugates: a novel template for the rapid and facile preparation of mRNA-protein fusions. Nucleic Acids Res. Sep. 15, 2000;28(18):E83.

Keiler et al. "Role of a peptide tagging system in degradation of proteins synthesized from damaged messenger RNA". Science. Feb. 16, 1996;271(5251):990-3.

Benner, SA. "Expanding the genetic lexicon: incorporating non-standard amino acids into proteins by ribosome-based synthesis". Trends Biotechnol. May 1994;12(5):158-63.

Mendel, D. "Site-directed mutagenesis with an expanded genetic code". Annu. Rev. Biophys. Biomol. Struc. 1995. 24:463-93.

Liu DR et al. "Engineering a tRNA and aminoacyl-tRNA synthetase for the site-specific incorporation of unnatural amino acids into proteins in vivo". Proc Natl Acad Sci U S A. Sep. 16, 1997;94(19):10092-7.

Liu DR et al. "Progress toward the evolution of an organism with an expanded genetic code". Proc Natl Acad Sci USA. Apr. 27, 1999;96(9):4780-5.

Liu, R et al. "Optimized synthesis of RNA-protein fusions for in vitro protein selection". Methods Enzymol. 2000;318:268-93.

Wang, L et al. "A new functional suppressor tRNA/aminoacyl-tRNA synthetase pair for the in vivo incorporation of unnatural amino acids into proteins" J. Am. Chem. Soc 2000, 122, 5010-5011 Pub Apr. 5, 2000.

Ellman J.A., et al. "Biosynthetic method for introducing Unnatural Amino acids site specifically into proteins", Methods Enzymol. 202, 301-336 (1992).

José Salas et al. "Biosynthetic Polydeoxynucleotides as Direct Templates for Polypeptide Synthesis". J. of Biological Chemistry, vol. 243, No. 6, 1968, p. 1012-1015.

Walder JA, Walder RY, Heller MJ, Freier SM, Letsinger RL, Klotz IM. "Complementary carrier peptide synthesis: general strategy and implications for prebiotic origin of peptide synthesis", Proc Natl Acad Sci U S A. Jan. 1979;76(1):51-5.

Bruick et al. "Template-directed ligation of peptides to oligonucleotides" Chemistry and Biology, vol. 3, No. 1, Jan. 1996, p. 49-56.

Tamura K. Schimmel P. "Oligonucleotide-directed peptide synthesis in a ribosome- and ribozyme-free system". Proc Natl Acad Sci U S A. Feb. 13, 2001;98(4):1393-7.

Lewis RJ, Hanawalt PC. "Ligation of oligonucleotides by pyrimidine dimers—a missing 'link' in the origin of life?"22;298(5872):393-6.

Liu J, Taylor JS. "Template-directed photoligation of oligodeoxyribonucleotides via 4-thiothymidine". Nucleic Acids Res. Jul. 1, 1998;26(13):3300-4.

Fujimoto et al. "Template-directed photoreversible ligation of deoxyoligonucleotides via 5-Vinyldeoxyuridine" J. Am. Soc. 2000, 122, 5646-5647.

Kenzo Fujimoto, Shigeo Matsuda, Naoki Ogawa, Masayuki Hayashi & Isao Saito "Template-directed reversible photocircularization of DNA via 5-vinyldeoxycytidine". Tetrahedron Letters 2000, 41:33:6451-6454.

Kenzo Fujimoto, Naoki Ogawa, Masayuki Hayashi, Shigeo Matsuda & Isao Saito "Template directed photochemical synthesis of branched oligodeoxynucleotides via 5-carboxyvinyldeoxyuridine". Tetrahedron letters 2000, 41:49:9437-40.

Letsinger et al. "Chemical Ligation of oligonucleotides in the presence and absence of a template". J. Amer. Chem. Soc. 1993, 115, 3808-9.

Gryaznov SM, Letsinger RL. "Template controlled coupling and recombination of oligonucleotides blocks containing thiophosphoryl groups". Nucleic Acids Res. Mar. 25, 1993;21(6):1403-8.

Gryaznov SM, Schultz R, Chaturvedi SK, Letsinger RL. "Enhancement of selectivity in recognition of nucleic acids via chemical autoligation". Nucleic Acids Res. Jun. 25, 1994;22(12):2366-9.

Herrlein MK, Letsinger RL. "Selective chemical autoligation on a double-stranded DNA template". Nucleic Acids Res. Nov. 25, 1994;22(3):5076-8.

Letsinger, RL; Wu, T; Elghanian, R "Chemical and photochemical ligation of oligonucleotide blocks". Nucleosides and nucleotides, 16(5&6), 643-652 (1997).

Visscher J, Bakker CG, van der Woerd R, Schwartz AW "Template-directed oligomerization catalyzed by a polynucleotide analog". Science. Apr. 21, 1989;244(4902):329-31.

Visscher J, van der Woerd R, Bakker CG, Schwartz AW. "Oligomerization of deoxynucleoside-bisphosphate dimers: template and linkage specificity". Orig Life Evol Biosph. 1989;19(1):3-6.

Zhan, ZJ and Lynn, DG "Chemical Amplification through template-directed synthesis". J. Am. Soc. 1997, 119, 12420-1.

Bruick RK, Koppitz M, Joyce GF, Orgel LE. "A simple procedure for constructing 5'-amino-terminated oligodeoxynucleotides in aqueous solution Nucleic Acids Res". Mar. 15, 1997;25(6):1309-10.

Albagli, D; Atta, RVA; Cheng, P; Huan, B and Wood, ML. "Chemical amplification (CHAMP) by a continuous, self-replicating oligonucleotide-based system" J. Am. Chem. Soc. 1999, 121, 6954-6955. Pub. on the web Jul. 14, 1999.

Xu, Y and Kool, E "Rapid and Selective selenium-mediated autoligation of DNA strands" J. Am. Chem. Soc. 2000, 122, 9040-1 Pub. on web Aug. 31, 2000.

Xu Y, Karalkar NB, Kool ET. "Nonenzymatic autoligation in direct three-color detection of RNA and DNA point mutations". Nat Biotechnol. Feb. 2001;19(2):148-52.

Li X, Zhan ZY, Knipe R, Lynn DG. "DNA-catalyzed polymerization". J Am Chem Soc. Feb. 6, 2002;124(5):746-7.

Czlapinski, JL and Sheppard, TL. "Nucleic acid template-directed assembly of metallosalen-DNA conjugates". J Am Chem Soc. Sep. 5, 2001;123(35):8618-9 published on the web Aug. 10, 2001.

Leitzel JC, Lynn DG "Template-directed ligation: from DNA towards different versatile templates". Chem Rec. 2001;1(1):53-62. Published online Jan. 30, 2001.

Schmidt JG, Nielsen PE, Orgel LE. "Information transfer from peptide nucleic acids to RNA by template-directed syntheses". Nucleic Acids Res. Dec. 1, 1997;25(23):4792-4796.

Dower, WJ et al. "In vitro selection as a powerful tool for the applied evolution of proteins and peptides".Current Opinion in Chemical Biology, 2002, 6:390-398.

David Liu. "Expanding the reaction scope of DNA-templated synthesis Angew". Chem. Int. Ed. 2002, 41, No. 10 pp. 1796-1800. Published May 15, 2002.

Gartner, ZJ et al. "Multistep small-molecule synthesis programmed by DNA templates". J. Am. Chem. Soc. vol. 124, No. 35, 2002, 10304-10306.

Calderone, CT et al. "Directing otherwise incompatible reactions in a single solution by using DNA-templated organic synthesis". Angew Chem Int Ed, 2002, 41, No. 21. 4104-4108.

Bittker, JA; Phillips, KJ and Liu, DR "Recent advances in the in vitro evolution of nucleic acids". Curr Opin Chem Biol. Jun. 2002;6(3):367-74. Review. Pub. on the web Mar. 20, 2002.

Gartner, ZJ et al. "Two enabling architectures for DNA-templated organic synthesis". Angew. Chem. Int. Ed. 2003, 42, No. 12, 1370-1375.

Rosenbaum, DM et al. "Efficient and sequence-specific DNA-templated polymerization of peptide nucleic acid aldehydes". J. Am. Chem. Soc. vol. 125, No. 46, 2003, 13924-13925.

Li, X et al. "Stereoselectivity in DNA-templated organic synthesis and its orgins". J. Am. Chem. Soc. vol. 125, No. 34, 2003, 10188-10189.

Gordon, EM et al. "Applications of combinatorial technologies to drug discovery. 2. Combinatorial organic synthesis, library screening strategies, and future directions". Journal of Medicinal Chemistry, vol. 37, No. 10, May 13, 1994.

Otto, S et al. S"Recent developments in dynamic combinatorial chemistry". Current opinion in Chemical Biology 2002, 6: 321-327.

Pavia, MR. "The Chemical generation of molecular diversity". http://www.netsci.org/Science/Combichem/feature01.html.

Braun, E, et al. "DNA-templated assembly and electrode attachment of a conducting silver wire". Nature, vol. 391, Feb. 19, 1998, 775-778.

Tanaka, K et al. "Synthesis of a novel nucleoside for alternative DNA base pairing through metal complexation" J. Org. Chem. 1999, 64, 5002-5003.

Berger, M et al. "Universal bases for hybridization, replication and chain termination", Nucleic acids research, Oxford University Press, vol. 28, No. 15, pub. Aug. 1, 2000, p. 2911-2914.

Weizman, H et al. "2,2'-Bipyridine ligandoside: a novel building block for modifying DNA with intra-duplex metal complexes". J. Am. Chem. Soc. 2001, 123, 3375-3376.

Frutos, AG et al. "Demonstration of a word design strategy for DNA computing on surfaces". Nucleic Acids Research, 1997, vol. 25, No. 23, 4748-4757.

Loweth, CJ et al. "DNA-based assembly of gold nanocrystals". Angew. Chem. Int. Ed. 1999, 38, No. 12. 1808-1812.

Elghanian, R et al. "Selective colorimetric detection of polynucleotides based on the distance-dependent optical properties of gold nanoparticles". Science, vol. 277, Aug. 22, 1997.

Storhoff, JJ and Mirkin, CA. "Programmed Materials Synthesis with DNA". Chem Rev. Jul. 14, 1999;99(7):1849-1862.

Mirkin CA. "Programming the assembly of two- and three-dimensional architectures with DNA and nanoscale inorganic building blocks". Inorg Chem. May 29, 2000;39(11):2258-72.

Waybright SM, Singleton CP, Wachter K, Murphy CJ, Bunz UH. "Oligonucleotide-directed assembly of materials: defined oligomers". J Am Chem Soc. Mar. 7, 2001;123(9):1828-33. Pub. on web Feb. 7, 2001.

Bruce Smith and Markus Krummenacker "DNA-guided assembly of proteins as a pathway to an assembler" http://www.wadsworth.org/albcon97/abstract/krummena.htm) The 1997 Albany Conference: Biomolecular Motors and Nanomachines.

DeWitt, SH et al. "Diversomers": an approach to nonpeptide, nonoligomeric chemical diversity. Proc. Natl. Acad. Sci, USA, vol. 90, pp. 6909-6913, Aug. 1993.

Nielsen, J et al. "Synthetic methods for the implementation of encoded combinatorial chemistry". J. Am. Chem. Soc. 1993, 115, 9812-9813.

Ohlmeyer, MHJ et al. "Complex synthetic chemical libraries indexed with molecular tags". Proc. Natl. Acad, Sci, USA, vol. 90, pp. 10922-10926, Dec. 1993, Chemistry.

Zuckermann, RN et al. "Discovery of nanomolar ligands for 7-transmembrane G-protein-coupled receptors from a diverse N-(substituted) glycine peptoid library". J. Med. Chem. 1994, 37, 2678-2685.

Luo, P et al. "Analysis of the structure and stability of a backbone-modified oligonucleotide: implications for avoiding product inhibition in catalytic template-directed synthesis". J. Am. Chem. Soc. 1998, 120, 3019-3031.

Luther, A et al. "Surface-promoted replication and exponential amplification of DNA analogues". Nature, vol. 396, Nov. 19, 1998, 245-248.

Klekota, B et al. "Selection of DNA-Binding Compounds via Multistage Molecular Evolution". Tetrahedron 55 (1999) 11687-11697.

Furlan, RLE et al. "Molecular amplification in a dynamic combinatorial library using non-covalent interactions". Chem. Commun., 2000, 1761-1762.

Ramström, O et al. "In situ generation and screening of a dynamic combinatorial carbohydrate library against concanavalin A". ChemBioChem, 2000, 1, 41-48.

Cousins, GRL et al. "Identification and Isolation of a Receptor for N-Methyl Alkylammonium Salts: Molecular Amplification in a Pseudo-peptide Dynamic Combinatorial Library". Angew. Chem. Int. Ed., 2001, 40, No. 2, 423-427.

Roberts, SI et al. "Simultaneous selection, amplification and isolation of a pseudo-peptide receptor by an immobillsed N-methyl ammonium ion template". Chem. Commun., 2002, 938-939.

"The Nucleus", Jan. 2004, vol. LXXXII, No. 5, R. Grubina; "Summer Research Report; R. Grubina on DNA Templated Synthesis for Small Molecule Library", p. 10-14.

Nazarenko et al., "A closed tube format for amplification and detection of DNA based on energy transfer", Nucleic Acids Research, 1997, vol. 25, No. 12, p. 2516-2521.

Chan et al., "Intra-tRNA distance measurements for nucleocapsid protein-dependent tRNA unwinding during priming of HIV reverse transcription", PNAS vol. 96, p. 459-464, Jan. 1999.

DNA-templated synthesis as a basis for the evolution of synthetic molecules. Liu DR, Gartner ZJ, Kanan MW, Calderone CT Abstracts of Papers of the American Chemical Society 225: 612-ORGN, Part 2, Mar. 2003.

Rodriguez et al., "Template-directed extension of a guanosine 5'-phosphate covalently attached to an oligodeoxycytidylate template", J Mol Evol (1991) 33:477-482.

Inoue et al, Oligomerization of (Guanosine 5'-phosphor)-2-methylimidazolide on Poly(C), J. Mol. Biol. (1982), 162, 201-217.

C. B. Chen et al., "Template-directed synthesis on Oligodeoxycytidylate and Polydeoxycytidylate templates" J. Mol. Biol. 1985, 181, 271.

H. Rembold et al., "Single-strand regions of Poly(G) act as templates for oligo(C) synthesis" J. Mol. Evol. 1994, 38, 205.

T. Inoue et al., "A nonenzymatic RNA polymerase model", Science 1983, 219, p. 859-862.

O. L. Acevedo et al., "Non-enzymatic transcription of an oligonucleotide 14 residues long", J. Mol. Biol. 1987, 197, p. 187-193.

C. Böhler et al., "Template switching between PNA and RNA oligonucleotides", Nature 1995, 376, 578-581.

Acevedo et al., "Template-directed oligonucleotide ligation on hydroxylapatite", Nature vol. 321, Jun. 19, 1986, p. 790-792.

Piccirilli, "RNA seeks its maker", Nature vol. 376, Aug. 17, 1995, p. 548-.

A. W. Schwartz et al., "Template-directed synthesis of novel, nucleic acid-like structures", Science 1985, 228, 585-7.

Halpin et al.: DNA display III. Solid-phase organic synthesis on unprotected DNA. PLoS Biol. Jul. 2004;2(7):E175. Epub Jun. 22, 2004.

Halpin et al.: DNA display II. Genetic manipulation of combinatorial chemistry libraries for small-molecule evolution. PLoS Biol. Jul. 2004;2(7):E174. Epub Jun. 22, 2004.

Halpin et al.: DNA diaplay I. Sequence-encoded routing of DNA populations. PLoS Biol. Jul. 2004;2(7):E173. Epub Jun. 22, 2004.

"Highly Sensitive In Vitro Selections for DNA-Linked Synthetic Small Molecules with Protein Binding Affinity and Specificity" Doyon, J. B.; Synder, T. M.; Liu, D. R. J. Am. Chem. Soc. 125, 12372-12373 (2003).

"Translation of DNA into Synthetic N-Acyloxazolidines" Li, X.; Gartner, Z. J.; Tse, B. N.; Liu, D. R. J. Am. Chem. Soc. 126, 5090-5092 (2004).

"DNA-Templated Organic Synthesis: Nature's Strategy for Controlling Chemical Reactivity Applied to Synthetic Molecules" Li, X.; Liu, D. R. Angew. Chem. Int. Ed. 43, 4848-4870 (2004).

"DNA-Templated Organic Synthesis and Selection of a Library of Macrocycles" Gartner, Z. J.; Tse, B. N.; Grubina, R.; Doyon, J. B.; Snyder, T. M.; Liu, D. R. Science 305, 1601-1605 (2004).

"Nucleic Acid-Templated Synthesis as a Model System for Ancient Translation" Calderone, C. T. and Liu, D. R. Curr. Opin. Chem. Biol. 8, 645-653 (2004).

"DNA-Templated Functional Group Transformations Enable Sequence-Programmed Synthesis Using Small-Molecule Reagents" Sakurai, K.; Snyder, T. M.; Liu, D. R. J. Am. Chem. Soc. 127, 1660-1661 (2005).

"Translating DNA into synthetic Molecules", David R. Liu, PLoS Biology, Jul. 2004, vol. 2, Iss. 7, p. 905-6.

"The Development of Amplifiable and Evolvable Unnatural Molecules", David R. Liu, Harvard Univ. Cambridge MA Dept of Chemistry and Chemical Biology, Report dated Aug. 4, 2003 No. A104614, approved for public release.

Website of Prof. David R. Liu, publicly available Mar. 11, 2000.

Website of Prof. David R. Liu, publicly available Oct. 15, 2000.

Website of Prof. David R. Liu, publicly available Mar. 1, 2001.

Website of Prof. David R. Liu, publicly available Apr. 19, 2001.

Website of Prof. David R. Liu, publicly available Sep. 23, 2001.

Website of Prof. David R. Liu, publicly available Sep. 24, 2002.

Website of Prof. David R. Liu, publicly available Nov. 20, 2002.

Website of Prof. David R. Liu, publicly available Oct. 15, 2003.

Summerer D. et al., "DNA-templated synthesis: more versatile than expected.", Angewandte Chemie, (Jan. 4, 2002), vol. 41, No. 1, pp. 89-90.

Gartner Z. J. et al. "The generality of DNA-templated synthesis as a basis for evolving non-natural small molecules." Journal of the American Society, (Jul. 18, 2001), vol. 123, No. 28, pp. 6961-6963.

Matsuura K. et al. "Construction of glyco-clusters by self-organization of site-specifically glycosylated oligonucleotides and their cooperative amplification of lectin-recognition.", Journal of the American Chemical Society, (Jan. 17, 2001, vol. 123, No. 2, pp. 357-358.

Brenner S. et al., "Encoded combinatorial chemistry", Proceedings of the National Academy of Sciences of USA, National Academy of Science, (Jun. 1, 1992), vol. 89, No. 12, pp. 5381-5383.

Visscher J. et al., "Template-directed synthesis of acyclic oligonucleotide analogues", Journal of Molecular Evolution. (1998), vol. 28, no. ½. pp. 3-6.

Brenner, Sydney and Richard A. Lerner. "Encoded Combinatorial Chemistry," *Proc. Natl. Acad. Sci. USA*, vol. 89, pp. 5381-5383, Jun. 1992.

Bruick, Richard K. et al. "Template-Directed Ligation of Peptides to Oligonucleotides," *Chemistry and Biology* 1996, vol. 3 No. 1.

Visscher, J. and Alan W. Scwartz. "Template-Directed Synthesis of Acyclic Oligonucleotide Analogues," *J Mol Evol* (1988) 28:3-6.

Walder, Joseph A. et al. "Complementary carrier Peptide Synthesis: General Strategy and Implications for Prebiotic Origin of Peptide Synthesis," Department of Chemistry, and Department of Biochemistry and Molecular Biology, Northwestern University, Evanston, Illinois 60201.

Walder JA, Walder RY, Heller MJ, Freier SM, Letsinger RL, Klotz IM., Complementary carrier peptide synthesis: general strategy and implications for prebiotic origin of peptide synthesis., Proc Natl Acad Sci U S A. Jan. 1979; 76(1):51-5.

Tamura K, Schimmel P., Oligonucleotide-directed peptide synthesis in a ribosome- and ribozyme-free system., Proc Natl Acad Sci U S A. Feb. 13, 2001;98(4):1393-7.

Lewis RJ, Hanawalt PC., Ligation of oligonucleotides by pyrimidine dimers—a missing 'link' in the origin of life?, Nature. Jul. 22, 1982; 298(5872):393-6.

Royer, GP; Cruickshank, KA; Morrison, LE., Template-directed photoligation, EP 0324616 B1 Filed: Jan. 12, 1989 Priority: Jan. 13, 1988 Publication date: Jul. 19, 1989.

Liu J, Taylor JS., Template-directed photoligation of oligodeoxyribonucleotides via 4-thiothymidine., Nucleic Acids Res. Jul. 1, 1998; 26(13):3300-4.

Fujimoto et al., Template-directed photoreversible ligation of deoxyoligonucleotides via 5-Vinyldeoxyuridine, J. Am. Chem. Soc. 2000, 122, 5646-5647.

Kenzo Fujimoto, Shigeo Matsuda, Naoki Ogawa, Masayuki Hayashi & Isao Saito, Template-directed reversible photocircularization of DNA via 5-vinyldeoxycytidine, Tetrahedron Letters 2000, 41:33:6451-6454.

Kenzo Fujimoto, Naoki Ogawa, Masayuki Hayashi, Shigeo Matsuda & Isao Saito, Template directed photochemical synthesis of branced oligodeoxynucleotides via 5-carboxyvinyldeoxyuridine, Tetrahedron letters 2000, 41:49:9437-40.

Gryaznov et al., Chemical Ligation of oligonucleotides in the presence and absence of a template, J. Amer. Chem. Soc. 1993, 115, 3808-9.

Gryaznov SM, Letsinger RL., Template controlled coupling and recombination of oligonucleotide blocks containing thiophosphoryl groups., Nucleic Acids Res. Mar. 25, 1993; 21(6):1403-8.

Gryaznov SM, Schultz R, Chaturvedi SK, Letsinger RL., Enhancement of selectivity in recognition of nucleic acids via chemical autoligation., Nucleic Acids Res. Jun. 25, 1994; 22(12):2366-9.

Herrlein MK, Letsinger RL., Selective chemical autoligation on a double-stranded DNA template, Nucleic Acids Res. Nov. 25, 1994; 22(23):5076-8.

Letsinger, RL; Wu, T; Elghanian, R, Chemical and photochemical ligation of oligonucleotide blocks, Nucleosides and nucleotides, 16(5&6), 643-652 (1997).

Letsinger, RL; Gryaznov, SM, Chemical ligation of template-directed oligonucleotides, EP0830363A1/WO 96/35699, Published: Nov. 14, 1996 Filed: May 3, 1996 Priority date: May 8, 1995.

Letsinger, RL; Gryaznov, SM, Method of forming oligonucleotides, EP 0695305 Published Oct. 27, 1994 Priority: Apr. 12, 1993 Filed Apr. 6, 1994.

Visscher J, Bakker CG, van der Woerd R, Schwartz AW, Template-directed oligomerization catalyzed by a polynucleotide analog., Science. Apr. 21, 1989; 244(4902):329-31.

Visscher J, van der Woerd R, Bakker CG, Schwartz AW., Oligomerization of deoxynucleoside-bisphosphate dimers: template and linkage specificity., Orig Life Evol Biosph. 1989;19(1):3-6.

Zhan, ZJ and Lynn, DG, Chemical Amplification through template-directed synthesis, J. Am. Chem. Soc. 1997, 119, 12420-1.

Bruick RK, Koppitz M, Joyce GF, Orgel LE., A simple procedure for constructing 5'-amino-terminated oligodeoxynucleotides in aqueous solution, Nucleic Acids Res. Mar. 15, 1997;25(6):1309-10.

Albagli, D; Atta, RVA; Cheng, P; Huan, B and Wood, ML., Chemical amplification (CHAMP) by a continuous, self-replicating oligonucleotide-based system, J. Am. Chem. Soc. 1999, 121, 6954-6955. Pub. on the web Jul. 14, 1999.

Xu, Y and Kool, E, Rapid and Selective selenium-mediated autoligation of DNA strands, J. Am. Chem. Soc. 2000, 122, 9040-1 Pub. on web Aug. 31, 2000.

Xu Y, Karalkar NB, Kool ET., Nonenzymatic autoligation in direct three-color detection of RNA and DNA point mutations., Nat Biotechnol. Feb. 2001; 19(2):148-52.

Li X, Zhan ZY, Knipe R, Lynn DG., DNA-catalyzed polymerization., J Am Chem Soc. Feb. 6, 2002; 124(5):746-7.

Czlapinski, JL and Sheppard, TL., Nucleic acid template-directed assembly of metallosalen-DNA conjugates., J Am Chem Soc. Sep. 5, 2001; 123(35):8618-9 published on the web Aug. 10, 2001.

Leitzel JC, Lynn DG, Template-directed ligation: from DNA towards different versatile templates., Chem Rec. 2001;1(1):53-62. Published online Jan. 30, 2001.

Schmidt JG, Nielsen PE, Orgel LE., Information transfer from peptide nucleic acids to RNA by template-directed syntheses., Nucleic Acids Res. Dec. 1, 1997; 25(23):4797-4802.

Lerner, R; Janda, K; Brenner, S; Nielsen, J, Encoded combinatorial chemical libraries, EP 0 643 778 Published: Oct. 14, 1993 Filing date: Mar. 30, 1993 Priority date: Mar. 30, 1992.

Gartner, Z; Liu, DR, The generality of DNA-templated synthesis as a basis for evolving non-natural small molecules., J Am Chem Soc. Jul. 18, 2001; 123(28):6961-3.

Gartner, et al., Expanding the reaction scope of DNA-templated synthesis, Angew. Chem. Int. Ed. 2002, 41, No. 10 pp. 1796-1800. Published May 15, 2002.

Bittker, JA; Phillips, KJ and Liu, DR, Recent advances in the in vitro evolution of nucleic acids., Curr Opin Chem Biol. Jun. 2002; 6(3):367-74. Review. Pub. on the web Mar. 20, 2002.

Summerer,D and Marx, A, DNA-templated synthesis: more versatile than expected., Angew Chem Int Ed Engl. Jan. 4, 2002; 41(1):89-90. Review.

Storhoff, JJ and Mirkin, CA., Programmed Materials Synthesis with DNA., Chem Rev. Jul. 14, 1999; 99(7):1849-1862.

Mirkin CA., Programming the assembly of two- and three-dimensional architectures with DNA and nanoscale inorganic building blocks., Inorg Chem. May 29, 2000; 39(11):2258-72.

Waybright SM, Singleton CP, Wachter K, Murphy CJ, Bunz UH., Oligonucleotide-directed assembly of materials: defined oligomers., J Am Chem Soc. Mar. 7, 2001; 123(9):1828-33. Pub. on web Feb. 7, 2001.

Bruce Smith and Markus Krummenacker, DNA-guided assembly of proteins as a pathway to an assembler, (http://www.wadsworth.org/albcon97/abstract/krummena.htm) The 1997 Albany Conference: Biomolecular Motors and Nanomachines.

Mirkin et al., Nanoparticles having oligonucleotide attached thereto and uses therefor, WO 01/00879 Filed Jun. 26, 2000 Publication date: Jan. 4, 2001.

Payan, D and Nolan, G, Combinatorial enzymatic complexes, WO 98/56904 Filed Jun. 10, 1998 Publication date: Dec. 17, 1998.

Berger, M et al., Universal bases for hybridization, replication and chain termination, Nucleic acids research, Oxford University Press, vol. 28, No. 15, pub. Aug. 1, 2000, p. 2911-2914.

Keiler, KC et al., Role of peptide tagging system in degradation of proteins synthesized from damaged messenger RNA, Science, vol. 271, Feb. 16, 1996, p. 990-993.

Salas, J et al., Biosynthetic polydeoxynucleotides as direct templates for polypeptide synthesis, Journal of Biological Chemistry, vol. 243, No. 6, 1968, p. 1012-1015.

Gold, L et al., Systematic polypeptide evolution by reverse translation, WO 93/03172 Published: Feb. 18, 1993.

Pschorr, J, Genotyp und Phanotyp koppelnde Verbindung, DE 196 46 372 Published: Jun. 19, 1997.

* cited by examiner

Fig.5
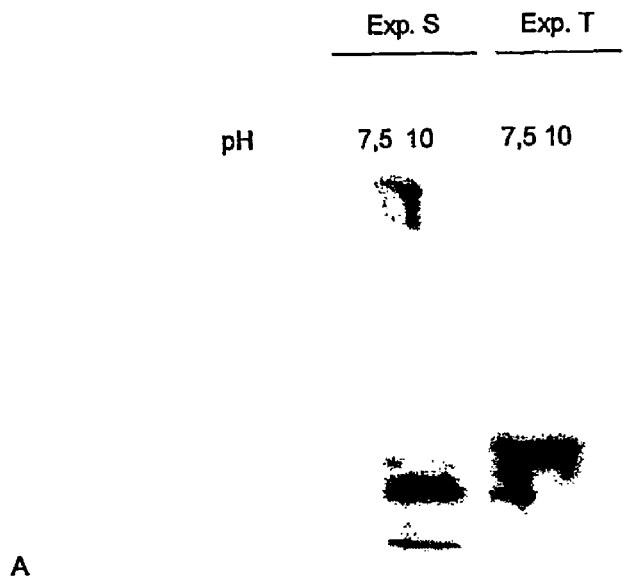
Fig. 6
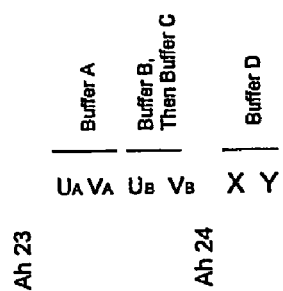
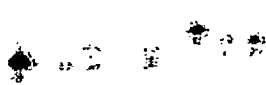

Figure 13
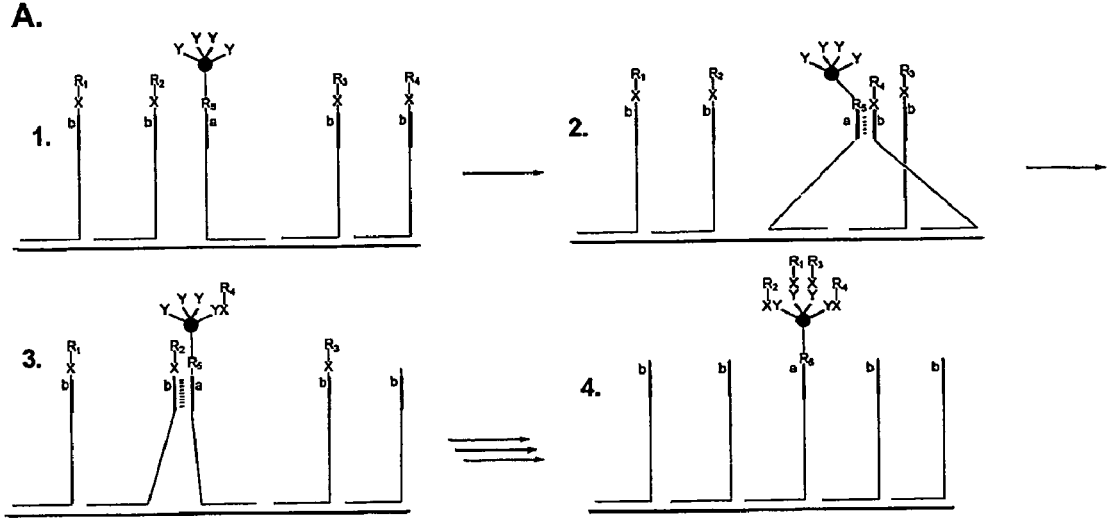
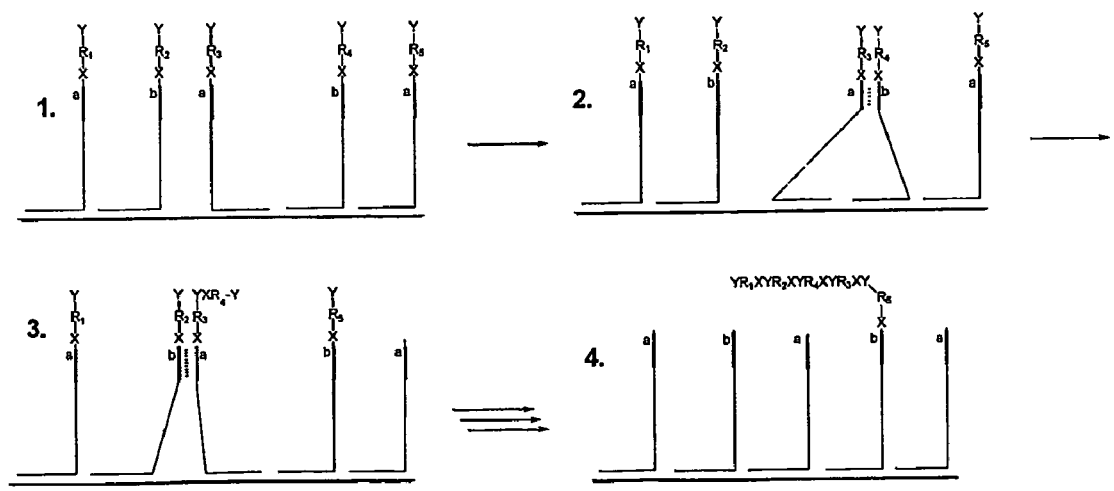

Figure 14 The Zipper box principle.

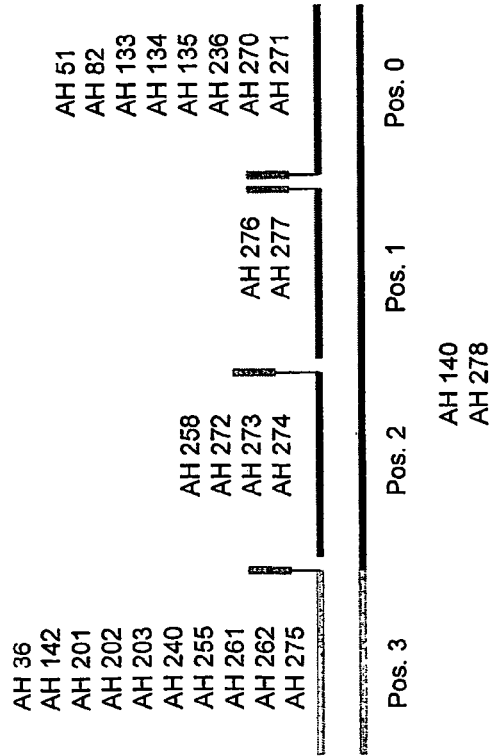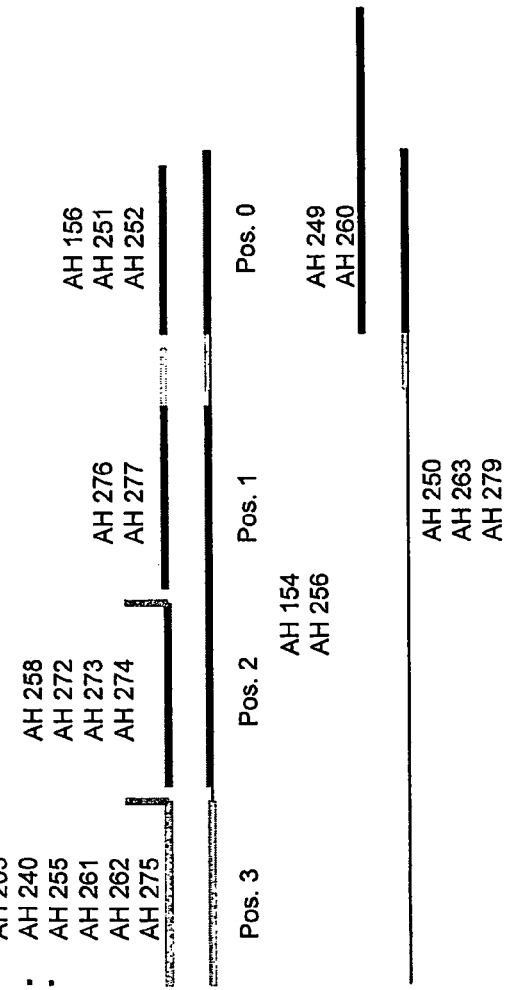
Fig. 16

Lane 1: 20,1°C
Lane 2: 25,1°C
Lane 3: 30,6°C
Lane 4: 33,4°C
Lane 5: 38,2°C
Lane 6: 40,9°C
Lane 7: 24,9°C
Lane 8: 27,9°C
Lane 9: 32,8°C
Lane 10: 38,4°C
Lane 11: 43,2°C
Lane 12: 45,9°C Lane 1: 20
Lane 2: 25
Lane 3: 30
Lane 4: 33
Lane 5: 38
Lane 6: 40

Lane 1: 24,9°C
Lane 2: 27,9°C
Lane 3: 32,8°C
Lane 4: 38,4°C
Lane 5: 43,2°C
Lane 6: 45,9°C 1: 9,9°C        7: 33°C
2: 15°C         8: 35,3°C
3: 17,6°C       9: 40,7°C
4: 23,3°C      10: 43,4°C
5: 28,3°C      11: 46,0°C
6: 31,7°C      12: 50,8°C Experiment C and D Experiment A and B 1  2  3  4  5  6  7  8  9  10 11 12
AB AB AB AB AB AB AB AB AB AB AB AB Fig. 24
1: 9,9°C        7: 33°C
2: 15°C         8: 35,3°C
3: 17,6°C       9: 40,7°C
4: 23,3°C      10: 43,4°C
5: 28,3°C      11: 46,0°C
6: 31,7°C      12: 50,8°C
Experiment G and H
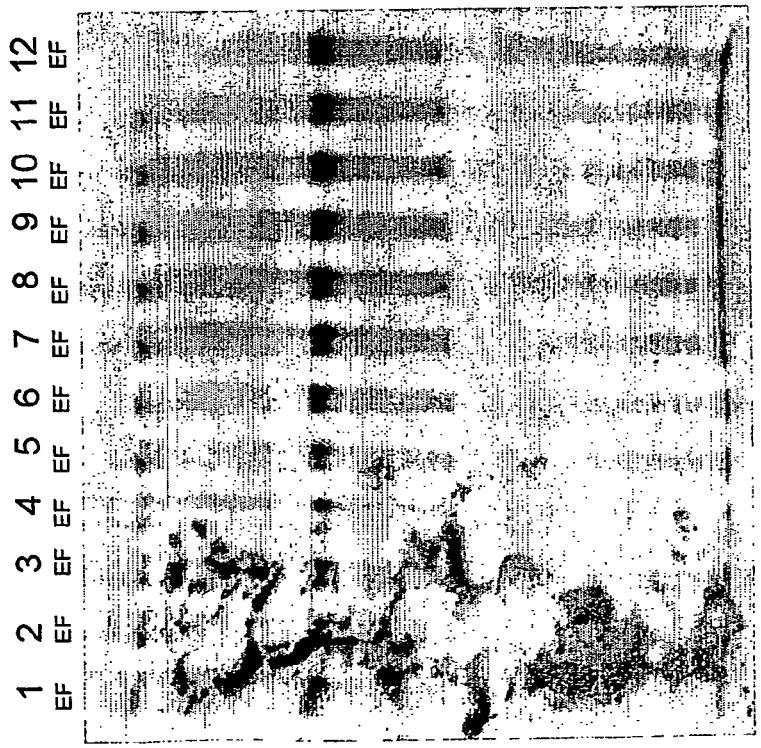
Experiment E and F

METHOD FOR SYNTHESISING TEMPLATED MOLECULES

TECHNICAL FIELD OF THE INVENTION

The present invention relates to a method for synthesising templated molecules. The method implies a high local concentration of reactive groups intended to participate in a formation of a linkage, thus increasing the probability of linkage formation. The invention also relates to a library, that is a plurality of templated molecules, wherein each of the templated molecules are attached to the template which directed the synthesis thereof.

BACKGROUND

The generation of molecules carrying new properties remains a challenging task. Recently, a number of procedures have been suggested that should allow a more efficient generation and screening of a larger number of molecules. The approaches taken involve the encoding and/or templating of molecules other than natural biopolymers such as peptide, RNA and DNA. These approaches allow the researcher to generate and screen a huge number of molecules in a short time. This should lead to better molecules carrying the desired properties.

The central dogma of biology describes the one-way flow of information from DNA to RNA to protein. Recently, methods such as phage display, peptides-on-plasmids, ribosome display and mRNA-protein fusion have been developed, allowing the transfer of information from the level of protein/peptide to RNA or DNA. This has enabled the use of molecular evolution to be applied on huge numbers of peptides that are exposed to an enrichment process, where after the enriched pool of molecules (enriched for a particular feature, such as binding to receptor protein) are amplified, by exploiting information flow from the peptide to DNA and then amplifying the DNA.

More recently, approaches have been developed that allow the encoding of polypeptides and other biochemical polymers. An example of this approach is disclosed in U.S. Pat No. 5,723,598, which pertains to the identification of a biochemical polymer that participates in a preselected binding interaction with a target to form a binding reaction complex. The prior art method encompasses the generation of a library of bi-functional molecules. One part of the bifunctional molecule is the biochemical polymer and the other part is an identifier oligonucleotide comprising a sequence of nucleotides which encodes and identifies the biochemical polymer. Following the generation of the library of the bifunctional molecules, a partitioning with respect to affinity towards the target is conducted and the identifier oligonucleotide part of the bi-functional molecule is amplified by means of PCR. Eventually, the PCR amplicons are sequenced and decoded for identification of the biochemical polymer. This approach does not, however, allow one-pot amplification of the library members. Furthermore, the sequence of nucleotides serves to identify the biochemical molecule only after a laborious sequencing process. Thus the flow of information from the identifier sequence to the biochemical polymer is restrained.

Halpin and Harbury have in WO 00/23458 suggested an improvement to the approach stipulated immediately above, wherein the molecules formed are not only identified but also directed by the nucleic acid tag. The approach is based on the traditional split-and-combine strategy for synthesis of combinatorial libraries comprising two or more synthetic steps. Plurality nucleic acid templates are used, each having at one end a chemical reactive site and dispersed throughout the stand a plurality of codons regions, each of said codon regions in turn specifying different codons. Separately, each of the strands, identified by a first codon region, is reacted at the chemical reaction sites with specific selected reagents. Subsequently, all the strands are pooled and subjected to a second partitioning based on a second codon region. The split-and-combine method is conducted an appropriate number of times to produce a library of typically between $10^3$ and $10^6$ different compounds. The split-and-combine method is cumbersome and generates only a relatively small library.

Gartner Z J and Liu D R (*J. Am. Chem. Soc.* 2001, 123, 6961-6963) discloses a method in which DNA is used to direct chemical reactions sequence-specifically. It is shown that the proximity effect provided by DNA-templated synthesis can be used to promote chemical reactions. When more than a single chemical entity is to participate in the formation of an encoded molecule, it is necessary to have a building block spaced from a reactive site of the template by one or more codons. Typically, the distance between the building block and the reactive site of the template amounts to several nucleotides, e.g. 30 nucleotides, which implies that the reaction at the largest distance from the template reactive site is less promoted relative to a chemical entity carried by a building block annealed to a codon next to the reactive site.

The present invention aims at suggesting a solution for increasing the local concentration of reactants to promote the probability of a reaction.

SUMMARY OF THE INVENTION

The present invention provides a method for synthesising a templated molecule, said method comprising the steps of:
a) providing at least one template comprising of one or more codons,
b) providing a first functional entity attached to a zipping domain, said zipping domain comprises a first part of a molecule pair, being capable of reversible interaction with a second part of the molecule pair,
c) providing one or more building blocks, each comprising an anti-codon, a further functional entity and a linker connecting the anti-codon and the functional entity, wherein the anti-codon complements a codon of a template, and the functional entity is connected to a zipping domain comprising the second part of said molecule pair and is capable of being chemically connected to the first functional entity,
d) contacting the components of step a), b), and c) with each other under conditions allowing specific hybridisation of the anti-codon(s) to the codon(s) of the template(s) and dimerization of the two parts of the molecule pair,
e) allowing the functional entity of the building block to form a chemical connection to the first functional entity,
f) optionally, cleaving one or more linkers, provided that at least one linker remains to connect the functional entities with the template,
g) obtaining a templated molecule attached to the template which directed the synthesis thereof.

The template comprises in a preferred embodiment two or more codons, such as three to fifteen codons. The first functional entity, which in an aspect of the invention can be a scaffold, can then be connected to two or more functional entities. The method may be conducted only once to connect a scaffold functional entity with the desired amount of functional entities or the steps of d) through g) may be repeated one or more times to sequentially add building blocks harbouring functional entities to be attached to a functional entity or a nascent templated molecule.

When multi-step synthesis is performed, the repetition of the steps d) through g) is conducted using the templated molecule attached to the template which directed the synthesis thereof according to step g) as the first functional entity attached to a zipping domain in the contacting step according to step d).

The zipper domains may be characterized as two interacting moieties able to reversibly dimerize in an ordered way, thereby bringing reactive groups attached to them into close proximity. Reversibility is required in a preferred aspect in order to allow different functional entities having the same dimerization domain to interact at different times with a complementary zipper domain attached to a reactive site. Many types of molecular moieties may be employed as zipper domains, of which here follows a non-comprehensive list of appropriate pairs of zipper domains: i) DNA/DNA, DNA/RNA, LNA/DNA, PNA/RNA, various combinations of nucleotides and nucleotide analogs; ii) peptide/peptide, e.g. base and acid leucine zipper (coiled coil structure of two alpha-helices), antibody/antigen; iii) nucleic acid-peptide, e.g. Zinck-finger DNA binding domain/dsDNA; iv) peptide/small organic molecule, e.g., streptavidin/biotin; v) small organic molecule/small organic molecule, e.g., nitrilotriacetic acid (NTA)/nitrilotriacetic acid (NTA)$Zn^{++i}$ vi) positively charged moiety/negatively charged moiety, e.g., polyglutamic acid/polylysine. The zipper box can be chosen according to the conditions of the reaction that it is supposed to enhance. For example, if the reaction is performed at moderate temperature and at reasonably high salt concentration, DNA/DNA zipper boxes may be used. By varying the length of the zipper box (the complementary DNA strands), one may design zipper boxes of desired stability and dynamics. Other types of zipper boxes will be very dependent on pH. For example, the interaction strength and dynamics of a glutamate/lysine pair will be dependent on pH, as for example the polyglutamate will be highly negatively charged at high pH, and not charged at all at low pH.

The functional entity is in an aspect of the invention attached to the template through one or more covalent links. However, it may be appropriate that the first functional entity is connected to a sequence of nucleic acids complementing a sequence of nucleic acids harboured by the template to enable the attachment of a scaffold to the template by hybridisation. In this way it will be possible to encode several different scaffolds by the template. In a preferred embodiment of the invention, the first functional entity is a scaffold, i.e. a chemical moiety which is amended, usually by addition of functional groups emanating from one or more building blocks. The scaffold may be a single reactive group or a chemical structure comprising two or more reactive groups. Usually, the scaffold remains attached to the template through-out the synthesis of the templated molecule.

Usually, when the zipping domain comprises nucleic acids, the polarity of the building block harbouring the first functional entity is reverse compared to the polarity of the building block harbouring the further functional entity, i.e. if the first functional entity is attached to the 5' end of an oligonucleotide, the further functional entity is preferably attached to the 3' end of building block oligonucleotide, or visa versa. In certain aspects, when more than a single building block is included in the formation of the templated molecule, it is preferred that the scaffold building block is annealed to a flanking position of the template, i.e. not placed between codons codon for building blocks.

The zipping domain may be placed relative to the first functional entity in any way that promotes the proximity of the functional entities. In one aspect, the zipping domain is present in the template. In one setup, the zipping domain is situated between a codon coding for a scaffold oligo and the codons coding for building blocks. In another aspect of the invention the zipping domain is a part of the linker of the building block. Preferably, the zipping domain is proximal to the functional entity. Still more preferred the zipping domain is spaced from the functional entity with no more than 2 nucleic acids monomers. In a most preferred embodiment, the zipping domain of the functional entity of the building block and the first functional entity is distanced from the respective entities with the same number of nucleic acid monomers to provide for a high local concentration of functional entities. The distance of the zipping domain of the functional entity of the building block and the first functional entity, respectively, to the functional entities are preferably zero nucleotide monomers. In other words, it is preferred that the two functional entities intended to form a connection is attached to the terminal nucleotide of the zipping domain.

The desired number of the nucleic acid monomers of the zipping domain depends largely on the temperature and stringency conditions in general used during the synthesis. If a low stringency and/or a relatively low temperature is preferred the number of nucleic acid monomers may be as low as 3. However, a low number of nucleic acid monomers in the sequence of the zipper domain may increase the risk of hybridisation to e.g. the template or building blocks. It is therefore, in general, preferred to use at least 4 nucleic acid monomers. According to a preferred embodiment of the invention the zipping domain sequence comprises 3 to 20 nucleic acid monomers. In a still more preferred embodiment the zipping domain sequence comprises 4 to 16 nucleic acid monomers. Most preferred is a zipping domain sequence comprising 5 to 10 nucleic acid monomers.

The linkage between the anti-codon and the a zipping domain may be a single bond or a chemical moiety up to several 100 Å, such as between 1 and 300 Å. The linkage may of any suitable chemical nature, however, it is in general preferred that the linkage is an oligonucleotide. In a preferred embodiment, the linkage is a single bond, i.e. the anti-codon abuts the zipping domain.

In a preferred aspect of the invention, the annealing temperature of the codon:anti-codon hybrid is higher than the annealing temperature of the zipping domain hybrid to ensure that the building block remain attached to the template even though the interaction of the zipping domains is eliminated. The above aspect is specifically preferred when the contacting according to step d) is performed by alternating the temperature below and above the annealing temperature of the zipping domain. The effect of the alternation is increased when the alternating is performed a plurality of times. To avoid the release of the building block from the template, the highest temperature is preferably below the annealing temperature of the codon:anti-codon hybrid.

According to a preferred aspect of the invention, when the template comprises two or more codons the building blocks attached to these codons have essentially identical sequences of the zipping domain. An alternation of the temperature will then attract the different functional entities annealed through building blocks to the scaffold. Thus, it is possible to have a variety of functional entities brought into close proximity of the scaffold.

The difference between the annealing temperatures of the codon:anti-codon hybrid and the dimerized zipping domains is suitably 10° C. or above. More preferred the difference between the annealing temperatures is 25° C. or above.

In an aspect of the invention the hybridisation of codons with anti-codons and zipper domain dimerisation occurs in separate steps, i.e. the conditions for allowing specific hybridisation of the anti-codon(s) to the codon(s) of the template(s) are distinct from the conditions allowing for optimal dimerisation of the two pairs of the molecule pair. The separation of the step provides for optimal conditions for each step. In the second step, the dimerisation step, it is preferred to use conditions that ensures that the codons and anti-codons remains attached and conditions that favours reaction between the functional entities.

The conditions during specific hybridisation of the anti-codon(s) to the codon(s) suitably include a concentration of codons and/or anti-codons, which is higher than the concentration of codons and/or anti-codons used during dimerisation of the two pairs of the molecule pair. The difference in concentration enhance the probability that the codon:ant-codon hybrid has been formed prior to the reaction of the functional entities, thereby ensuring the transfer of genetic information. Suitably, the the concentration during hybridisation of codon(s) and anti-codons is at least 10 times higher compared to the concentration used for dimerisation of the two pairs of the zipping domain. The diluted conditions during the zipping domain dimerisation also favours the template directed reactions rather cross-reactions among random reactive groups appearing in the media because the local concentration of encoded reactive groups relative to the concentration of reactive groups in general in the media is increased.

In an aspect of the invention, the method is used to generate a library of templated molecules attached to the template (or, alternatively, a complementing template) which directed the synthesis of the molecule. As an example, a library may be generated by having more than one possible codon:anti-codon interaction. This may be conducted by having several building blocks with different functional entities but similar anti-codons. However, to obtain a one-to-one relationship between the identity of the functional entity connected to the scaffold and the codon of the template, it is usually preferred that each building block carries a specific anti-codon which identify the functional entity.

A library preferably comprises a plurality of templates with different unique codons and/or order of unique codons. A plurality of building blocks having anti-codons corresponding to the unique codons of the templates is usually provided. In one aspect of the invention, a specific building block is provided for each of the unique codons. In another aspect some of the codons are not matched by a building block or alternatively blocked by a oligonucleotide sequence without a functional entity.

In the following the principle is illustrated for a specific non-limiting example. The anti-codons in this example are approximately 20 nucleotides long (and has a melting temperature towards its complementary sequence of approximately 60° C.), whereas the zipper domain is approximately 5 nucleotides long (and has a much lower melting temperature, e.g. around 17° C.). The building blocks and the plurality of templates are incubated together, at a medium temperature (e.g., 55° C.), allowing the anti-codons to find and bind to the corresponding codons. At this temperature, the anti-codons interact efficiently and specifically with the codons, whereas the zipper boxes do not interact efficiently. Excess un-bound building blocks are washed away. Then the reactions between reactive groups of neighbouring functional entities are initiated by lowering the temperature to e.g. 10° C., and potentially changing conditions other than the temperature. At 10° C. the zipper domains of the regular building blocks will interact with the complementary sequence of the zipper domain of the scaffold functional entity, thereby bringing the reactive groups into very close proximity (see FIG. 14). This increases the local concentration of the reactive groups significantly, and as a result the reactive groups react. Then again, the temperature is increased to the medium temperature (55° C.) and the zipping box is melted resulting in a separation of the functional entities. When the temperature subsequently is decreased to about 10° C., another building block may hybridize its zipper domain to the zipper domain of the scaffold, whereafter its functional entity may react with the scaffold.

Zipping Domains

The zipper box is a molecular affinity pair composed of two parts which has affinity for each other under certain environmental conditions. The essential property of the molecular affinity pair is that the two parts are capable of interacting in order to assemble the molecular affinity pair. In the biotechnological field a variety of interacting molecular parts are known which can be used as the molecular affinity pair. Examples include, but are not restricted to protein-protein interactions, protein-polysaccharide interactions, RNA-protein interactions, DNA-DNA interactions; DNA-RNA interactions, RNA-RNA interactions, biotin-streptavidin interactions, enzyme-ligand interactions, antibody-ligand interaction, protein-ligand interaction, ect.

The interaction between the molecular affinity parts may result in a strong or a week bonding. If a covalent bond is formed between the parties of the affinity pair the binding between the parts can be regarded as strong, whereas the establishment of hydrogen bondings, interactions between hydrophobic domains, and metal chelation in general results in a week bonding. In general relatively weak bonding is preferred. In a preferred aspect of the invention, the first part of the affinity pair is capable of reversible interacting with the second part of the affinity pair so as to provide for an attachment or detachment of the parts in accordance with the changing conditions of the media.

In a preferred aspect of the invention, the molecular affinity pair is based on an interaction between nucleotides, i.e. the first part of the affinity pair is a sequence of nucleotides and the second part of the affinity pair is a sequence of nucleotides capable of hybridising to the first part of the affinity pair. The first part of the affinity pair may be a part of the template or a building block and may comprise an oligonucleotide having nucleobases selected among the natural occurring nucleobases, i.e. adenine, cytosine, guanine, thymine, and uracil which are attached to a backbone, such as a repetitive sequence of (deoxy)ribose-phosphate units. The second part of the affinity pair can be an oligonucleotide having nucleobases which complements and is specifically recognised by the first part, i.e. in the event the first part contains cytosine, the second part contains guanine and visa versa, and in the event the first part contains thymine or uracil the second part contains adenine. In one aspect of the invention it is preferred however, that at least some of the nucleobases of the second part of the affinity pair are non-specific base-pairing nucleobases. non-specific base-pairing nucleobases are bases which, when attached to a backbone, are able to pair with at least two of the five naturally occurring *nucleobases* mentioned above. Preferably, the base pairing between the two or more natural nucleobases and the non-specifically base-pairing nucleobase occurs essentially iso-enegically, i.e. the bonds formed have a strength of the same order. The term "non-specifically base-pairing *nucleobase*" is used herein interchangeably with the term "universal base".

In natural tRNA the nucleobase inosine is found. Inosine has the ability to hybridise non-specifically with three of the nucleobases, i.e. cytosine, thymine, and adenine. Other synthetic compounds having the same ability of non-specifically base-pairing with natural nucleobases have been formed and includes among others the compounds depicted below

EXAMPLES OF UNIVERSAL BASES

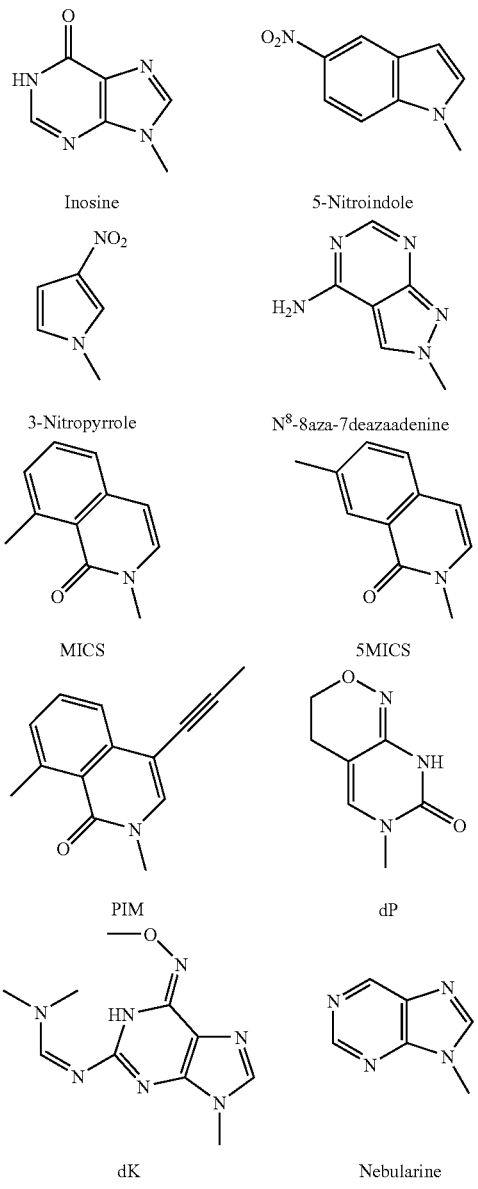

Template

The codons of the template may be any biochemical entity with an ability to be recognized specifically by another entity. It is preferred, however, that the codon is a sequence of nucleotides. The sequence of nucleotides carries a series of nucleo-bases on a back bone. The nucleobases of the codons may be any chemical entity able to be specifically recognized by a complementing entity. The nucleobases are usually selected from the natural nucleobases (adenine, guanine, uracil, thymine, and cytosine) but also the other nucleobases obeying the Watson-Crick hydrogen-bonding rules may be used, such as the synthetic nucleobases disclosed in U.S. Pat. No. 6,037,120.

The codon may be a single nucleotide. In the generation of a library, this will allow for the incorporation of four different functional entities into the template-directed molecule. However, to obtain a higher diversity a codon preferably comprises at least two and more preferred at least three nucleotides. Theoretically, this will provide for $4^2$ and $4^3$, respectively, different functional entities. The codons will usually not comprise more than 100 nucleotides. It is preferred to have codons with a sequence of 3 to 30 nucleotides.

The at least two codons of the template are arranged in sequence, i.e. next to each other and may be separated by a spacer group. Depending on the template-directed molecule intended to be formed, the template may comprise further codons. Each of the further codons may be separated by a suitable spacer group. Preferably, all or at least a majority of the codons of the template are arranged in sequence and each of the codons are separated from a neighbouring codon by a spacer group. Generally, it is preferred to have more than two codons on the template to allow for the synthesis of more complex template-directed molecules. In a preferred aspect of the invention the number of codons of the template is 2 to 100. Still more preferred is templates comprising 3 to 15 codons.

The spacer sequence may serve various purposes. In one setup of the invention, the spacer group identifies the position of a codon. Usually, the spacer group either upstream or downstream of a codon comprises information which allows determination of the position of the codon. The spacer group may also or in addition provide for a region of high affinity. The high affinity region will ensure that the hybridisation of the template with the anti-codon will occur in frame. Moreover, the spacer sequence adjusts the annealing temperature to a desired level.

A spacer sequence with high affinity can be provided by incorporation of one or more nucleobases forming three hydrogen bonds to a cognate nucleobase. An example of a nucleobase having this property is guanine. Alternatively, or in addition, the spacer sequence may be subjected to back bone modification. Several black bone modifications provides for higher affinity, such as 2'-O-methyl substitution of the ribose moiety, peptide nucleic acids (PNA), and 2'4' O-methylene cyclisation of the ribose moiety, also referred to as LNA (Locked Nucleic Acid).

The template may comprise flanking regions. One of the flanking regions can in an aspect of the invention serve to immobilize the template to a surface of a solid support such as a microarray. In another aspect of the invention the flanking region can encompasses a signal group, such a flourophor or a radio active group, to allow a direct detection of the presence of the template. The flanking regions can also serve as priming sites for an amplification reaction, such as PCR.

The template may also be immobilised on a solid support, such as a bead or matrix material by incorporating a biotin group in the template and subsequent coupling to a streptavidin coated solid support. Various other immobilisation methods are known to the skilled person, including coupling of the template to an antibody and immobilising the conjugate to a solid support coated with the appropriate antigen. In a preferred aspect, the priming site of the template serves the dual purpose of participating in an amplification reaction and as the means for immobilisation. The immobilisation can be effected, e.g. by treatment of the template comprising the priming site with a solid support comprising oligonucleotide sequences complementary to the priming site.

In one aspect, the first functional entity is covalently attached to the template. The covalent attachment of the reactive group usually entails that the template-directed molecule is formed at or in the vicinity of said reactive group. The final template-directed molecule is thus covalently attached to the template which directed and encoded the synthesis thereof. In the event a library is formed which comprises a plurality of complexes prepared in accordance with the invention, high stringency conditions for a selection procedure may be used without the risk of separating the template-directed molecule from the template.

In another aspect of the invention, the first functional entity is non-covalently attached to the template. Usually, the non-covalently attachment involves hydrogen bonds and hydrophobic interaction. Notably, the non-covalent attachment involves a hybridisation reaction between oligonucleotides or a part thereof. In a preferred embodiment, the functional entity is attached to a sequence of nucleotides, which complements a sequence of nucleotides of the template. The complementing sequence having attached the reactive group can serve as an anchor, i.e. to tie the nascent template-directed molecule to the template. Usually, the complementing sequence of the anchor has an annealing temperature higher than each of the building blocks to ensure attachment of the anchor even under condition which detaches the building blocks.

The first functional entity, such as a scaffold, may be linked to the template through a selectively cleavable linker, which enables the separation of the template-directed molecule from the template at a time decided by the experimenter. The first functional entity generally comprises a reactive group. The reactive group can be a part of a nascent template-directed molecule which, possibly in amended form, appears in the final templated molecule. The reactive group can also be a part of a scaffold, such as a molecular entity comprising more than one reactive group. Furthermore, the reactive group may be in a pro-form that has to be activated before the method of the invention is initiated.

In the aspect of the invention relating to the generation of a library, it may be desired to couple the first functional entity to an anti-codon complementing a (further) codon on the template, thus making it possible to have more than a single kind of functional entities present in the media. Alternatively, a functional entity or scaffold comprising the reactive group(s) may be varied.

When the template is linear, the first part of the molecular affinity pair is usually arranged between the active codon and a functional entity or a nascent templated molecule covalently connected or connected by hybridisation to the template to provide for a closer proximity between the reactive groups. More preferred, the first part of the molecular affinity pair is arranged proximal relative to the template reactive group.

The second part of the molecular affinity pair is positioned in the building block. The second part of the molecular affinity pair may be dispensed with in the event the codon to which the building block is attached to is close to the template reactive group, or expressed in another way, the anti-codon of the building block may be at least partly identical to the second part of the molecular affinity pair. Building blocks having anti-codons intended to interact with codons distal to the template reactive group, such as a scaffold, comprise as a section of the linker the second part of the molecular affinity pair. The term "distal" is to be understood as the case in which the active codon, i.e. the codon hybridised to the anti-codon of the building block, is interspaced relative to the template reactive group with one or more inactive codon(s).

The second part of the molecular affinity pair in the linker of the building block is preferably arranged proximal to the functional entity to increase the proximity between the building block reactive group and the template reactive group. More preferred the second part of the molecular affinity pair is spaced from the nucleotide carrying the functional entity by 0 to two nucleotides.

Hybridisation Conditions

It is within the capability of the skilled person in the art to construct the desired design of an oligonucleotide. When a specific annealing temperature is desired it is a standard procedure to suggest appropriate compositions of nucleic acid monomers and the length thereof. The construction of an appropriate design may be assisted by software, such as Vector NTI Suite or the public database at the internet address http://www.nwfsc.noaa.gov/protocols/oligoTMcalc.html.

The conditions which allow specific hybridisation of the codons and the anti-codons are influenced by a number of factors including temperature, salt concentration, type of buffer, and acidity. It is within the capabilities of the person skilled in the art to select appropriate conditions to ensure that the contacting between the templates and the building blocks are performed at hybridisation conditions. The temperature at which two single stranded oligonucleotides forms a duplex is referred to as the annealing temperature or the melting temperature. The melting curve is usually not sharp indicating that the annealing occurs over a temperature range. The second derivative of the melting curve is used herein to indicate the melting temperature.

Functional Entity

The functional entity of the building block serves the function of being a precursor for the structural entity eventually incorporated into the templated molecule. Therefore, when it in the present application with claims it is stated that a functional entity is transferred to a nascent template-directed molecule it is to be understood that not necessarily all the atoms of the original functional entity is to be found in the eventually formed template-directed molecule. Also, as a consequence of the reactions involved in the connection, the structure of the functional entity can be changed when it appears on the nascent templated molecule. Especially, the cleavage resulting in the release of the functional entity may generate a reactive group which in a subsequent step can participate in the formation of a connection between a nascent templated molecule and a functional entity.

The functional entity of the building block comprises at least one reactive group capable of participating in a reaction which results in a connection between the functional entity of the building block and the part of the template or complementing element hybridised to the template carrying the template reactive group. The connection is aided by one or more reactive groups of the functional entity. The number of reactive groups which appear on the functional entity is suitably one to ten. A building block featuring only one reactive group is used i.a. in the end positions of polymers, whereas building blocks having two reactive groups are suitable for the formation of the body part of a polymer or scaffolds capable of being reacted further. Two or more reactive groups intended for the formation of connections, are typically present on scaffolds. A scaffold may be a core structure, which forms the basis for the creation of multiple variants. The variant forms of the scaffold is typically formed through reaction of reactive groups of the scaffold with reactive groups of other building blocks, optionally mediated by fill-in groups or catalysts, under the creation of a connection between the entities. The functional entities to be connected to the scaffold may contain one, two or several reactive groups able to form connections.

The reactive group of the building block may be capable of forming a direct connection to a reactive group of another building block, nascent templated molecule or a template reactive site. In certain embodiments of the invention an indirect connection is formed using a bridging fill-in group. It is to be understood that not all the atoms of a functional entity necessarily is maintained in the (nascent) templated molecule formed. Rather, the functional entities are to be regarded as precursors for the structure of the final templated molecule.

The optional cleavage according to step f) can be performed in any appropriate way. In an aspect of the invention the cleavage involves usage of a reagent or and enzyme. The cleavage results in a transfer of the further functional entity to the nascent template-directed molecule or in a transfer of the nascent template-directed molecule to the functional entity of the building block. In some cases it may be advantageous to introduce new chemical groups as a consequence of linker cleavage. The new chemical groups may be used for further reaction in a subsequent cycle, either directly or after having been activated. In other cases it is desirable that no trace of the linker remains after the cleavage.

In another aspect, the connection and the cleavage is conducted as a simultaneous reaction, i.e. either the functional entity of the building block or the nascent template-directed molecule is a leaving group of the reaction. In general, it is preferred to design the system such that the connection and the cleavage occur simultaneously because this will reduce the number of steps and the complexity. The simultaneous connection and cleavage can also be designed such that either no trace of the linker remains or such that a new chemical group for further reaction is introduced, as described above.

It is important for the method according to the invention that at least one linker remains intact after the cleavage step. The at least one linker will link the nascent template-directed molecule to the template that directed the synthesis thereof. In case the method essentially involves the transfer of functional entities to a scaffold or an evolving polymer, the eventually scaffolded molecule or the polymer may be attached with a selectively cleavable linker. The selectively cleavable linker is designed such that it is not cleaved under conditions which result in a transfer of the functional entity to the nascent template-directed molecule.

Building Block

The building blocks used in the method according to the present invention may be designed in accordance with the particular entities involved in the building block. As an example, the anti-codon may be attached to the second part of the molecular affinity pair with a polyethylene glycol (PEG) linker and the functional entity may be directly attached to the second part of the molecular affinity pair. In another and preferred example, the anti-codon, the linker and the second part of the molecular affinity pair is a contiguous linear oligonucleotide.

The attachment of the functional entity to the linker is preferably at a terminal nucleotide or a nucleotide I or two nucleotides down the oligonucleotide. The attachment of the functional entity can be at any entity available for attachment, i.e. the functional entity can be attached to a nucleotide of the oligonucleotide at the nucleobase, or the back bone. In general, it is preferred to attach the functional entity at the phosphor of the internucleoside linkage or at the nucleobase.

In an aspect of the invention, a reactive group of the functional entity is attached to the linker oligonucleotide. The reactive group is preferably of a type which is able to create a connection to the the nascent template-directed molecule by either direct reaction between the respective reactive groups or by using a suitable fill-in group. The reactive group coupling the functional entity with the linker is preferably cleaved simultaneously with the establishment of the connection. The functional entity may in some cases contain a second reactive group able to be involved in the formation of a connection in a subsequent cycle. The second reactive group may be of a type which needs activation before it is capable of participating in the formation of a connection.

The oligonucleotide linker may be distanced from the the functional entity by a spacer moiety. The spacer may be designed such that the conformational spaced sampled by the reactive group is optimized for a reaction with a reactive group of a nascent template-directed molecule.

The design of building blocks comprising the anti-codon may be aimed at obtaining annealing temperatures in a specific range for all or some of the building block:template hybrids to ensure that the anti-codons have been annealed to the template before the functional entities are connected to each other through a chemical reaction. When the building blocks anneals to the template with essentially the same affinity it is necessary to add the building blocks in each cycle, i.e. the contacting of the building blocks with the template involves separate addition of the individual building blocks.

In an aspect of the invention, the building blocks are designed such that the building block to be added to the template in the first cycle has an annealing temperature lower than the subsequent building blocks. By using a temperature for the connection step in a second or subsequent step which is higher the previous step it is possible to have only the intended building blocks annealed to the template, while the majority of previous spent or non-reacted building blocks will be single stranded. Optionally, a recovery step may be used between each cycle to enrich the number of single stranded template available for annealing to a subsequent building block. The recovery step may involve the incorporation of biotin in the building block oligonucleotide and separation of the building blocks from the template using steptavidin coated beads at a temperature above the annealing temperature, as described elsewhere herein.

After the cleavage step the parts of the molecular affinity pair are separated to allow for a subsequent building block to interact with the first part of the zipping domain. Optionally, the cleavage step may be performed after the separation of the molecular affinity pair. In case the molecular affinity pair is a double stranded oligonucleotide, the parts of the affinity pair may be separated by increasing stringency, e.g. by increasing the temperature. In the alternative, the second part of the affinity pair carried by the building block, can be degraded enzymatically or chemically as disclosed below.

After the reaction of a building block, e.g. by transfer of a functional entity to a scaffold, the anti-codon may remain annealed to the template during a subsequent cycle. However, it is in general preferred to remove the anti-codon of a reacted building block not harbouring the nascent template-directed molecule from the template prior to repetition of steps d) to g). The absence of the annealed anti-codon makes it possible to incorporate universal bases in the linker to obtain an affinity between the linker and the inactive previous used codons.

The anti-codon can be removed using various techniques, such as separation from the template by increasing the stringency, typically by raising the temperature; partly or fully enzymatical digestion; or chemical degradation. The approach using increasing the stringency is the most simple to apply. However, in the event reannealing can occur or selective removal of the anti-codon is desired, it can be contemplated to use enzymatic or chemical approaches or a mixture thereof.

A method for removal of spent building blocks, non-reacted building blocks and excess building blocks involves the incorporation of biotin or a similar small molecule and withdrawal of said building block using the adherence between biotin and avidine or streptavidine on coated beads. More specifically, biotin is incorporated in the building block during the synthesis thereof. Following the transfer or alternatively the cleavage step of the invention, the mixture is treated with beads coated with streptavidin under conditions which allow for the coupling of streptavidin to biotin. Subsequently, the temperature is increased above the annealing temperature of the building block:template hybrid and the mixture is subjected to increased gravity, e.g by spinning in a centrifuge. The supernatant will then comprise the template liberated from the building blocks. An alternative to the biotin-streptavidin coupling is the formation of a S—S bridge. As an example, the oligonucleotide comprising the anti-codon is provided with a —SH group, such as a reduced product of the C6 S—S thiol modifier (Glen Research #10-1936-90). The —SH group of the building block can be coupled to another —SH group on a solid support under oxidising conditions and the building block can be removed together with the solid support by spinning if the solid material is a bead or by eluation if the solid support is a solid phase matrix of a column.

For some applications it may be of advantage to selectively degrade the anti-codon-containing oligonucleotide. Several methods are available for degradation of the RNA part of a DNA:RNA duplex. Accordingly, the template can be provided as a single stranded oligonucleotide and the anti-codon can be a single cognate RNA strand. The DNA:RNA duplex can then be degraded with an enzyme selected from RNAseH, RNAseA, RNAse 1. In the alternative, the RNA part of the RNA:DNA duplex can be degraded chemically by treatment under weak alkaline conditions (pH 9-10), or with aqueous $Pb(Ac)_2$.

If the internucleoside linker comprises a thiophosphate, the linker may be cleaved with iodine. Therefore, according to this approach, an oligonucleotide template, such as a DNA or RNA template having hybridised thereto a DNA or RNA anti-codon comprising a thiophospate in the internucleoside linker can be treated with aqueous iodine or iodoethanol to cleave the anti-codon.

According to another approach, a strand may be cleaved in a duplex if a DNA monomer contains a uracil nucleobase by first treating the duplex with uracilglycosylase to remove the uracil moiety and subsequently treating with weak acid. Yet another approach involves the inclusion of methyl phosphonate in the internucleoside linker and cleavage of the linker using piperidine, e.g. by treatment at 37° C. for an hour with a piperidine concentration of 100 mM.

The various methods of removal of the anti-codon from the template can be used in the selectively degradation of anti-codons. The advantage of selective degradation is especially apparent when the nascent template-directed molecule as well as the building block is encoded for by the template. In one aspect, a scaffold is coded for by the template and building blocks are sequentially incorporated. By using any of the above methods it is possible selectively to remove the building block, including the anti-codon and the linker, while the anti-codon used for recognising the codon which codes for a scaffold remains attached to the template.

Templated Molecule

When a strategy is followed wherein the eventually produced templated molecule is attached to a template via a complementing element, which may and may not involve an anti-codon, the affinity is relatively weak because only hydrogen bondings and hydrophobic interactions tight the parts together. Therefore, in an aspect of the invention, the complementing element finally harbouring the templated molecule, may be attached to the template through a complementing element:template hybrid having a higher annealing temperature than the other codon:anti-codon hybrids of the template. Alternatively, and in some applications preferably, the templated molecule is connected with the template which directed the syntheses thereof via a covalent link. The covalent link may be in addition to the hydrogen bondings or the covalent link may be a substitution. The presence of a covalent link allows for a more harsh chemical treatment of the complex. In one aspect of the invention, the covalent link is selectively cleavable to provide for a separation of the templated molecule from the complementary template.

The method according to the invention may, as a further step, involve the transfer of the templated molecule to an anchorage point on the template, or a sequence complementing the template, to establish an effective chemical connection between the template and the templated molecule. An effective coupling of the templated molecule to the template or a sequence complementary to the template can be desirable to allow for denaturing enrichment conditions or denaturing post-templating modification of the manufactured molecule. The anchorage may involve the presence of a reactive group on the templated molecule and a reaction partner on the template, whereby the reaction between these reactive groups will establish a covalent link. Alternatively, the anchorage point may be present on a complementary sequence hybridised to the template. In a preferred embodiment the complementing sequence has a higher annealing temperature than one or more of the building blocks, notably the terminal building block, to enable usage of a higher stringency during enrichment and, optionally, clearance of used building blocks.

Library

The present invention also relates to a library of bifunctional complexes. The library is composed of a plurality of different complexes, such as at least $10^3$, $10^6$, $10^9$, $10^{12}$, or $10^{15}$ different complexes. The plurality of different complexes is produced by initially providing a plurality of different templates as well as a plurality of building blocks. Each of the anti-codons of the building blocks is adapted so as to be capable of interacting with at least one codon of at least one template. The plurality of different templates is simultaneously subjected to the method described herein above. The propagation part of the method may be repeated a desired number of times to evolve the templated molecule. Each repetition of the propagation is initiated by contacting the templates with a new subset of further building blocks.

The various different templates of the present invention are conveniently constructed to follow a general scheme. According to the scheme, a number of coding sections are provided on the template. In turn, each of the coding sections specifies one or more unique codons. Thus, a specific template comprises a given number of unique codons. The plurality of templates can, taken as a whole, be characterized as a library comprising the total amount of the different combinations of unique codons possible, or any subset thereof. The coding sections are suitable positioned in a linear sequence, such that the individual coding sections are positioned immediately next to each other, optionally, interspaced by a spacer sequence. In some embodiments, it may be of advantage to use a branched template to ensure proximity of reactive groups, the introduction of catalysts in the vicinity of the reactive groups or the introduction of as third reactant.

The unique codons of the templates are preferably composed of a sequence of nucleic acid monomers, such as nucleotides. Each codon is preferably unique in the sense that within the same coding section no other codons have an identical sequence and length of nucleic acid monomers. Preferably, a unique codon does not have a corresponding sequence anywhere in the plurality of templates. To avoid hybridisation between individual templates it is also desirable to design each of the unique codons such that the complementary sequence thereof does not exist on any other templates.

The number of coding sections may be selected in accordance with inter alia the number of the desired final templated compounds, the building blocks available and the envisaged structure of the templated compound. According to the invention the number of coding regions is preferably at least 3 to achieve the desired diversity. The upper limit for the number of coding regions has not yet been elucidated; however it is believed that a number exceeding 100 may give practical problems. Generally, it is preferred to use templates having between 2 and 50 coding regions, more preferably between 3 and 30 and still more preferred between 4 and 15.

Within each of the coding regions the number of unique codons may be selected according to the need for diversity. The number of unique codons in each of the coding regions may be similar or different. The number of unique codons can be as low as one. This may be the choice when a specific molecular entity is wanted in the evolving templated molecule. The upper limit for the number of unique codons may be chosen quit high as long as specific hybridisation of oligonucleotides of the anti-codons to their complements on the templates occurs. An example of an upper limit may be 10,000, but may be chosen below this limit or above according to the need.

As an example of a relatively small library, around $10^6$ different complexes can be obtained for templates having 4 coding regions, wherein each coding region specifies 30 unique codons. If each of the unique codons only can be present once on the template, at least 120 different building blocks have to be provided. The plurality of templates and the building blocks may be used for the generation of a 4-mer compound, such as an alpha or beta peptide. A larger library of $10^{10}$ complexes may be prepared starting from templates having 5 coding regions and 100 unique codons within each coding region.

The library may be used for a variety of applications, including the search for compounds for use in therapeutic or diagnostic methods and plant protection compounds, like pesticides, fungicides ect. The library may comprise any number of complexes according to the invention.

One method to identify the most active compounds which can be used in e.g. therapeutic applications is to subject the library to an enrichment treatment. According to one aspect of the invention an enrichment of a library of complexes comprising templated molecules with respect to a predetermined activity, comprises the steps of:

i) establishing a first library of complexes comprising templated molecules, said library being obtainable according to any of the methods of the invention, ii) exposing the library to conditions enriching the library with complexes having the predetermined activity, iii) amplifying the complexes of the enriched library, iv) optionally, repeating step ii) to iii), and v) obtaining an enriched library having a higher ratio of complexes comprising templated molecules with the predetermined activity.

The amplification step is normally preferred, though not always necessary. Especially, when several cycles of enrichments are conducted it is of advantage to make an amplification to obtain sufficient complexes. In a preferred aspect of the invention, the amplification of the complexes of the enriched library comprises the steps of contacting the library of complexes with amplification means, amplifying the templates or the complementing templates, and conducting the method according to the invention using the amplification product as templates. The amplification means can be any of the nucleic acid amplification means suitable for the amplification of the template, such as PCR. Preferably, the amplification of the complex comprises a $10^1$ to $10^{15}$-fold amplification.

To allow for multiple enrichment cycles the steps ii) and iii) are repeated at least 2, 3, 5 times, such as at least 10 times, such as at least 15 times. The complexes may be identified after the completion of each cycle or may be only be identified after the last cycle. There is no explicit need for intermediate identifications as the amplification can be performed without knowing the sequence of the template or a sequence complementing the template, if the template or the complement thereof is provided with suitable primer regions. The identification after the enrichment process involves the determination of the sequence of the template and/or the structural determination of the templated molecule and/or the entire complex having the predetermined activity.

Preferably, the conditions enriching the library comprise contacting a binding partner to the templated molecules of interest. The binding partner may be in solution or may be directly or indirectly immobilised on a support. The enrichment is in general performed using an affinity or activity assay. In one aspect of the invention, the enrichment is conducted by screening for complexes having an affinity for—or an effect on—a target molecule or a target entity. In another aspect the enrichment is conducted by selection for catalytic activity. Alternatively, the conditions enriching the library involve any one or more of electrophoretic separation, gelfiltration, immunoprecipitation, isoelectric focusing, centrifugation, and immobilization.

The enrichment process can involve cells. Thus, in one embodiment, the conditions enriching the library comprise providing cells capable of internalising the templated molecule, or performing an interaction with the templated molecule having the desired predetermined activity.

When the library of complexes have been enriched to a small pool comprising complexes displaying a predetermined activity, it is desirable to obtain each of the complexes separately. The templated molecule can be obtained from the complex by cleaving the linker(s) of the one or more building blocks to release the templated molecule from the template.

Nucleotides

The nucleotides used in the present invention may be linked together in an oligonucleotide. Each nucleotide monomer is normally composed of two parts, namely a nucleobase moiety, and a backbone. The back bone may in some cases be subdivided into a sugar moiety and a internucleoside linker.

The nucleobase moiety may be selected among naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine hetero-cycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diamino-purine, 5-methylcytosine, 5-($C^3$-$C^6$)-alkynylcytosine, 5-fluorouracil, 5-bromouracil, pseudoisocytosine, 2-hydroxy-5-methyl-4-triazolopyridine, isocytosine, isoguanine, inosine and the "non-naturally occurring" nucleobases described in Benner et al., U.S. Pat. No. 5,432,272. The term "nucleo-base" is intended to cover every and all of these examples as well as analogues and tautomers thereof. Especially interesting nucleobases are adenine, guanine, thymine, cytosine, 5-methylcytosine, and uracil, which are considered as the naturally occurring nucleobases in relation to therapeutic and diagnostic application in humans.

Examples of suitable specific pairs of nucleobases are shown below:

Natural Base Pairs

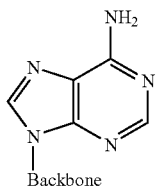
Adenine

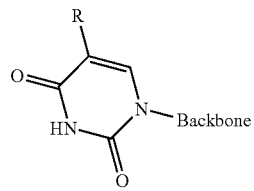
R = H: Uracil
R = CH$_3$: Thymine

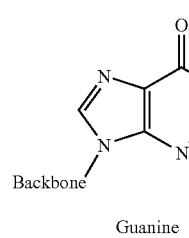
Guanine

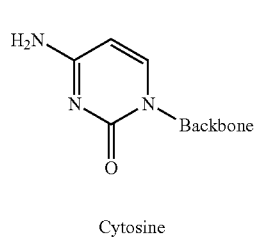
Cytosine

Synthetic Base Pairs

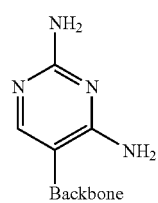

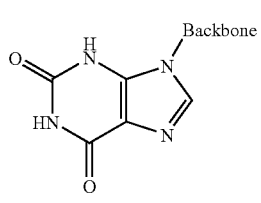

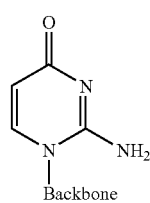

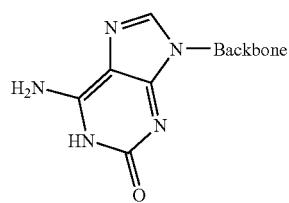

-continued

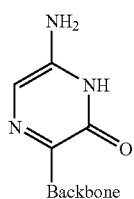

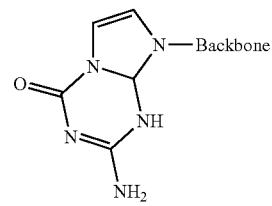

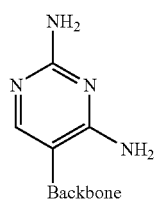

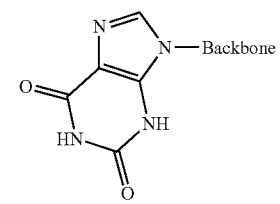

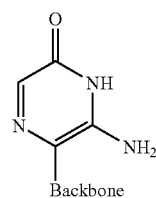

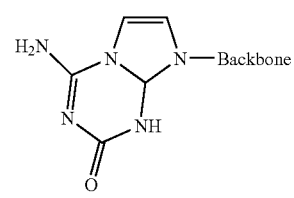

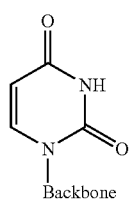

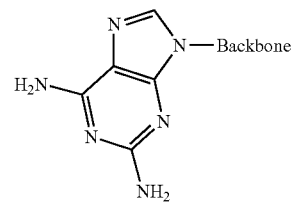

Synthetic purine bases

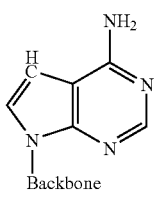
7-deaza adenine

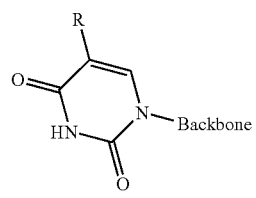
R = H: Uracil
R = CH$_3$: Thymine

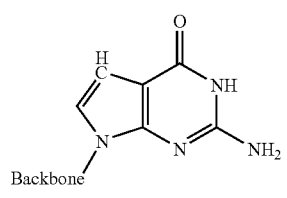
7-deaza guanine

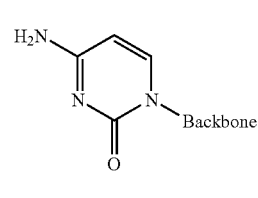
Cytosine

Suitable examples of backbone units are shown below (B denotes a nucleobase):

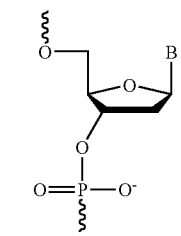
DNA

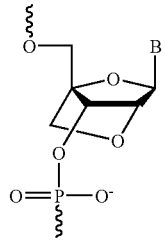
Oxy-LNA

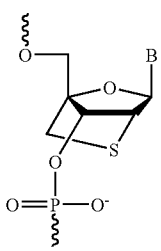
Thio-LNA

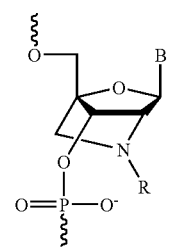
Amino-LNA
R = —H, —CH₃,

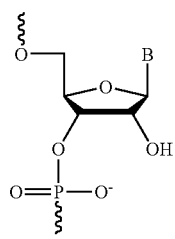
RNA

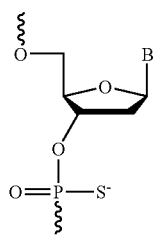
Phosphorthioate

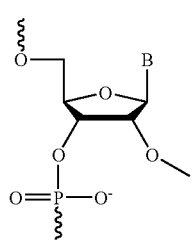
2'-O-Methyl

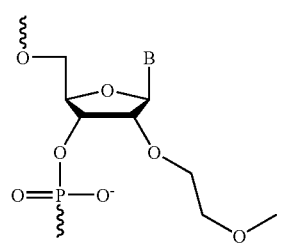
2'-MOE

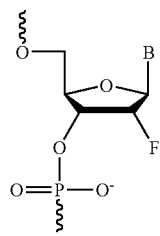
2'-Fluoro

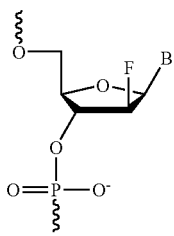
2'-F-ANA

-continued

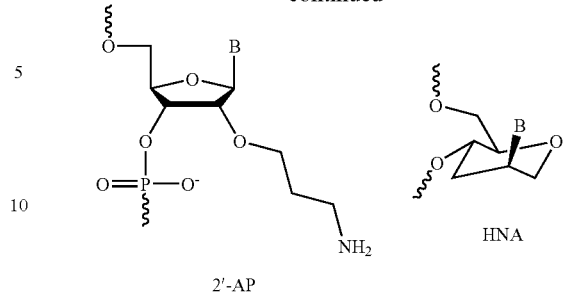
2'-AP    HNA

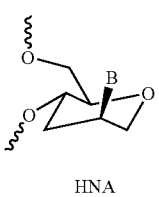

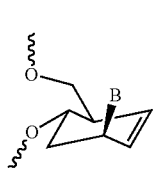
CeNA

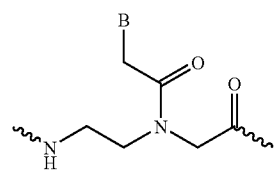
PNA

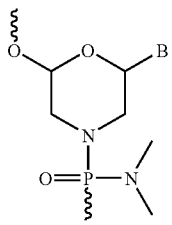
Morpholino

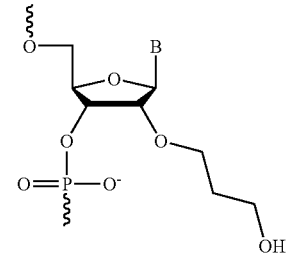
2'-(3-hydroxy)propyl

3'-Phosphoramidate    Boranophosphates

The sugar moiety of the backbone is suitably a pentose but may be the appropriate part of an PNA or a six-member ring. Suitable examples of possible pentoses include ribose, 2'-deoxyribose, 2'-O-methyl-ribose, 2'-flour-ribose, and 2'4'-O-methylene-ribose (LNA). Suitably the nucleobase is attached to the 1' position of the pentose entity.

An internucleoside linker connects the 3' end of preceding monomer to a 5' end of a succeeding monomer when the sugar moiety of the backbone is a pentose, like ribose of 2'-deoxyribose. The internucleoside linkage may be the natural occurring phospodiester linkage or a derivative thereof. Examples of such derivatives include phosphorothioate, methylphosphonate, phosphoramidate, phosphotriester, and phosphodithioate. Furthermore, the internucleoside linker can be any of a number of non-phosphorous-containing linkers known in the art.

Preferred nucleic acid monomers include naturally occurring nucleosides forming part of the DNA as well as the RNA family connected through phosphodiester linkages. The members of the DNA family include deoxyadenosine, deoxyguanosine, deoxythymidine, and deoxycytidine. The members of the RNA family include adenosine, guanosine, uridine, cytidine, and inosine. Inosine is a non-specific pairing nucleoside and may be used as universal base as discussed above because inosine can pair nearly isoenergetically with A, T, and C.

Each codon is complemented by an anti-codon. The anti-codon has the ability specifically to engage with the codon which it complements. The affinity between the codon and the complementing anti-codon is affected through hydrogen bondings following the well-known Watson-Crick base pairing system. Thus, the anti-codon may be composed of the same kind of nucleic acid monomers as the codon itself.

Functional Groups

The functional entity may comprise one or more functional groups, i.e. groups which eventually form part of the templated molecule. The templated molecule may comprise one or more of the following functional groups either alone or in combination:

1. Hydroxyls
2. Primary, secondary, tertiary amines
3. Carboxylic acids
4. Phosphates, phosphonates
5. Sulfonates, sulfonamides
6. Amides
7. Carbamates
8. Carbonates
9. Ureas
10. Alkanes, Alkenes, Alkynes
11. Anhydrides
12. Ketones
13. Aldehydes
14. Nitatrates, nitrites
15. Imines
16. Phenyl and other aromatic groups
17. Pyridines, pyrimidines, purines, indole, imidazole, and heterocyclic bases
18. Heterocycles
19. polycycles
20. Flavins
21. Halides
22. Metals
23. Chelates
24. Mechanism based inhibitors
25. Small molecule catalysts
26. Dextrins, saccharides
27. Fluorescein, Rhodamine and other fluorophores
28. Polyketides, peptides, various polymers
29. Enzymes and ribozymes and other biological catalysts
30. Functional groups for post-polymerization/post activation coupling of functional groups
31. Drugs, e.g., taxol moiety, acyclovir moiety, "natural products"
32. Supramolecular structures, e.g. nanoclusters
33. Lipids
34. Oligonucleotides, oligonucleotide analogs (e.g., PNA, LNA, morpholinos)
35. Hydrogen Reactive Groups Reactive groups relates among other things to groups which form part of the functional entity and are capable of participating in a reaction that forms a connection, either directly or via a suitable bridging molecular entity. Examples of reactive groups are listed below:

1. N-carboxyanhydrides (NCA)
2. N-thiocarboxyanhydrides (NTA)
3. Amines
4. Carboxylic acids
5. Ketones
6. Aldehydes
7. Hydroxyls
8. Thiols
9. Esters
10. Thioesters
11. conjugated system of double bonds
12. Alkyl halides
13. Hydrazines
14. N-hydroxysuccinimide esters
15. Epoxides
16. Haloacetyls
17. UDP-activated saccharides
18. Sulfides
19. Cyanates
20. Carbonylimidazole
21. Thiazinanones
22. Phosphines
23. Hydroxylamines
24. Sulfonates
25. Activated nucleotides
26. Vinylchloride
27. Alkenes, quinines Templated Molecules According to the present invention, virtually any molecule may be templated using the general method disclosed herein. Examples of compounds which can be synthesised include, but are not limited to, the compounds listed below:

alpha-, beta-, gamma-, and omega-peptides; mono-, di- and tri-substituted peptides; L- and D-form peptides; Cyclohexane- and cyclopentane-backbone modified beta-peptides; Vinylogous polypeptides; glycopolypeptides; polyamides; vinylogous sulfonamide peptide; polysulfonamide; conjugated peptide (i.e., having prosthetic groups); polyesters; polysaccharides; polycarbamates; polycarbonates; polyureas; poly-peptidylphosphonates; azatides; peptoids (oligo N-substituted glycines); polyethers; ethoxyformacetal oligomers; poly-thioethers; polyethylene glycols (PEG); polyethylenes; polydisulfides; polyarylene sulfides; polynucleotides; PNAs; LNAs; morpholinos; oligo pyrrolinone; polyoximes; polyimines; polyethyleneimine; polyacetates; polystyrenes; polyacetylene; polyvinyl; lipids; phospholipids; glycolipids; polycycles (aliphatic); polycycles (aromatic); polyheterocycles; proteoglycan; polysiloxanes; polyisocyanides; polyisocyanates; polymethacrylates; monofunctional, Difunctional, Trifunctional and Oligofunctional open-chain hydrocarbons; monofunctional, difunctional, trifunctional and oligofunctional nonaromatic carbocycles; monocyclic, bicyclic, tricyclic and polycyclic hydrocarbons; bridged polycyclic hydrocarbons; monofunctional, difunctional, trifunctional, and oligofunctional nonaromatic heterocycles; monocyclic, bicyclic, tricyclic, and polycyclic heterocycles, bridged polycyclic heterocycles; monofunctional, difunctional, trifunctional and oligofunctional aromatic carbocycles; monocyclic, bicyclic, tricyclic, and polycyclic aromatic carbocycles; monofunctional, difunctional, trifunctional and oligofunctional aromatic heterocycles; monocyclic, bicyclic, tricyclic and polycyclic heterocycles; chelates; fullerenes; steroids; cyclosporin analogs; as well as any combination of the above molecular moieties.

Enrichment

Selection or screening, commonly referred to as enrichment, of the library of complexes comprising templated molecules with respect to desired activities (for example binding to particular target, catalytic activity, or a particular effect in an activity assay) may be performed according to any standard protocol. For example, affinity selections may be performed according to the principles used for phage displayed, polysome-displayed or mRNA-protein fusion displayed peptides. Selection for catalytic activity may be performed by affinity selections on transition-state analogue affinity columns (Baca et al., Proc. Natl. Acad. Sci USA. 1997; 94(19): 10063-8), or by function-based selection schemes (Pedersen et al., Proc. Natl. Acad. Sci. USA. 1998, 95(18):10523-8). Screening for a desired characteristic may be performed according to standard microtiter plate-based assays, or by FACS-sorting assays.

Generally, affinity selections involve the immobilisation of a target or a binding partner on a solid support, such as a column. Subsequently, the complex manufactured according to the invention is added to the column under conditions allowing a part of the complexes to bind to the target. The complexes not bound to the target is eluted out of the column and discharged. The part of the complexes attached to the target may be amplified using the template associated with the templated molecule.

The choice of amplification method depends on the choice of codons and anti-codons. Natural oligonucleotides can be amplified by any state of the art method. These methods include, but is not limited to the polymerase chain reaction (PCR); as wells as e.g. nucleic acid sequence-based amplification (e.g. Compton, Nature 350, 91-92 (1991)), amplified anti-sense RNA (e.g. van Gelder et al., PNAS 85: 77652-77656 (1988)); self-sustained sequence replication system (e.g. Gnatelli et al., PNAS 87: 1874-1878 (1990)); polymerase independent amplification as described in e.g. Schmidt et al., NAR 25: 47974802 (1997), as well as in vivo amplification of plasmids carrying cloned DNA fragments. Ligase-mediated amplification methods may also be used, e.g., LCR (Ligase Chain Reaction).

For non-natural nucleotides the choices of efficient amplification procedures are fewer. As non-natural nucleotides per definition can be incorporated by certain enzymes including polymerases, it will be possible to perform manual polymerase chain reaction by adding the polymerase during each extension cycle.

For oligonucleotides containing nucleotide analogs, fewer methods for amplification exist. One may use non-enzyme mediated amplification schemes (Schmidt et al., NAR 25: 4797-4802 (1997)). For backbone-modified oligonucleotide analogs such as PNA and LNA, this amplification method may be used. Before or during amplification the templates or complementing templates may be mutagenized or recombined in order to create a larger diversity for the next round of selection or screening.

Following the amplification of the template part of the complex, the method according to the invention is conducted using the amplification product as the templates. The result is a reduced or enriched library of complexes of a template attached to a template molecule.

The selection and amplification steps may be repeated if considered necessary to further enrich the library. When the selection and amplification steps are repeated, the binding step involving the target and the complexes, is preferably performed under more strict conditions ensuring that only a part of the complexes adhere to the target.

The enrichment cycles may be performed 2 to 15 times or even more with enrichment in each cycle of 10 to 1000 times. In one approach, the starting library amounts to $10^{14}$ complexes. After seven cycles of enrichments with a 100 fold concentration in each cycle, the complex with the highest affinity to the target should, theoretically, be obtained. However, it is more likely that the final cycles deliver a small pool of interesting complexes, which have to be examined by other means.

After the final round of selection, it is often desirable to sequence individual templates, in order to determine the composition of individual templated molecules. If the template contains natural nucleotides, it is a standard routine to optionally PCR amplify the isolated templates (if the template is an RNA molecule, it is necessary to use reverse transcriptase to produce cDNA prior to the PCR-amplification), and then clone the DNA fragments into for example plasmids, transform these and then sequence individual plasmid-clones containing one or multiple tandem DNA sequences. In this case, it is practical to design a restriction site in both of the flanking sequences to the central coding sequence of the template (i.e., in the primer binding sites). This will allow easy cloning of the isolated nucleotides. Sequencing can be done by the standard dideoxy chain termination method, or by more classical means such as Maxam-Gilbert sequencing.

If the template contains non-natural nucleotides, it may not be feasible to clone individual sequences by transfer through a microbial host. However, using bead populations where each bead carries one oligonucleotide sequence, it is possible to clone in vitro, where after all the nucleotides attached to a specific bead may be optionally amplified and then sequenced (Brenner et al., 2000, Proc. Natl. Acad. Sci. USA 97, 1665-1670). Alternatively, one may dilute the population of isolates adequately, and then aliquot into microtiter plates so that the wells on average contain for example 0.1 templates. By amplifying the single templates by for example PCR, it will now be possible to sequence using standard methods. Of course, this requires that the non-natural nucleotides are substrates for the thermostable polymerase used in the PCR.

If alternative methods are used that require shorter oligonucleotides it may be desirable to design the starting template so as to contain restriction sites on either side of the encoding/ templating region of the template. Thereby, after the final selection round, the templates can be restricted, to obtain a short oligonucleotide encoding the templated molecule, and then these short oligonucleotides can be applied to various analytical procedures.

It is also possible to sequence the isolates by the use of a DNA array of oligonucleotides with random but predetermined sequences.

It may also be desirable to sequence the population of isolates as a pool, for example if the sequences are expected to be in register, for example because the initial library consisted of a degenerate sequence based on a polymer sequence with a known (relatively high) desired activity. Therefore, it is then expected that all the isolates have sequences similar to the initial sequence of the templates before selection. Thus, the population of isolates can be sequenced as a whole, to obtain a consensus sequence for the population as a whole.

The present invention is also directed to approaches that allow selection of small molecules capable of binding to different targets. The template-displaying molecule technology contains a built-in function for direct selection and amplification. The binding of the selected molecule should be selective in that they only coordinate to a specific target and thereby prevent or induce a specific biological effect. Ultimately, these binding molecules should be possible to use e.g. as therapeutic agents, or as diagnostic agents.

Template-displaying molecule libraries can easily be combined with screenings, selections, or assays to assess the effect of binding of a molecule ligand on the function of the target. In a more specific embodiment, the template-displaying method provides a rapid means for isolating and identifying molecule ligands which bind to supra-molecular, macro-supra-molecular, macro-molecular and low-molecular structures (e.g. nucleic acids and proteins, including enzymes, receptors, antibodies, and glycoproteins); signal molecules (e.g. cAMP, inositol triphosphate, peptides, prostaglandins); and surfaces (e.g. metal, plastic, composite, glass, ceramics, rubber, skin, tissue).

Specifically, selection or partitioning in this context means any process whereby the template-displaying molecule complex bound to a target molecule, i.e. the complex-target pair, can be separated from template-displaying molecules not bound to the target molecule. Selection can be accomplished by various methods known in the art.

The selection strategy can be carried out so it allows selection against almost any target. Importantly, no steps in this selection strategy need any detailed structural information of the target or the molecules in the libraries. The entire process is driven by the binding affinity involved in the specific recognition/coordination of the molecules in the library to a given target. However, in some applications, if needed, functionality can also be included analogous to selection for catalytic activity using phage display (Soumillion et al. (1994) J. Mol. Biol. 237: 415-22; Pedersen et al. (1998) PNAS. 18:10523-10528). Example of various selection procedures are described below.

This built-in template-displaying molecule selection process is well suited for optimizations, where the selection steps are made in series starting with the selection of binding molecules and ends with the optimized binding molecule. The single procedures in each step are possible to automate using various robotic systems. This is because there is a sequential flow of events and where each event can be performed separately. In a most preferable setting, a suitable template-displaying molecule library and the target molecule are supplied to a fully automatic system which finally generates the optimized binding molecule. Even more preferably, this process should run without any need of external work outside the robotic system during the entire procedure.

The libraries of template-displayed molecules will contain molecules that could potentially coordinate to any known or unknown target. The region of binding on a target could be into a catalytic site of an enzyme, a binding pocket on a receptor (e.g. GPCR), a protein surface area involved in protein-protein interaction (especially a hot-spot region), and a specific site on DNA (e.g. the major groove). The template-displaying molecule technology will primarily identify molecules that coordinate to the target molecule. The natural function of the target could either be stimulated (agonized) or reduced (antagonized) or be unaffected by the binding of the template-displaying molecules. This will be dependent on the precise binding mode and the particular binding-site the template-displaying molecules occupy on the target.

However, it is known that functional sites (e.g. protein-protein interaction or catalytic sites) on different proteins are more prone to bind molecules that other more neutral surface areas on a protein. In addition, these functional sites normally contain a smaller region that seems to be primarily responsible for the binding energy, the so called hot-spot regions (Wells, et al. (1993) Recent Prog. Hormone Res. 48; 253-262). This phenomenon will increase the possibility to directly select for small molecules that will affect the biological function of a certain target.

The template-displaying molecule technology of the invention will permit selection procedures analogous to other display methods such as phage display (Smith (1985) Science 228: 1315-1317). Phage display selection has been used successfully on peptides (Wells & Lowman. (1992) Curr. Op. Struct. Biol. 2, 597-604) proteins (Marks et al. (1992) J. Biol. Chem. 267: 16007-16010) and antibodies (Winter et al. (1994) Annu. Rev. Immunol. 12: 433-455). Similar selection procedures are also exploited for other types of display systems such as ribosome display (Mattheakis et al. (1994) Proc. Natl. Acad. Sci. 91: 9022-9026) and mRNA display (Roberts, et al. (1997) Proc. Natl. Acad. Sci. 94: 12297-302).

The linkage between the templated molecule (displayed molecule) and DNA replication unit (coding template) allows an identification of binding molecules using various selection strategies. This invention allows a broad strategy in identifying binding molecules against essentially any known target. In addition, this technology will also allow discovery of novel unknown targets by isolating binding molecules against unknown antigens (epitopes) and use these binding molecules for identification and validation.

As will be understood, selection of binding molecules from the template-displaying molecule libraries can be performed in any format to identify optimal binding molecules. A typical selection procedure against a purified target will include the following major steps: Generation of a template-displaying molecule library: Immobilization of the target molecule using a suitable immobilization approach; Adding the library to allow binding of the template-displayed molecules; Removing of the non-binding template-displayed molecules; Elution of the template-displayed molecules bound to the immobilized target; Amplification of enriched template-displaying molecules for identification by sequencing or to input for the next round of selection. The general steps are schematically shown in FIG. 12.

In a preferred embodiment, a standard selection protocol using a template-displaying molecule library is to use the bio-panning method. In this technique, the target (e.g. protein or peptide conjugate) is immobilized onto a solid support and the template-displayed molecules that potentially coordinate to the target are the ones that are selected and enriched. However, the selection procedure requires that the bound template-displayed molecules can be separated from the unbound ones, i.e. those in solution. There are many ways in which this might be accomplished as known to ordinary skilled in the art.

The first step in the affinity enrichment cycle is when the template-displayed molecules showing low affinity for an immobilized target are washed away, leaving the strongly binding template-displayed molecules attached to the target. The enriched population, remaining bound to the target after the stringent washing, is then eluted with, e.g. acid, chaotropic salts, heat, competitive elution with the known ligand or proteolytic release of the target/template molecules. The eluted template-displayed molecules are suitable for PCR, leading to many orders of amplification, i.e. every single template-displayed molecule enriched in the first selection round participates in the further rounds of selection at a greatly increased copy number. After typically three to ten rounds of enrichment a population of molecules is obtained which is greatly enriched for the template-displayed molecules which bind most strongly to the target. This is followed quantitatively by assaying the proportion of template-displaying molecules which remain bound to the immobilized target. The variant template sequences are then individually sequenced.

Immobilisation of the target (peptide, protein, DNA or other antigen) on beads might be useful where there is doubt that the target will adsorb to the tube (e.g. unfolded targets eluted from SDS-PAGE gels). The derivatised beads can then be used to select from the template-displaying molecules, simply by sedimenting the beads in a bench centrifuge. Alternatively, the beads can be used to make an affinity column and the template-displaying libraries suspension recirculated through the column. There are many reactive matrices available for immobilizing the target molecule, including for instance attachment to —$NH_2$ groups and —SH groups. Magnetic beads are essentially a variant on the above; the target is attached to magnetic beads which are then used in the selection. Activated beads are available with attachment sites for —$NH_2$ or —COOH groups (which can be used for coupling). The target can be also be blotted onto nitrocellulose or PVDF. When using a blotting strategy, it is important to make sure the strip of blot used is blocked after immobilization of the target (e.g. with BSA or similar protein).

In another preferred embodiment, the selection or partitioning can also be performed using for example: Immunoprecipitation or indirect immunoprecipitation were the target molecule is captured together with template-displaying binding molecules; affinity column chromatography were the target is immobilized on a column and the template-displaying libraries are flowed through to capture target-binding molecules; gel-shift (agarose or polyacrylamide) were the selected template-displaying molecules migrate together with the target in the gel; FACS sorting to localize cells that coordinates template-displaying molecules; CsCl gradient centrifugation to isolate the target molecule together template-displaying binding molecules; Mass spectroscopy to identify target molecules which are labelled with template-displaying molecules; etc., without limitation. In general, any method where the template-displaying molecule/target complex can be separated from template-displaying molecules not bound to the target is useful.

TABLE 1

Examples of selection method possible to use to identify binding molecules using the template-displaying technology.

| Type of Target | Method of choice |
| --- | --- |
| Soluble receptors | Direct immobilization, Immunoprecipitation, affinity column, FACS sorting, MS. |
| Cell surface receptor | Cell-surface subtraction selection, FACS sorting, Affinity column. |
| Enzyme inhibitors | Direct immobilization, Immunoprecipitation, affinity column, FACS sorting, MS. |
| Surface epitopes | Cell-surface subtraction selection, in-vivo selection, FACS sorting, Affinity column. |

Elution of template-displayed molecules can be performed in different ways. The binding molecules can be released from the target molecule by denaturation, acid, or chaotropic salts and then transferred to another vial for amplification. Alternatively, the elution can be more specific to reduce the background. Elution can be accomplished using proteolysis to cleave a linker between the target and the immobilizing surface or between the displaying molecule and the template. Also, elution can be accomplished by competition with a known ligand. Alternatively, the PCR reaction can be performed directly in the washed wells at the end of the selection reaction.

A possible feature of the invention is the fact that the binding molecules need not be elutable from the target to be selectable since only the encoding template DNA is needed for further amplification or cloning, not the binding molecule itself. It is known that some selection procedure can bind the most avid ligands so tightly as to be very difficult to elute. However the method of the invention can successfully be practiced to yield avid ligands, even covalent binding ligands.

Alternative selection protocol includes a known ligand as fragment of each displayed molecule in the library. That known ligand will guide the selection by coordinate to a defined part on the target molecule and focus the selection to molecules that binds to the same region. This could be especially useful for increasing the affinity for a ligand with a desired biological function but with a too low potency.

A further aspect of the present invention relates to methods of increasing the diversity or complexity of a single or a mixture of selected binding molecules. After the initial selection, the enriched molecules can be altered to further increase the chemical diversity or complexity of the displayed molecules. This can be performed using various methods known to the art. For example, using synthesized randomized oligonucleotides, spiked oligonucleotides or random mutagenesis. The randomization can be focused to allow preferable codons or localized to a predetermined portion or sub-sequence of the template nucleotide sequence. Other preferable method is to recombine templates coding for the binding molecules in a similar manner as DNA shuffling is used on homologous genes for proteins (Stemmer (1994) Nature 370:389-91). This approach can be used to recombine initial libraries or more preferably to recombine enriched encoding templates.

In another embodiment of the invention when binding molecules against specific antigens that is only possible to express on a cell surface, e.g. ion channels or transmembrane receptors, is required, the cells particle themselves can be used as the selection agent. In this sort of approach, cells lacking the specific target should be used to do one or more rounds of negative selection or be present in large excess in the selection process. Here, irrelevant template-displayed molecules are removed. For example, for a positive selection against a receptor expressed on whole cells, the negative selection would be against the untransformed cells. This approach is also called subtraction selection and has successfully been used for phage display on antibody libraries (Hoogenboom et al. (1998) Immunotech. 4: 1-20).

A specific example of a selection procedure can involve selection against cell surface receptors that become internalized from the membrane so that the receptor together with the selected binding molecule can make its way into the cell cytoplasm or cell nucleus. Depending on the dissociation rate constant for specific selected binding molecules, these molecules largely reside after uptake in either the cytoplasm or the nucleus.

The skilled person in the art will acknowledge that the selection process can be performed in any setup where the target is used as the bait onto which the template-displaying molecules can coordinate.

The selection methods of the present invention can be combined with secondary selection or screening to identify molecule ligands capable of modifying target molecule function upon binding. Thus, the methods described herein can be employed to isolate or produce binding molecules which bind to and modify the function of any protein or nucleic acid. It is contemplated that the method of the present invention can be employed to identify, isolate or produce binding molecules which will affect catalytic activity of target enzymes, i.e., inhibit catalysis or modifying substrate binding, affect the functionality of protein receptors, i.e., inhibit binding to receptors or modify the specificity of binding to receptors; affect the formation of protein multimers, i.e., disrupt quaternary structure of protein subunits; and modify transport properties of protein, i.e., disrupt transport of small molecules or ions by proteins.

A still further aspect of the present invention relates to methods allowing functionality in the selection process can also be included. For example, when enrichment against a certain target have been performed generation a number of different hits, these hits can then directly be tested for functionality (e.g. cell signalling). This can for example be performed using fluorescence-activated cell sorting (FACS).

The altered phenotype may be detected in a wide variety of ways. Generally, the changed phenotype is detected using, for example: microscopic analysis of cell morphology; standard cell viability assays, including both increased cell death and increased cell viability; standard labelling assays such as fluorometric indicator assays for the presence of level of particular cell or molecule, including FACS or other dye staining techniques; biochemical detection of the expression of target compounds after killing the cells; etc. In some cases, specific signalling pathways can be probed using various reporter gene constructs.

Secondary selection methods that can be combined with template-displaying molecule technology include among others selections or screens for enzyme inhibition, alteration or substrate binding, loss of functionality, disruption of structure, etc. Those of ordinary skill in the art are able to select among various alternatives of selection or screening methods that are compatible with the methods described herein.

The binding molecules of the invention can be selected for other properties in addition to binding, For example, during selection; stability to certain conditions of the desired working environment of the end product can be included as a selection criterion. If binding molecules which are stable in the presence of a certain protease is desired, that protease can be part of the buffer medium used during selection. Similarly, the selection can also be performed in serum or cell extracts or any type of media. As will be understood, when utilizing this template-displaying approach, conditions which disrupt or degrade the template should be avoided to allow amplification. Other desired properties can be incorporated, directly into the displaying molecules as will be understood by those skilled in the art. For example, membrane affinity can be included as a property by employing building blocks with high hydrophobicity.

Molecules selected by the template-displaying molecule technology can be produced by various synthetic methods. Chemical synthesis can be accomplished since the structure of selected binding molecules is readily obtained form the nucleic acid sequence of the coding template. Chemical synthesis of the selected molecules is also possible because the building blocks that compose the binding molecules are also known in addition to the chemical reactions that assemble them together.

In a preferred embodiment, the selected binding molecules is synthesized and tested in various appropriate in vitro and in vivo testing to verify the selected candidates for biological effects and potency. This may be done in a variety of ways, as will be appreciated by those in the art, and may depend on the composition of the bioactive molecule.

Target Identification and Validation

In another aspect, the present invention provides methods to identify or isolate targets that are involved in pathological processes or other biological events. In this aspect, the target molecules are again preferably proteins or nucleic acids, but can also include, among others, carbohydrates and various molecules to which specific molecule ligand binding can be achieved. In principal, the template-displaying molecule technology could be used to select for specific epitopes on antigens found on cells, tissues or in vivo. These epitopes might belong to a target that is involved in important biological events. In addition, these epitopes might also be involved in the biological function of the target.

Phage display with antibodies and peptide libraries has been used numerous times successfully in identifying new cellular antigens. (e.g. Pasqualini et al. (1996) Nature 380: 364-366; Pasqualini et al. (2000) Cancer Res. 60: 722-727; Scheffer et al. (2002) Br J Cancer 86: 954-962; Kupsch et al. (1999) Clin Cancer Res. 5: 925-931; Tseng-Law et al. (1999) Exp. Hematol. 27: 936-945; Gevorkian et al. (1998) Clin. Immunol. Immunopathol. 86: 305-309). Especially effective have been selection directly on cells suspected to express cell-specific antigens. Importantly, when selecting for cell-surface antigen, the template molecule can be maintained outside the cell. This will increase the probability that the template molecule will be intact after release for the cell surface.

In vivo selection of template-displayed molecules has tremendous potential. By selecting from libraries of template-displayed molecules in vivo it is possible to isolate molecules capable of homing specifically to normal tissues and other pathological tissues (e.g. tumours). This principle has been illustrated using phage display of peptide libraries (Pasqualini & Ruoslathi (1996) Nature 280: 364-366). This system has also been used in humans to identify peptide motifs that localized to different organs (Arap et al. (2002) Nat. Med. 2:121-127). A similar selection procedure could be used for the template-displaying libraries. The coding DNA in phage display protected effectively by the phage particle allows selection in vivo. Accordingly, the stability of the template in vivo will be important for amplification and identification. The template can be stabilised using various nucleotide derivatives in a similar way as have been used to stabilise aptamers for in vivo applications (Nolte (1996) Nature Biotechnol. 14: 1116-1121; Pagratis et al. (1997) Nature Biotechnol. 15: 68-72). However, it is reasonable to believe that the template structure will be stabilized against degradation due to the modified bases used for encoding the displayed molecule. Other types of protection are also possible where the template molecule is shielded for the solution using various methods. This could include for example liposomes, pegylation, binding proteins or other sorts of protection. The template molecule could also be integrated into another designed structure that protects the template form external manipulation. Fort example, the linker can be design to be incorporated in vesicles to position the templates inside the vesicle and the displaying molecules on the outside. The arrangement will protect the template molecules from external manipulate and at the same time allow exposure of the displaying molecules to permit selection.

Most antibodies have a large concave binding area which requires to some degree protruding epitopes on the antigens. Also, the antibody molecule is a large macro-molecule (150 KDa) which will sterically reduce the access for a number of different antigens (e.g. on a cell surface). The template-displaying technology should be able to access and recognize epitopes inaccessible to antibodies. The small binding molecules will be able to bind into active sites, grooves and other areas on an antigen. The coding template element is also smaller that an antibody which will increase the physical access of the template-binding molecule par. In addition, the diversity and complexity of the template-displaying molecule libraries will be much greater compare to peptide libraries. This will increase the possibility to find molecules that can coordinate to epitopes inaccessible to peptides due to inadequate chemistry. All together, the template-displaying molecule technology has the potential to identify novel antigens which is not possible to identify with antibodies or peptides.

One of ordinary skill in the art will acknowledge that various types of cells can be used in the selection procedure. It will also be understood that the selection for new antigens can be performed using subtraction methods as described previously.

Another aspect of the present invention relates to methods to validate the identified target. The identified binding molecules can directly be used if they change the biological response of the target. This can be done either in vitro using any direct or cell-based assay or directly in vivo studying any phenotypic response. The strength of this approach is that the same molecules are used both for identification and validation of various targets. Most favourable, the binding molecules could also directly be used as therapeutic agents.

In another preferred embodiment, the template-displaying molecules are used to pull out the target molecules. This can for instance be achieved by selection against a cDNA library expressed on bacteriophage (libraries vs. libraries). By mixing a template-displaying molecule library with a cDNA library it will be possible to find binding pairs between the small molecules in the template-displaying molecule library and proteins from the cDNA library. One possibility is to mix a phage display library with a template display library and do a selection for either the phage or template library. The selected library is then plated to localized phage clones and the DNA coding for the phage and template displayed molecules can then be identified using PCR. Other types of libraries than cDNA could also be used such as nucleic acids, carbohydrates, synthetic polymer.

In another embodiment of the invention the template-displaying molecule technology can be used to account for in vivo and in vitro drug metabolism. That could include both phase I (activation) and phase II (detoxification) reactions. The major classes of reactions are oxidation, reduction, and hydrolysis. Other enzymes catalyze conjugations. These enzymes could be used as targets in a selection process to eliminate displayed molecule that are prone to coordinate to these enzymes. The templates corresponding to these displayed molecules could subsequently be used to compete or eliminate these molecules when making template-displaying molecule libraries.

These obtained libraries will then be free of molecules that will have a tendency of binding to enzymes involved in phase I-II and possible be faster eliminated. For instance, a selection on each separate enzyme or any combination of cytochrome P450 enzymes, flavin monooxygenase, monoamine oxidase, esterases, amidases, hydrolases, reductases, dehydrogenases, oxidases UDP-glucuronosyltransferases, glutathione S-transferases as well as other relevant enzymes could be performed to identify these binding molecules that are prone to coordinate to these metabolic enzymes. Inhibitors are easily selected for due to their binding affinity but substrates need at least micro molar affinity to be identified.

Another interesting embodiment of this invention is the possibility to directly select for molecules that passively or actively becomes transported across epithelial plasma membrane, or other membranes. One possible selection assay is to use CaCO-2 cells, a human colon epithelial cell line, which is general, accepted as a good model for the epithelial barrier in the gastrointestinal guts. The CaCO-2 assay involves growing a human colon epithelial cell line on tissue culture well inserts, such that the resultant monolayer forms a biological barrier between apical and basolateral compartments. The template-displaying molecule libraries are placed either side of the cell monolayer and the molecules that can permeate the cell monolayer is collected and amplified. This process can be repeated until active molecules have been identified. Other cell line or setup of this assay is possible and is obvious for skill in the art.

A still further aspect of the present invention relates methods of selecting for stability of the selected molecules. This could be performed by subjecting an enriched pool of binding molecules to an environment that will possibly degrade or change the structure of the binding molecules. Various conditions could be certain proteases or a mixture of protease, cell extract, and various fluids from for example the gastrointestinal gut. Other conditions could be various salts or acid milieu or elevated temperature. Another possibility is to generate a library of known ligands and subject that library to stability tests and selection to identify stable molecules under certain conditions as describe above.

Therapeutic Applications

The template-displaying molecule technology of the invention may be used for blocking or stimulating various targets. A therapeutically relevant target is a substance that is known or suspected to be involved in a regulating process that is malfunctioning and thus leads to a disease state. Examples of such processes are receptor-ligand interaction, transcription-DNA interaction, and cell-cell interaction involving adhesion molecules, cofactor-enzyme interaction, and protein-protein interaction in intracellular signalling. Target molecule means any compound of interest for which a molecule ligand is desired. Thus, target can, for example, include a chemical compound, a mixture of chemical compounds, an array of spatially localized compounds, a biological macromolecule, such as DNA or mRNA, a bacteriophage peptide display library, a ribosome peptide display library, an extract made from biological materials such as bacteria, plants, fungi, or animal (e.g. mammalian) cells or tissue, protein, fusion protein, peptide, enzyme, receptor, receptor ligand, hormone, antigen, antibody, drug, dye, growth factor, lipid, substrate, toxin, virus, or the like etc., without limitation. Other examples of targets include, e.g. a whole cell, a whole tissue, a mixture of related or unrelated proteins, a mixture of viruses or bacterial strains or the like. etc., without limitation.

Therapeutic drug targets can be divided into different classes according to function; receptors, enzymes, hormones, transcription factors, ion channels, nuclear receptors, DNA, (Drews, J. (2000) Science 287:1960-1964). Among those, receptors, nuclear receptors, and metabolic enzymes constitute overwhelmingly the majority of known targets for existing drugs. Especially, G Protein-Coupled Receptors (GPCR) constitutes one of the most important classes of drug targets together with proteases for pharmacological intervention. Although the above examples are focused on the most relevant targets, it will be self-evident for a person skilled in the art that any other therapeutic target may be of interest.

The present invention employing the template-displaying molecule technology can be utilized to identify agonists or antagonists for all these classes of drug targets, dependent on the specific properties each target holds. Most of the targets are possible to obtain in a purified form for direct selection procedures. Other targets have to be used when they are in their native environments such as imbedded cell surface receptors. In those situations the selection using the template-displaying molecule libraries can be performed using subtraction-selection described previously.

One specific application of the template-displaying molecule technology of the invention is to generate molecules that can function as antagonists, where the molecules block the interaction between a receptor and one or more ligands. Another application includes cell targeting. For example, the generated molecules recognizing specific surface proteins or receptors will be able to bind to certain cell types. Such molecules may in addition carry another therapeutic agent to increase the potency and reduce the side-effects (for example cancer treatment). Applications involving antiviral agents are also included. For example, a generated molecule, which binds strongly to epitopes on the virus particle, may be useful as an antiviral agent. Another specific application of the template-displaying molecule technology of the invention is to generate molecules that can function as agonists, where the molecules stimulate or activate a receptor to initiate a cellular signalling pathway.

BRIEF DESCRIPTION OF THE FIGURES

The following figures are referred to in this description:

FIG. 5 shows a reproduction of a PAGE gel showing the influence of different pH profiles on cross-linking efficiency.

FIG. 6 shows a reproduction of a PAGE gel displaying cross-linking efficiency at pH 9.

FIG. 13 shows a schematic drawing of the use of a dimerisation domain in the synthesis of (A) a scaffolded molecule and (B) a polymeric molecule.

FIG. 16 disclose two oligo setups used in the examples.

FIG. 24 discloses the results of experiments E to H reported in example 21.

In FIG. 13, a schematic drawing of the use of a dimerisation domain in the synthesis of (A) a scaffolded molecule and (B) a polymeric molecule is showed. When templating a scaffolded molecule (containing in this example four reactive groups of the same kind, Y), it is convenient to use four building blocks with identical zipper boxes ("b"), and one building block (carrying the four reactive groups Y) with a zipper box ("a") that is complementary to ("b"). When templating a polymeric molecule one may alternate between the zipper identity, i.e. first building block carries a zipper box ("a"), second building block in the array carries ("b") that dimerize with ("a"), third building block carries ("a"), etc.

Figure 14:
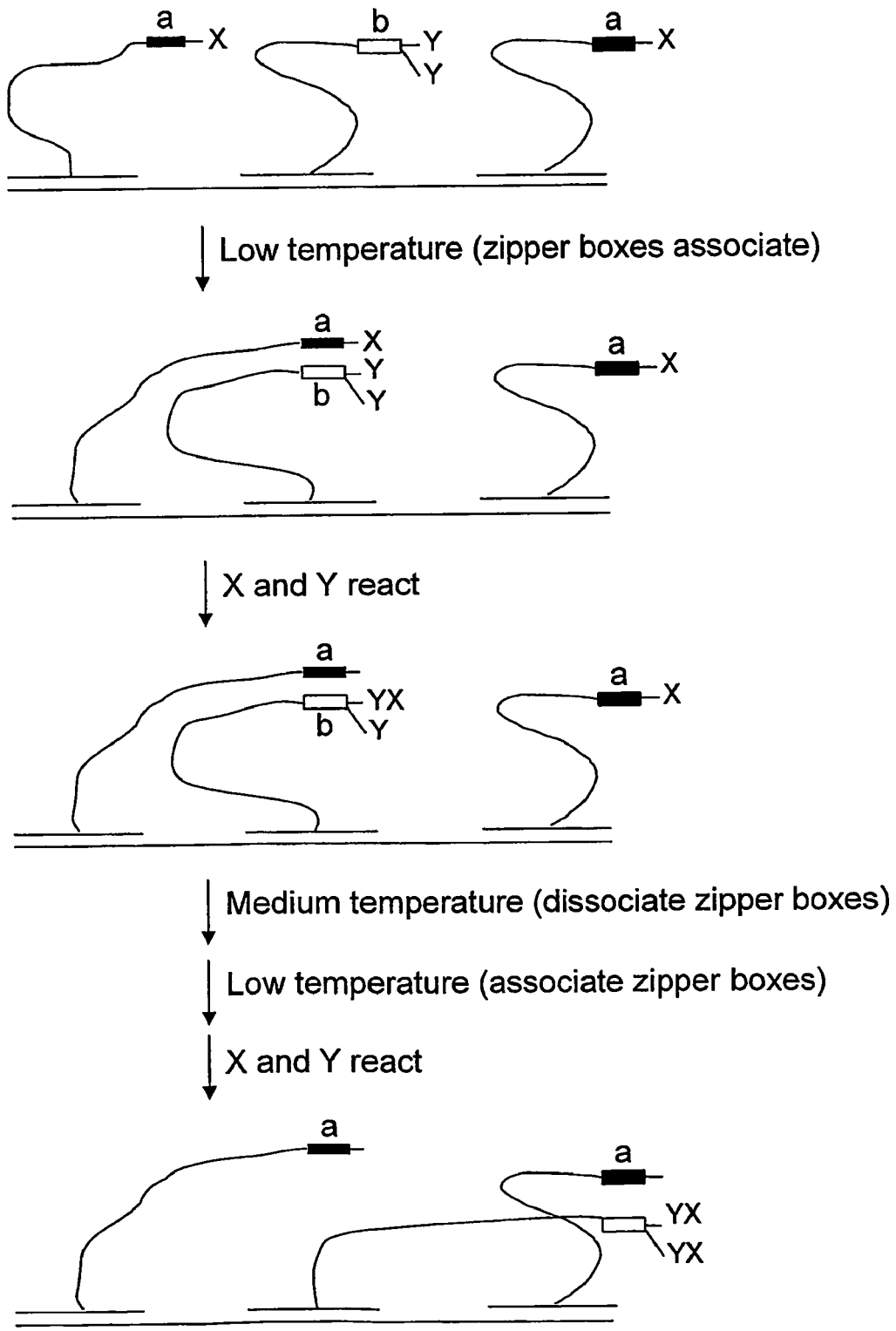
FIG. 14 shows a preferred embodiment of the general principle.

The preferred embodiment shown in FIG. 14 increases the local concentration of the reactive groups X and Y, by bringing X and Y into closer proximity through the dimerization of two zipper boxes. In this example, three building blocks are shown, each carrying a zipper box, two of which having the same sequence ("a") and one is the complementary sequence ("b"). First, the building blocks are annealed to the template at a medium temperature (where the interaction between the zipper boxes is insignificant). Then the temperature is decreased to a lower temperature where two complementary zipper domains ("a" (of the first building block) and "b" (of the second building block)) anneal to each other. This brings X and Y into close proximity, and X and Y may react to form YX. In the example, the reaction between X and Y involves a transfer of X from the first building block to the second building block carrying Y. When the temperature is increased to a medium temperature the zipper box dissociates. When the temperature is then lowered the zipper domain of the second building block may anneal to the zipper box of the third building block (which carries a reactive group X). As a result, this X may now be transferred to the second building block, as a result of the increased proximity and hence increased reactivity between X and Y.

EXAMPLE

General Methods and Materials for Examples 1 to 11

In order to examine the reaction efficiency between two reactive groups, each coupled to a oligonucleotide, when the two oligos are annealed to neighbouring sites on the same template, the general set-up shown immediately below was used. The two oligos contain terminal nucleotides (X, Y, and Z) derivatized with a carboxylic acid or an amine, as described below the figure. After reaction ("cross-linking") of the reactive groups on the termini of the two oligos, the cross-linking efficiency was analyzed by polyacrylamide gel electrophoresis, as the two oligos become coupled as a result of this cross-linking, and therefore migrate slower through the column.

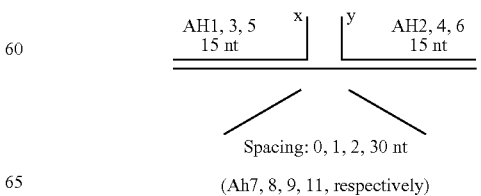

Building Blocks:

```
Ah 1:    5'-GCTACTCGTACGAGX    (SEQ ID NO: 1)
Ah 3:    5'-GCTACTCGTACGAGY    (SEQ ID NO: 2)
Ah 5:    5'-GCTACTCGTACGAGZ    (SEQ ID NO: 3)
Ah 2:    5'-XCACTTGCAGACAGC    (SEQ ID NO: 4)
Ah 4:    5'-YCACTTGCAGACAGC    (SEQ ID NO: 5)
Ah 6:    5'-ZCACTTGCAGACAGC    (SEQ ID NO: 6)
Ah 14:   5'-GCTACTCGTACGAG     (SEQ ID NO: 7)
Ah 23:   5'-GCTACTGGCATCGGX    (SEQ ID NO: 8)
Ah 24:   5'-GCTACTGGCATCGGY    (SEQ ID NO: 9)
Ah 27:   5'-YCACTTGCAGACAGC    (SEQ ID NO: 10)
```

In examples pertaining to a zipper box the following sequences was used

```
AH36:                                    (SEQ ID NO: 11)
5'-CGACCTCTGGATTGCATCGGTCATGGCTGACTGTCCGTCGAA-
TGTGTCCAGTTACX

AH37:                                    (SEQ ID NO: 12)
5'-ZGTAACTGGACTGTAAGCTGCCTGTCAGTCGGTACTGACCT-
GTCGAGCATCCAGCT

AH51:                                    (SEQ ID NO: 13)
5'-ZGTAACACCTGTGTAAGCTGCCTGTCAGTCGGTACTGACCT-
GTCGAGCATCCAGCT

AH67:                                    (SEQ ID NO: 14)
5'-ZCATTGACCTGTGTAAGCTGCCTGTCAGTCGGTACTG-
ACCTGTCGAGCATCCAGCT

AH69:                                    (SEQ ID NO: 15)
5'-AGZAACACCTGTGTAAGCTGCCTGTCAGTCGGTACTG-
ACCTGTCGAGCATCCAGCT

AH66:                                    (SEQ ID NO: 16)
5'-ZTTGTAACTGGACTGTAAGCTGCCTGTCAGTCGGTACTGACC-
TGTCGAGCATCCAGCT

AH65:                                    (SEQ ID NO: 17)
5'-CGACCTCTGGATTGCATCGGTCATGGCTGACTGTCCGTCG-
AATGTGTCCAGTTACTTX
```

Zipper box sequences are underlined.
X=Carboxy-dT
Y=Amino-Modifier C2 dT
Z=Amino-Modifier C6 dT

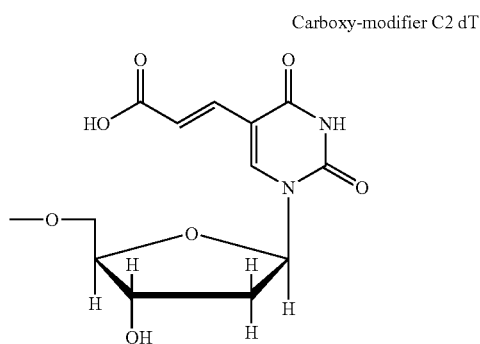
Carboxy-modifier C2 dT

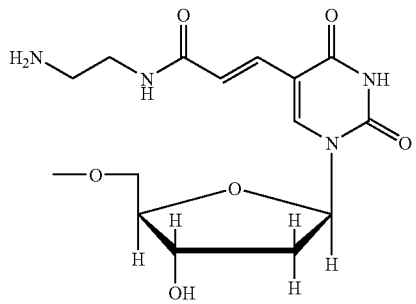
Amino modifier C2 dT

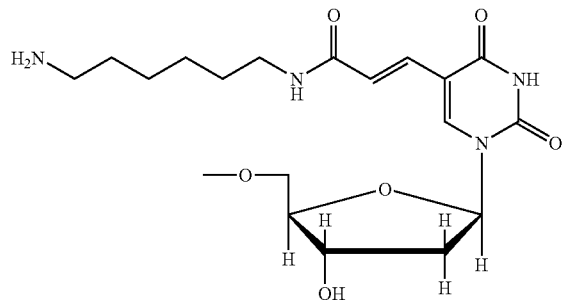
Amino modifier C6 dT

The oligonucleotides were prepared following the conventional phosphoamidite approach. X was incorporated using the commercially available carboxy-dT phosphoramidite (10-1035-90 from Glen research). The oligonucleotides terminated with Y and Z can be prepared from the corresponding X terminated oligonucleotides using the general procedure:

Templates:

```
Ah 28:                                   (SEQ ID NO: 18)
5'-GCTGTCTGCAAGTGAACCGATGCCAGTAGC

Ah 38:                                   (SEQ ID NO: 19)
5'-AGCTGGATGCTCGACAGGTCCCGATGCAATCCAGAGG TCG

Ah 7:                                    (SEQ ID NO: 20)
5'-GCTGTCTGCAAGTGAACTCGTACGAGTAGCGACAGTCGACATCGGTC
ACG-biotin-3'

Ah 8:                                    (SEQ ID NO: 21)
5'-GCTGTCTGCAAGTGACACTCGTACGAGTAGCGACAGTCGACATCGGT
CACG-biotin-3'

Ah 9:                                    (SEQ ID NO: 22)
5'-GCTGTCTGCAAGTGACGACTCGTACGAGTAGCGACAGTCGACATCGG
TCACG-biotin-3'

Ah 11:                                   (SEQ ID NO: 23)
5'-GCTGTCTGCAAGTGACGACTGATCCAGT-
GACATGCGTACCATCGAACTCGTAC
GAGTAGCGACAGTCGACATCGGTCACG-biotin-3'
```

The templates was prepared by conventional phosphoramidate synthesis.

Buffers.
Buffer A (100 mM Hepes pH=7.5, 1 M NaCl)
Buffer B: (100 mM NaPO$_4$ pH=6, 1 M NaCl)
Buffer C: (100 mM NaBorate pH=9, 1 M NaCl)
Buffer D: (100 mM NaBorate pH=10, 1 M NaCl)
Buffer E: (500 mM NaPO$_4$ pH=7, 1 M NaCl)
Buffer F: (500 mM NaPO$_4$ pH=8, 1 M NaCl)

Annealing of DNA Oligonucleotides.

Mix oligos in relevant buffer and heat at 80° C. then cool to 28° C. (−2° C./30 sek).

5'-Labeling with $^{32}$p.

Mix 200 pmol oligonucleotide, 2 μl, 10× phosphorylation buffer (Promega cat#4103), 1 μl T4 Polynucleotid Kinase (Promega cat#4103), 1 μl γ-$^{32}$P ATP, H$_2$O ad 20 μl. Incubate at 37° C., 10-30 minutes.

PAGE (Polyacrylamide Gel Electrophoresis).

The samples are mixed with formamide dye 1:1 (98% formamide, 10 mM EDTA, pH 8, 0.025% Xylene Cyanol, 0.025% Bromphenol Blue), incubate at 80° C. for 2 minutes, and run on a denaturing 10% polyacrylamide gel. Develop gel using autoradiography (Kodak, BioMax film).

Example 1

Mix 2 μl Buffer A, 2 μl relevant oligo 1 (2 pmol/ul), 2 μl relevant oligo 2 (2 pmol/ul), 4 μl relevant oligo 3 (2 pmol/ul) (See table 1, below).

TABLE I

| Experiment | Oligo 1 ($^{32}$P-labelled) | Oligo 2 | Oligo 3 |
|---|---|---|---|
| A | Ah 3 | Ah 4 | Ah 7 |
| B | Ah 5 | Ah 6 | Ah 7 |
| C | Ah 5 | Ah 6 | None |
| D | Ah 5 | Ah 6 | Ah 8 |
| E | Ah 5 | Ah 6 | Ah 9 |
| F | Ah 14 | Ah 6 | Ah 7 |

Anneal as described above. Add 1 μl 100 mM, 1 μl 10 mM, or 0.1 μl 10 mM TSAT (Tris-succinimidyl aminotriacetate, Pierce cat#33063 dissolved in DMSO). Incubate at 25° C. for about 1 h, then analyze by 10% urea polyacrylamide gel electrophoresis.

Figure 1:
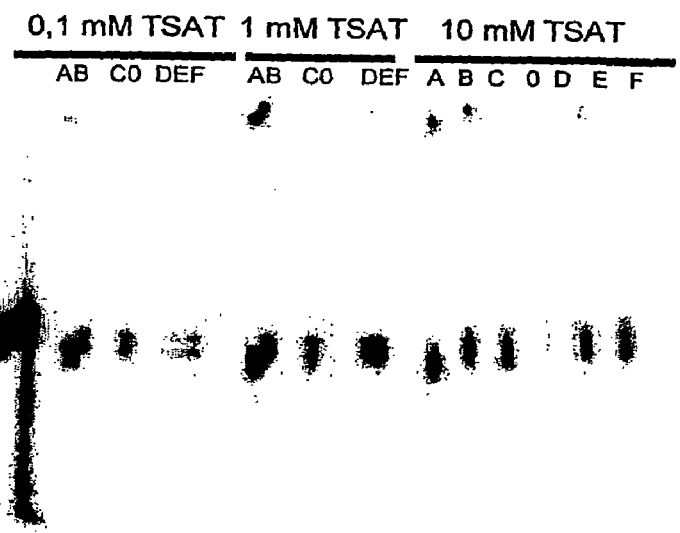
FIG. 1 shows a reproduction of a PAGE gel displaying cross-linking of amino functionalities of two oligonucleotides annealed to a common template.

The results are shown in FIG. 1.

Example 2

Mix 2 μl Buffer A, 2 μl relevant oligo 1 (0.2 pmol/ul), 1 μl relevant oligo 2 (10 pmol/ul), 1 μl relevant oligo 3 (10 pmol/ul), 4 μl H$_2$O. (See table II, below)

TABLE II

| Experiment | Oligo 1 ($^{32}$P-labelled) | Oligo 2 | Oligo 3 |
|---|---|---|---|
| G | Ah 5 | Ah 6 | None |
| H | Ah 5 | Ah 6 | Ah 7 |
| I | Ah 5 | Ah 6 | Ah 8 |
| J | Ah 5 | Ah 6 | Ah 9 |
| K | Ah 5 | Ah 6 | Ah 11 |

Anneal as described above. Add 1 μl 100 mM, 10 mM or 1 mM TSAT (Tris-succinimidyl aminotriacetate, Pierce cat#33063 dissolved in DMSO). Incubate at 25° C. for about 5 h, then run 10% urea polyacrylamide gel, as described above.

Figure 2:
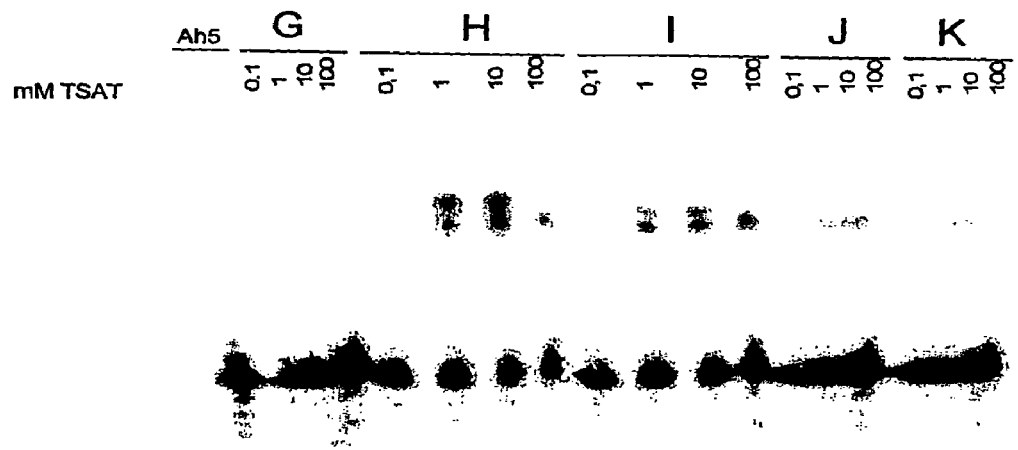
FIG. 2 shows a reproduction of a PAGE gel showing two oligonucleotides annealed to common template and cross-linked with a spacing of 0, 1, 2, and 30 base pair.

The results are shown in FIG. 2

Example 3

Mix 2 μl Buffer A, 2 μl relevant oligo 1 (0.2 pmol/ul), 1 μl relevant oligo 2 (10 pmol/ul), 1 μl relevant oligo 3 (10 pmol/ul), 4 μl H$_2$O. (See table III, below)

TABLE III

| Experiment | Oligo 1 ($^{32}$P-labelled) | Oligo 2 | Oligo 3 |
|---|---|---|---|
| L | Ah 1 | Ah 6 | None |
| M | Ah 1 | Ah 6 | Ah 7 |
| N | Ah 1 | Ah 6 | Ah 8 |
| O | Ah 1 | Ah 6 | Ah 9 |
| P | Ah 1 | Ah 6 | Ah 11 |

Anneal as described above. Add 1 μl 1M, 100 mM, 10 mM or 1 mM EDC (1-Ethyl-3-(3-dimethylaminopropyl) Carbodiimide Hydrochloride, Fluka #03450) and 1 μl 100 mM NHS (N-Hydroxysuccinimid) (Aldrich cat #13.067-2). Incubation at 25° C. for about 5 h, and analyze by 10% urea polyacrylamide gel electrophoresis, as described above.

Figure 3:
FIG. 3 shows a reproduction of a PAGE gel displaying cross-linking of two oligonucleotides terminated with a amine and carboxylic acid, respectively.

The results are shown in FIG. 3.

Example 4

Mix 2 μl buffer A, B, C, D, E or F, 2 μl relevant oligo 1 (0.2 pmol/ul), 1 μl relevant oligo 2 (10 pmol/ul), 1 μl relevant oligo 3 (10 pmol/ul), 4 μl H$_2$O. (See table IV, below)

TABLE IV

| Experiment | Oligo 1 ($^{32}$P-labelled) | Oligo 2 | Oligo 3 |
|---|---|---|---|
| Q | Ah 1 | Ah 6 | Ah 7 |
| R | Ah 5 | Ah 6 | Ah 7 |

Anneal as described above. Experiment Q is added 1 μl 100 mM EDC and 1 μl 100 mM NHS. Experiment R is added 1 μl 100 mM TSAT. Incubate at 25° C. for about 1.5 h, and then analyze by 10% urea polyacrylamide gel electrophoresis.

Figure 4:
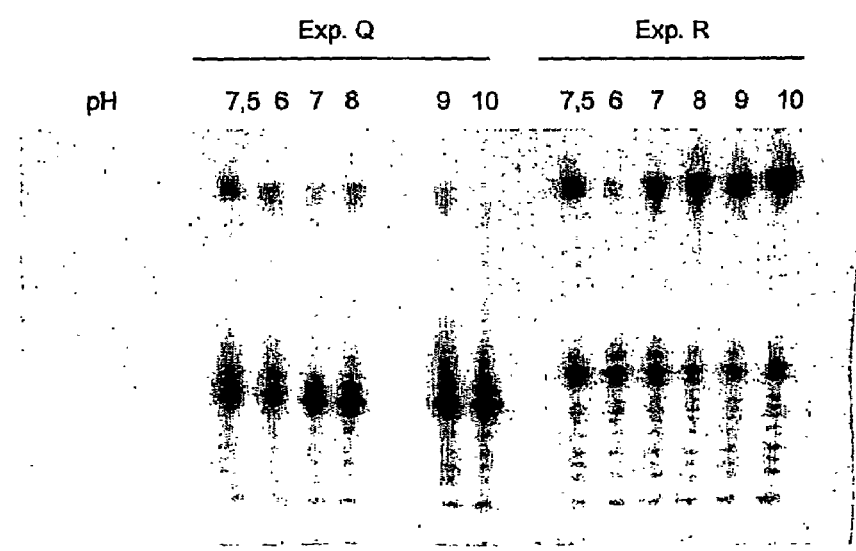
FIG. 4 shows a reproduction of a PAGE gel showing the influence of different pH profiles on cross-linking efficiency.

The results are shown in FIG. 4.

Example 5

Mix 2 μl buffer A or D, 2 μl relevant oligo 1 (0.2 pmol/ul), 2 μl relevant oligo 2 (10 pmol/ul), 2 μl relevant oligo 3 (10 pmol/ul), 2 μl H$_2$O. (See table V, below).

TABLE V

| Experiment | Oligo 1 ($^{32}$P-labelled) | Oligo 2 | Oligo 3 |
|---|---|---|---|
| S | Ah 5 | Ah 6 | Ah 7 |
| T | Ah 14 | Ah 6 | Ah 7 |

Anneal as described above. Add 1 μl 100 mM TSAT. Incubate at 25° C. for about 1.5 h, and then analyze by 10% urea polyacrylamide gel electrophoresis.

The results are shown FIG. 5.

Example 6

Mix 2 μl bufferA, B or D, 1 μl relevant oligo 1 (2 pmol/ul), 1 μl relevant oligo 2 (10 pmol/ul), 1 μl relevant oligo 3 (10 pmol/ul), 5 μl H$_2$O. (See table VI, below).

TABLE VI

| Experiment | Oligo 1 ($^{32}$P-labelled) | Oligo 2 | Oligo 3 |
|---|---|---|---|
| U$_A$(Buffer A) | Ah 23 | Ah 27 | Ah 28 |
| V$_A$(Buffer A) | Ah 23 | Ah 27 | None |
| U$_B$(Buffer B) | Ah 23 | Ah 27 | Ah 28 |
| V$_B$(Buffer B) | Ah 23 | Ah 27 | None |
| X (Buffer D) | Ah 24 | Ah 27 | Ah 28 |
| Y (Buffer D) | Ah 24 | Ah 27 | None |

Anneal as described above. Experiment U and V is added 1 μl 100 mM EDC and 1 μl 100 mM NHS, incubated for about 1 h at 24° C., and then added 2 μl buffer C, then incubated for 30 minuttes at 24° C. Experiment X and Y is added 2 μl 50 mM TSAT. Incubate at 24° C. for about 1.5 h, and then analyzed by 10% urea polyacrylamide gel electrophoresis, as described above.

The results are shown in FIG. 6.

Example 7

Mix 2 μl first Buffer (See below), 1 μl Ah 23 (2 pmol/ul), 1 μl Ah 27 (10 pmol/ul), 1 μl Ah28 (10 pmol/ul), 5 μl H$_2$O. Anneal as described above, then add 1 μl 100 mM NHS and 1 μl 1 M EDC, incubate for 30 minutes at 24° C., then add 3 μl second buffer (See below). Incubate for 40 minutes at 24° C., and then analyze by 10% urea polyacrylamide gel electrophoresis.

TABLE VII

| Experiments | First Buffer | Second Buffer |
|---|---|---|
| 7-1 | Buffer A | Buffer A |
| 7-2 | Buffer A | Buffer C |
| 7-3 | Buffer A | Buffer D |
| 7-4 | Buffer B | Buffer D |
| 7-5 | Buffer B | Buffer C |

Figure 7:
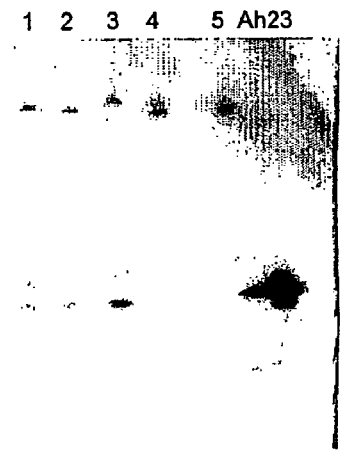
FIG. 7 shows a reproduction of a PAGE gel displaying cross-linking efficiency at pH 10.

The results are shown in FIG. 7.

Example 8

Mix 8-1: Mix 2 μl buffer B, 5 μl Ah36 (0.4 pmol/ul), 1 μl Ah37 (2 pmol/ul), 1 μl Ah38 (2 pmol/ul), 1 μl H$_2$O.

Mix 8-2: Mix 2 μl buffer B, 5 μl Ah36 (0.4 pmol/ul), 1 μl Ah37 (2 pmol/ul), 2 μl H$_2$O. Anneal by heating to 80° C., then cool to 44° C. (−2° C./30 sek).

Add 1 μl 100 mM NHS and 1 μl 1 M EDC. Incubate at indicated temperatures (see below) for 45 minutes, then add 2 μl Buffer D. Incubate for about 2 h, and then analyze by 10% urea polyacrylamide gel electrophoresis.

Incubation temperatures:
45° C., 48.2° C., 53.0° C., 58.5° C., 63.1° C., 65.6° C.

Figure 8:
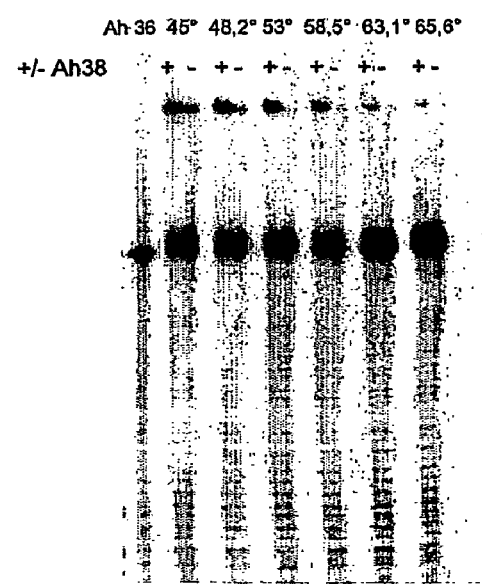
FIG. 8 shows a reproduction of a PAGE gel analysing the effect of absence of template when a 10 mer zipper box is used.

The results are shown in FIG. 8.

Example 9

Mix 9-1: Mix 2 μl buffer B, 1 μl Ah36 (2 pmol/ul), 1 μl Ah51 (2 pmol/ul), 1 μl Ah38(2 pmol/ul), 5 μl H$_2$O.

Mix 9-2: Mix 2 μl buffer B, 1 μl Ah36 (2 pmol/ul), 1 μl Ah51 (2 pmol/ul), 6 μl H$_2$O Anneal by heating to 80° C., then cool to 35° C. (−2° C./30 sek)(For temperatures 1 to 6), or heat to 80° C., then cool to 15° C. (−2° C./30 sek)(For temperatures 7 to 12).

Add 1 μl 100 mM NHS and 1 μl 1 M EDC. Incubate at indicated temperatures (see below) for 1 h, then add 2 μl Buffer D. Incubate for 1 h, and then analyze by 10% urea polyacrylamide gel electrophoresis, as described above.

Incubation temperatures:
1) 34.9° C., 2) 36.3° C., 3) 40.3° C., 4) 45.7° C., 5) 51.0° C., 6) 55.77, 7) 14.9° C., 8) 17.8° C., 9) 22.7° C., 10) 28.3° C., 11) 31.0° C., 12) 36° C.

Mix 9-3: Mix 2 μl buffer B, 0.5 μl Ah36 (2 pmol/ul), 1 μl Ah51 (2 pmol/ul), 1 μl Ah38(2 pmol/ul), 5.5 μl H$_2$O Mix 9-4: Mix 2 μl buffer B, 0.5 μl Ah36 (2 pmol/ul), 1 μl Ah51 (2 pmol/ul), 6.5 μl H$_2$O Anneal by heat at 80° C. then cool to 5° C. (−2° C./30 sek).

Add 1 μl 100 mM NHS and 1 μl 1 M EDC. Incubate at different temperatures (see below) for 1 h, then add 2 μl Buffer D. Incubate for 1 h, and then analyze by 10% urea polyacrylamide gel electrophoresis.

Incubation temperatures:
1) 5.9° C., 2) 9.9° C., 3) 12.6° C., 4) 18.3° C., 5) 23.3° C., 6) 27.9° C. 7) 35.6° C., 8) 45.9° C.

Figure 9A:
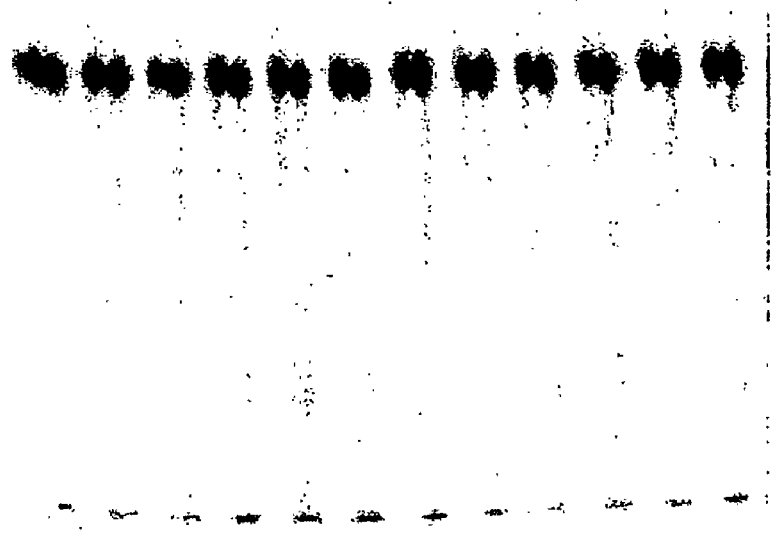
FIG. 9 shows a reproduction of a PAGE gel analysing the effect higher incubation temperature on the cross-linking efficiency.
Figure 9B:

The results are shown in FIG. 9, A and B.

Example 10

Mix 2 μl bufferA, 1 μl relevant oligo 1 (2 pmol/ul), 1 μl relevant oligo 2 (10 pmol/ul), 1 μl relevant oligo 3 (10 pmol/ul), 5 μl H$_2$O. (See table below). Anneal as described above.

Add 1 μl 100 mM NHS and 1 μl 1 M EDC. Incubate at different temperatures 1) 7.7° C., 2) 15.4° C., 3) 21.0° C. 4) 26.2° C. for about 2 h, and 5) 10° C. for 1 sec. and then 35° C. for 1 sec. Repeat 99 times. Analyze by 10% urea polyacrylamide gel electrophoresis.

TABLE VIII

| Experiment | Oligo 1 ($^{32}$P) | Oligo 2 | Oligo 3 |
|---|---|---|---|
| 10-1 | Ah 36 | None | Ah 38 |
| 10-2 | Ah 36 | None | None |
| 10-3 | Ah 36 | Ah 51 | Ah 38 |
| 10-4 | Ah 36 | Ah 51 | None |
| 10-5 | Ah 36 | Ah 67 | Ah 38 |
| 10-6 | Ah 36 | Ah 67 | None |
| 10-7 | Ah 36 | Ah 69 | Ah 38 |
| 10-8 | Ah 36 | Ah 69 | None |

Figure 10A:
FIG. 10 shows an image of a PAGE gel displaying the effect of a 5 mer zipper box on the cross-linking efficiency.
Figure 10B:
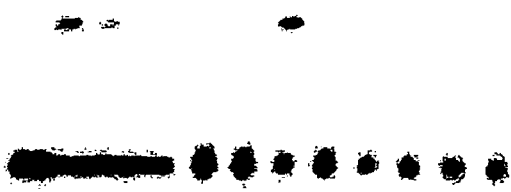

The results are shown in FIG. 10A and FIG. 10B.

Example 11

Mix 2.5 μl buffer A, 1 μl relevant oligo 1 (2 pmol/ul), 1 μl relevant oligo 2 (10 pmol/ul), 1 μl relevant oligo 3 (10 pmol/ul), 4.5 μl H$_2$O. (See table below). Anneal by heating to 80° C. and then cool to 30° C. or 55° C. Add 1 μl 100 mM NHS and 1 μl 1 M EDC. Incubate at 30° C. or 55° C. Then analyze by 10% urea polyacrylamide gel electrophoresis.

TABLE IX

| Experiment | Oligo 1 ($^{32}$P-labelled) | Oligo 2 | Oligo 3 |
|---|---|---|---|
| 11-1 | Ah 36 | Ah 37 | Ah 38 |
| 11-2 | Ah 36 | Ah 37 | None |
| 11-3 | Ah 65 | Ah 66 | Ah 38 |
| 11-4 | Ah 65 | Ah 66 | None |

TABLE IX-continued

| Experiment | Oligo 1 ($^{32}$P-labelled) | Oligo 2 | Oligo 3 |
| --- | --- | --- | --- |
| 11-5 | Ah 36 | Ah 66 | Ah 38 |
| 11-6 | Ah 36 | Ah 66 | None |
| 11-7 | Ah 65 | Ah 37 | Ah 38 |
| 11-8 | Ah 65 | Ah 37 | None |

Figure 11:
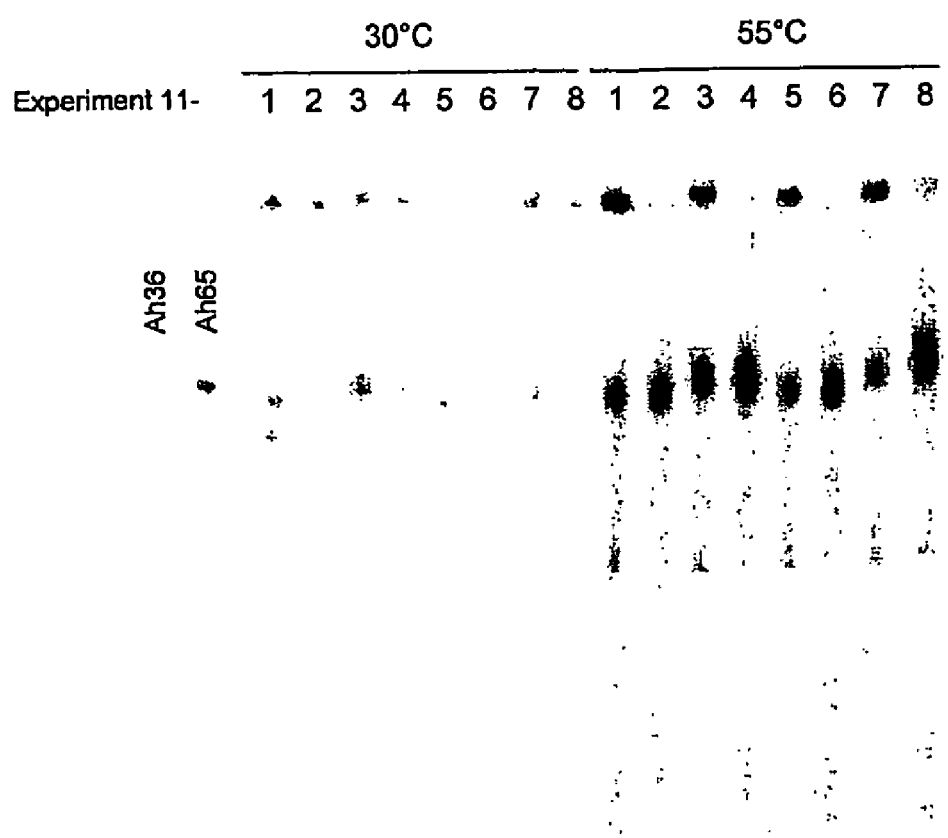
FIG. 11 shows an image of a PAGE gel displaying the effect of different temparatures on the cross-linking efficiency when a 10 mer zipper box is used.

The results are shown in FIG. 11.

Discussion of the Results of the Examples 1 to 11

Influence of Linker Length and Spacing Between the Reactive Groups on Cross-linking Efficiency.

We first examined the effect of changing the length of the linker that connects the amine and the nucleotide. Oligos Ah3 and Ah5 contain an amine separated from the base of the nucleotide by seven and eleven bonds, respectively (called amino modifier C2 dT and amino modifier C6 dT, see formulae above). These oligos were annealed immediately next to oligo Ah 4 or Ah6 (carrying amino modifier C2 dT and amino modifier C6 dT, respectively), i.e., with a spacing between the two oligos of 0 base pairs.

As seen in FIG. 1, lanes A and B, the efficiency of cross-linking is approximately equal for either amino modifier.

In all the following experiments, the oligo Ah5 (containing amino modifier C6 dT) was used as the reactive group amine.

Next, the two oligos were annealed to templates with spacings of 0, 1, 2, and 30 base pairs between the two oligos, and the efficiency of cross-linking examined. First, cross-linking using TSAT (Tris-succinimidyl aminotriacetate, Pierce cat#33063 dissolved in DMSO) was investigated. When oligos Ah5 and Ah6 were used, the efficiency of the cross-linking reaction were highest with a spacing of 0 base pairs (FIG. 1, lanes B; FIG. 2, panel H), less efficient with a spacing of 1 base pairs (FIG. 1, lanes D; FIG. 2, panel I), and very inefficient with spacings of 2 and 30 base pairs (FIG. 1, lanes E and F; FIG. 2, panel J and K).

Second, cross-linking of an amine and a carboxylic acid was examined. In this experiment, EDC (1-Ethyl-3-(3-dimethylaminopropyl) Carbodiimide Hydrochloride and NHS (N-Hydroxysuccinimide) was added in order to crosslink the two reactive groups. When oligos Ah1 and Ah6 were used, the efficiency of cross-linking was again highest for the shortest spacing of zero base pairs (FIG. 3, panel M), relatively high for a spacing of one base pairs (FIG. 3, panel N), and modest and insignificant for spacings of 2 and 30 base pairs, respectively (FIG. 3, panel O and P).

Optimization of TSAT and EDC Concentration.

The importance of TSAT concentration was tested by using the oligos Ah5 and Ah 6. A concentration of 1 or 10 mM TSAT leads to more efficient cross-linking than both 0.1 mM and 100 mM TSAT (FIGS. 1 and 2). The lower cross-linking efficiency obtained when using the highest TSAT concentration (100 mM) may be explained by two TSAT molecules reacting with each of the neighbouring amines.

Next, the importance of EDC concentration was examined for cross-linking an oligo carrying an amine (Ah6) and an oligo carrying a carboxylic acid (Ah1). Previously, it has been found that NHS concentrations of about 10 mM provides the highest cross-linking efficiency when used together with EDC. As shown in FIG. 3, 100 mM EDC results in the highest cross-linking efficiency when compared to 0.1 mM, 1 mM and 10 mM EDC.

Optimization of PH for TSAT and EDC/NHS Cross-linking Reactions.

Next, we tested the influence of different pH profiles for cross-linking efficiency using either the EDC/NHS or TSAT reagents.

Figure 12:
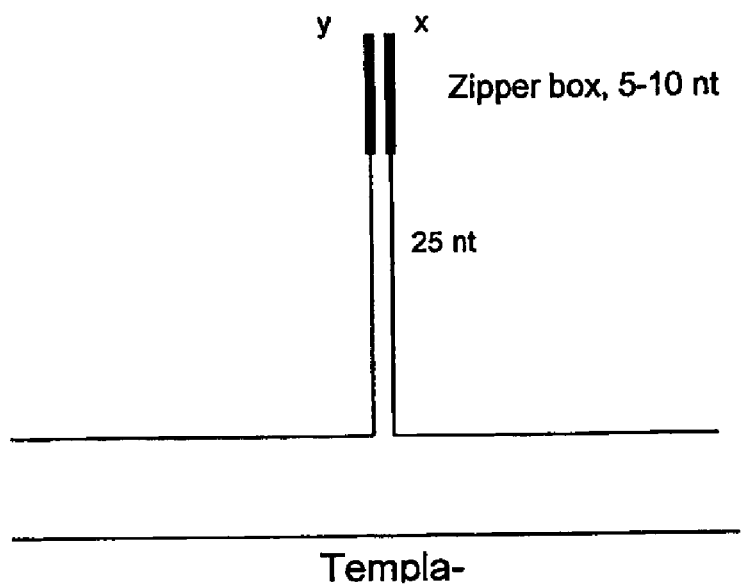
FIG. 12 shows a schematic drawing of the general principle used in the experimants.

A pH of 10 provides the most efficient TSAT cross-linking of two amines (FIG. 4, panel R; FIG. 5, panel S). Oligos Ah5 and Ah6 were used in this study. In experiment 6 (FIG. 6) a cross-linking efficiency of 80% is obtained using pH 10, and a spacing of zero base pairs between amine-carrying oligos Ah24 and Ah27. In other experiments where the linker that separates the complementing element (the region of the oligo that anneals to the template) and the reactive group (amine or carboxylic acid) is much larger (e.g. FIGS. 11 and 12), the cross-linking efficiency is much lower.

Oligos Ah1 and Ah6 were next used to examine the influence of different pH profiles on the the cross-linking efficiency using EDC/NHS. The constant pH that mediates the most efficient cross-linking is pH 7.5 (FIG. 4, panel Q). However, an even better cross-linking efficiency is obtained when the pH is initially kept at pH 6, and then increased to pH 9 (FIG. 6) or 10 (FIG. 7). In the latter two experiments, oligos Ah23 and Ah27 were used. Under those conditions, the cross-linking efficiency is almost 100%. Note, that in these experiments the linker that connects the reactive group and the complementing element is relatively short (e.g. 11 bonds for the Ah27).

Examination of Cross-linking Efficiency when Using a Zipper Box Sequence.

We next examined the cross-linking efficiency using oligos carrying reactive groups (amine or carboxylic acid) where the linker connecting the reactive group and the annealing region were approximately 25 nucleotides.

In a first experiment oligos Ah36 (carrying a carboxylic acid) and Ah67 (carrying an amine) were used. The template used (Ah38) anneals the two oligos immediately adjacent, i.e. with a spacing of zero base pairs.

Under the conditions of the experiment, less than 5% cross-linking efficiency is observed, and only at the highest tested temperature (FIG. 10, A and B, lanes 5). In order to improve the cross-linking efficiency, we introduced a so-called zipper box sequence at the 5'- and 3' end of oligos Ah67 and Ah36, respectively, the same termini that carries the reactive groups. The zipper-boxes are complementary sequences, and thus may bring the reactive groups of the two oligos into closer proximity. Two different lengths of zipper boxes were tested, namely a 10' mer zipper box (Ah37/Ah66, Ah37 forming a DNA duplex of 10 base pairs) and a 5' mer zipper box (forming a DNA duplex of 5 base pairs). See FIG. 12. Moreover, different designs of zipper boxes were tested, e.g. oligos in which the reactive group is attached immediately adjacent to the zipper box (Ah36, Ah37, Ah51), or placed two nucleotides upstream from the zipper box (Ah65, Ah66), or placed in the middle of the zipper box (Ah67).

We first tested the effect of the 5' mer zipper box on cross-linking efficiency. As can be seen, the 5' mer zipper box improves the cross-linking efficiency dramatically (FIG. 10, A and B, compare lanes 3 and lanes 5). Note that the template is absolutely required for cross-linking at all temperatures tested. The highest cross-linking efficiency is obtained when the temperature is cycled 99 times up and down between 10° C. and 35° C. (FIG. 10B). A high efficiency is also obtained when the temperature is kept constant at 21° C. or 26° C. (FIGS. 10A and B, lanes 3). The cross-linking efficiency does not improve further at temperatures above 26° C. (FIG. 9, A and B).

We next tested the efficiency of cross-linking in the 10' mer zipper box format. Oligos Ah36 and Ah37 were annealed to template Ah38, and the cross-linking efficiency examined at various temperatures. A surprisingly high degree of cross-linking in the absence of template was observed (FIG. 8, 45° C. and 48.2° C.). However, at temperatures above 58.5° C., no cross-linking is observed in the absence of template.

Next, the different locations of the reactive groups relative to the zipper box were tested. As shown in FIG. 10, A and B, lanes 7, the cross-linking efficiency decreases dramatically when one of the two reactive groups is located in the middle of the zipper box (i.e., the reactive group is attached to a nucleotide involved in DNA double helix formation; Ah67).

The location of the reactive groups relative to the zipper box was also tested in the context of the 10' mer zipper box. In this context, when both reactive groups are separated from the zipper box by two nucleotides (Ah65, Ah66), the efficiency of cross-linking is slightly decreased (FIG. 11, compare lanes 1 and 3). The cross-linking efficiency is not changed dramatically when different combinations of Ah65, Ah66, Ah36 and Ah37 are tested (i.e., when the reactive groups are placed immediately next to the zipper box, or two nucleotides upstream). Note that the template is not absolutely required at all temperatures in the context of the 10' mer zipper box. This template-independency is particularly pronounced at lower temperature (e.g., FIG. 11, 30° C.).

Example 12

Trisamine Scaffold Building Block

An oligo containing a modified nucleobase having a carboxylic acid moiety, was synthesised using the conventional phosphoramidite approach:

```
(SEQ ID NO )                                (SEQ ID NO: 24)
5'-GAC CTG TCG AGC ATC CAG CTT CAT GGG AAT TCC TCG
TCC ACA ATG XT
```

X was incorporated using the commercially available carboxy-dT phosphoramidite (10-1035-90 from Glen research). The underlined nucleobases represent the zipper region.

Schematic Representation of the Reaction:

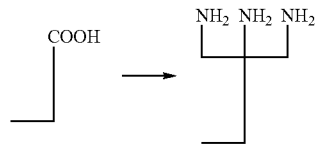

The oligo containing the modified nucleobase with a carboxylic acid moiety (1 nmol) was mixed with water (100 uL), hepes buffer (40 uL of a 200 mM, pH=7.5), NHS (20 uL of a 100 mM solution), EDC (20 uL of a freshly prepared 1 M solution) and tetrakis(aminomethyl)methane tetrahydrochloride (20 uL of a 100 mM solution). The reaction mixture was left o/n at room temperature. The volume was reduced to 60 uL by evaporation in vacuo. The pure oligo was obtained by addition of $NH_3$ conc. (20 uL) followed by HPLC purification. It was possible to isolate a peak after approximately 6 min using the following gradient: 0-3 minutes 100% A then 15% A and 85% B from 3-10 minutes then 100% B from 10-15 minutes then 100% A from 15-20 minutes. A=2% acetonitrile in 10 mM TEAA and B=80% acetonitrile in 10 mM TEAA.

Example 13

General Procedure for Attachment of a Functional Entity to a Thio Oligo

The following oligos containing a modified nucleobase, with a S-triphenylmethyl protected thio moiety, were synthesised using the conventional phosphoramidite approach:

```
(SEQ ID NO )                                (SEQ ID NO: 25)
5'-WCA TTG ACC TGT CTG CCB TGT CAG TCG GTA CTG TGG
TAA CGC GGA TCG ACC T (SEQ ID NO )                                (SEQ ID NO: 26)
5'-WCA TTG ACC TGA ACC ATG BTA AGC TGC CTG TCA GTC
GGT ACT ACG ACT ACG TTC AGG CAA GA
```

W was incorporated using the commercially available thiol modifier phosphoramidite (10-1926-90 from Glen research). B is an internal biotin incorporated using the commercially available phosphoramidite (10-1953-95 from Glen research). The nucleobases which are underlined indicates the zipper region.

The S-triphenylmethyl protected thio oligo (10 nmol) was evaporated in vacuo and resuspended in TEAA buffer (200 uL of a 0.1 M solution, pH=6.4). $AgNO_3$ (30 uL of a 1 M solution) was added and the mixture was left at room temperature for 1-2 hours. DTT (46 uL of a 1 M solution) was added and left for 5-10 minutes. The reaction mixture was spun down (20.000 G for 20 minutes) and the supernatant was collected. The solid was extracted with additional TEAA buffer (100 ul of a 0.1 M solution, pH=6.4). The pure thio oligo was obtained by conventional EtOH-precipitation.

Schematic representation of the loading reaction:

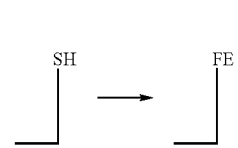

Each of the thio oligos (1 nmol) was dried in vacuo and treated with a chemical entity comprising the functional entity:

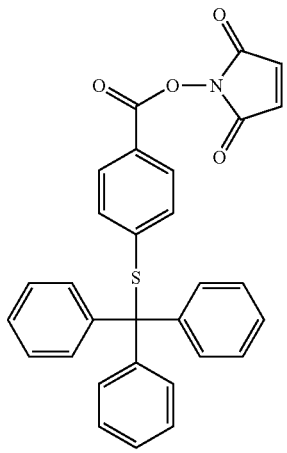

in dimethylformamide (50 ul of a 0.1 M solution) and left o/n at rt. The building block was spun down (20.000 G for 10 minutes) and the supernatant removed. Dimethylformamide (1 mL) was added and the building block was spun down (20.000 G for 10 minutes). The dimethylformamide was removed and the loaded thio oligo was resuspended in TEAA buffer (25 uL of a 0.1M solution, pH=6.4) and analysed by HPLC.

Example 14

Synthesis of a Encoded Scaffolded Molecule

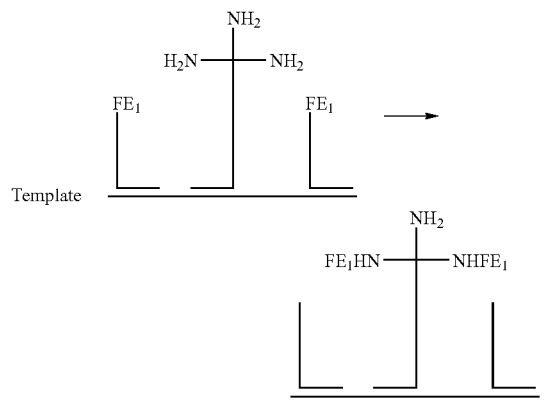

Figure 15:
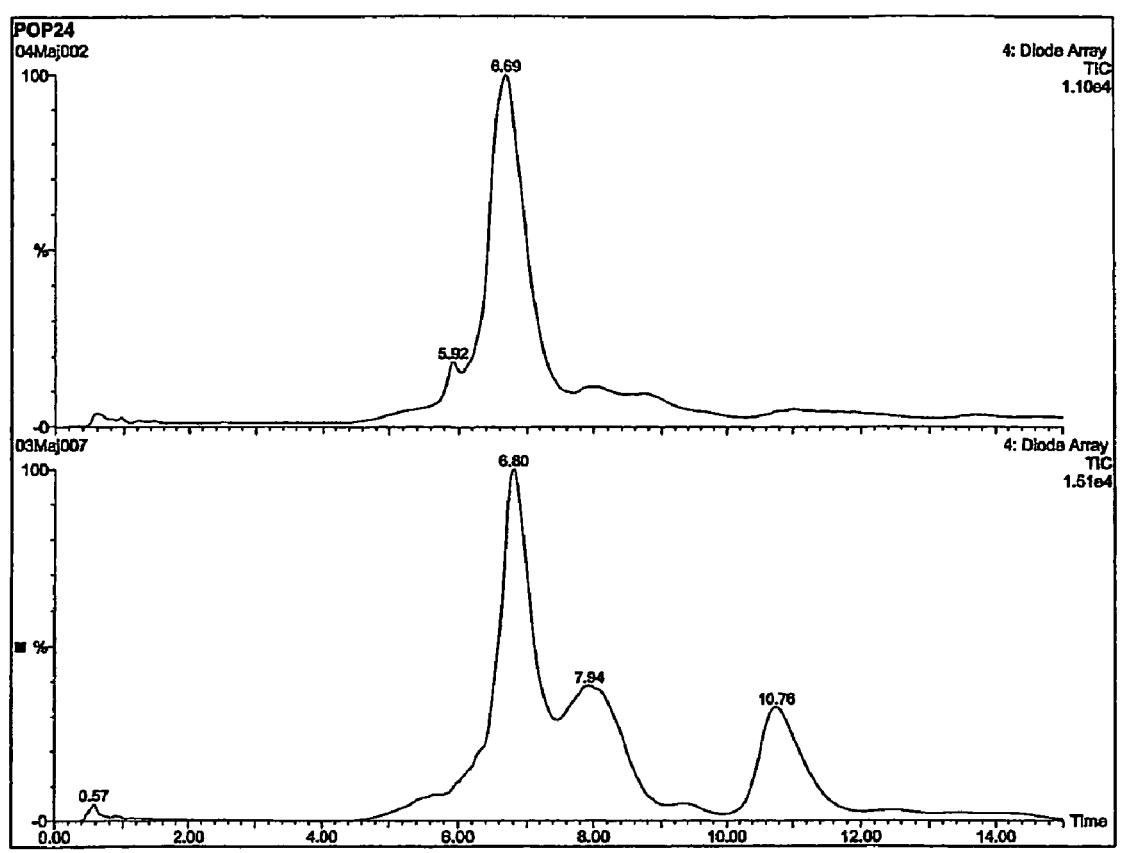
FIG. 15 shows a LC-chromatogram of the transfer of two identical functional entities to a scaffold molecule.

The template oligo 5'-BTCTTGCCTGAACGTAGTCG-TAGGTCGATCCGCGTTACCAGAGCTG-GATGCTCGACAGGTCCCGA TGCAATCCAGAGGTCG (SEQ ID NO 27) (1 nmol) was mixed with the two building blocks prepared in example 13 and with the scaffold building block prepared in example 12 (1 nmol) in hepes-buffer (20 uL of a 100 mM hepes and 1 M NaCl solution, pH=7.5) and water (added to a final volume of 100 uL). The building blocks were annealed to the template by heating to 50° C. and cooled (−2° C./30 second) to 30° C. The mixture was then left o/n at a fluctuating temperature (10° C. for 1 second then 35° C. for 1 second) The oligo complex was attached to streptavidine by addition of streptavidine beads (100 uL, prewashed with 2×1 mL 100 mM hepes buffer and iM NaCi, pH=7.5) The beads were washed with hepes buffer (1 mL) The trisamine scaffolded building block was separated from the streptavidine bound complex by addition of water (200 uL) followed by heating to 70° C. The water was transferred and evaporated in vacuo, resuspended in TEAA buffer (45 uL of a 0.1 M solution) and product formation analysed by HPLC (see FIG. 15).

The HPLC chromatogram shows the transfer of two functional entities to a scaffold building block. The top chromatogram shows the reference scaffold building block. The bottom chromatogram show the streptavidine purified scaffold building block after the partial transfer of one (peak at 7.94 minutes) and two (peak at 10.76 minutes) identical functional entities. The following gradient was used: 0-3 minutes 100% A, then 15% A and 85% B from 3-10 minutes, then 100% B from 10-15 minutes. A=2% acetonitrile in 10 mM TEAA and B=80% acetonitrile in 10 mM TEAA.

Due to the lipophilic nature of the functional entities a longer retention time, in the HPLC chromatogram, of the scaffolded molecule with two functional entities compared to one functional entity, was observed. The efficiency of the templated synthesis of a scaffolded molecule with the two identical functional entities was about 25% (peak at 10.76 minutes in FIG. 15).

General Methods and Materials for Examples 15 to 21:

In order to examine the reaction efficiency between two reactive groups, each coupled to a oligonucleotide, when the two oligos are annealed on the same template, the two set-ups shown in FIG. 16 was used (set-up A and set-up B). The two oligos contain terminal nucleotides derivatized with a carboxylic acid or an amine. After reaction ("cross-linking") of the reactive groups on the termini of the two oligos, the cross-linking efficiency may be analyzed by polyacrylamide gel electrophoresis, as the two oligos become coupled as a result of this cross-linking, and therefore migrate slower through the column DNA Oligos:

X=Carboxy-dT

Z=Amino Modifier C6

6=Amino-Modifier 5 cat. Nr. 10-1905

Zipper box sequences are underlined. Note that when the building block zipper boxes interact with zipper boxes in the template, the length of the zipper box duplex is one nucleotide longer than is underlined.

```
AH36:                                    (SEQ ID NO: 11)
5'-CGACCTCTGGATTGCATCGGTCATGGCTGACTGTCCGTCGAATGTGT
CCAGTTACX

AH51:                                    (SEQ ID NO: 13)
5'-ZGTAACACCTGTGTAAGCTGCCTGTCAGTCGGTACTGACCTGTCGAG
CATCCAGCT

AH82:                                    (SEQ ID NO: 28)
5'-ZGTAACACCTGGACCTGTCGAGCATCCAGCT

AH 201:                                  (SEQ ID NO: 29)
5'-TCTGGATTGCATCGGGAGTTACX

AH133:                                   (SEQ ID NO: 30)
5'-ZGTAACTCCTGTGTAAGCTGCCTGTCAGTCGGTACTGACCTGTCGAG
CATCCAGCT

AH134:                                   (SEQ ID NO: 31)
5'-ZGTAACTGCTGTGTAAGCTGCCTGTCAGTCGGTACTGACCTGTCGAG
CATCCAGCT

AH135:                                   (SEQ ID NO: 32)
5'-ZGTAACTGGTGTGTAAGCTGCCTGTCAGTCGGTACTGACCTGTCGAG
CATCCAGCT

AH 142:                                  (SEQ ID NO: 33)
5'-CGACCTCTGGATTGCATCGGTCATTTTTTTTTTTTTTTTTTTGGC
TGACTGTCCGTCGAATGTGTCCAGTTACX

AH 156:                                  (SEQ ID NO: 34)
5'-ZGACCTGTCAGCATCCAGCT

AH 202:                                  (SEQ ID NO: 35)
5'-TCTGGATTGCATCGGGTTACX

AH 203:                                  (SEQ ID NO: 36)
5'-TCTGGATTGCATCGGTTTTX

AH 236:                                  (SEQ ID NO: 37)
5'-6GTAACACCTGGACCTGTCGAGCATCCAGCT

AH 240:                                  (SEQ ID NO: 38)
5'-CGACCTCTGGATTGCATCGGGCACGGTTACX

AH 249:                                  (SEQ ID NO: 39)
5'-ZCTGGACAGCTCGTAGGTCGTTTTTTTTTTT

AH 251:                                  (SEQ ID NO: 40)
5'-ZGACCTGTCGAGCATCCAGCT

AH 252:                                  (SEQ ID NO: 41)
5'-XGACCTGTCGAGCATCCAGCT
```

```
AH 255:                                      (SEQ ID NO: 42)
5'-CGACCTCTGGATTGCATCGGTGTTACZ

AH 258:                                      (SEQ ID NO: 43)
5'-ACGACTACGTTCAGGCAAGAGTTACZ

AH 260:                                      (SEQ ID NO: 44)
5'-XCTGGACAGCTCGTAGGTCGTTTTTTTTTT

AH 261:                                      (SEQ ID NO: 45)
5'-CGACCTCTGGATTGCATCGGZ

AH 262:                                      (SEQ ID NO: 46)
5'-CGACCTCTGGATTGCATCGGTTACZ

AH 270:                                      (SEQ ID NO: 47)
5'-6GTAACGACCTGTCGAGCATCCAGCT

AH 271:                                      (SEQ ID NO: 48)
5'-6GTAACTGGACCTGTCGAGCATCCAGCT

AH 272:                                      (SEQ ID NO: 49)
5'-ACGACTACGTTCAGGCAAGAGTTACX

AH 273:                                      (SEQ ID NO: 50)
5'-ACGACTACGTTCAGGCAAGAGCGTTACX

AH 274:                                      (SEQ ID NO: 51)
5'-ACGACTACGTTCAGGCAAGAGCACGGTTACX

AH 275:                                      (SEQ ID NO: 52)
5'-CGACCTCTGGATTGCATCGGGCGTTACX

AH 276:                                      (SEQ ID NO: 53)
5'-CTGGTAACGCGGATCGACCTGCACGGTTACX

AH 277:                                      (SEQ ID NO: 54)
5'-CTGGTAACGCGGATCGACCTGCGTTACX
```

The oligonucleotides were prepared following the conventional phosphoramidite approach. X represents the commercially available carboxy-dT phosphoramidite (10-1035-90 from Glen research). Z represents amino modifier C6 dT (10-1039-from Glen Research). 6 represents the amino-modifier 5 (10-1905 from Glen Research)

Templates:

Zipper box sequences are underlined.

```
AH38:                                        (SEQ ID NO: 19)
5'-AGCTGGATGCTCGACAGGTCCCGATGCAATCCAGAGGTCG

AH140:                                       (SEQ ID NO: 55)
5'-AGCTGGATGCTCGACAGGTCAGGTCGATCCGCGTTACCAGTCTTGCC
TGAACGTAGTCGTCCGATGCAATCCAGAGGTCG

AH 154:                                      (SEQ ID NO: 56)
5'-AGCTGGATGCTCGACAGGTCA
AGTAACAGGTCGATCCGCGTTACCAGTCT
TGCCTGAACGTAGTCGTCCGATGCAATCCAGAGGTCG

AH 250:                                      (SEQ ID NO: 57)
5'-CGACCTACGAGCTGTCCAGAAGTAACAGGTCGATCC

AH 256:                                      (SEQ ID NO: 58)
5'-AGCTGGATGCTCGACAGGTCA
AGTAACACCAGGTCGATCCGCGTTACCAG
TCTTGCCTGAACGTAGTCGTCCGATGCAATCCAGAGGTCG

AH 263:                                      (SEQ ID NO: 59)
5'-CGACCTACGAGCTGTCCAGA
AGTAACAGGTCGATCCGCGTTACCAGTCTT
GCCTGAACGTAGTCGTCTGGTCACGTGGATCCTTGA

AH 278:                                      (SEQ ID NO: 60)
5'-AGCTGGATGCTCGACAGGTCGAGGTCGATCCGCGTTACCAGTCTTGC
CTGAACGTAGTCGTCCGATGCAATCCAGAGGTCG

AH 279:                                      (SEQ ID NO: 61)
5'-CGACCTACGAGCTGTCCAGA
AGTAACTTTTTTTTTTTTTTTTTTTTTTT
TTTTTTTTTTTTTTCTGGTCACGTGGATCCTTGA
```

The templates were prepared by conventional phosphoramidite synthesis.

Buffers:

Buffer A (100 mM Hepes pH=7.5; 1 M NaCl)

Buffer B (20 mM Hepes pH=7.5; 200 mM NaCl)

5'-Labeling with $^{32}$P.

Mix 5 pmol oligonucleotide, 2 µl 10× phosphorylation buffer (Promega cat#4103), 1 µl T4 Polynucleotide Kinase (Promega cat#4103), 1 µl γ-$^{32}$P ATP, add H$_2$O to 20 µl. Incubate at 37° C., 10-30 minutes.

PAGE (Polyacrylamide Gel Electrophoresis).

The samples are mixed with formamide dye 1:1 (98% formamide, 10 mM EDTA, pH 8, 0.025% Xylene Cyanol, 0.025% Bromphenol Blue), incubated at 80° C. for 2 minutes, and run on a denaturing 10% polyacrylamide gel. Develop gel using autoradiography (Kodak, BioMax film).

Example 15

In order to examine the effects of concentration on annealing efficiency, reaction efficiency and template dependency in the context of Set-up B, we did the following experiment, which included i) annealing and reaction at high building block and template concentration (experiments A and B), ii) annealing at high concentrations, followed by a 100-fold dilution and reaction at this low concentration (E and F), and iii) annealing and reaction at low concentrations (C and D). To examine the extent to which template-independent reactions occur, we also included a control complex, consisting of a competitor template and a competitor oligo carrying a reactive group (an amine).

Experimental.

Mix 10 µl Buffer A, relevant oligos in various concentrations (See table X, below), and add H$_2$O to 50 µl.

TABLE X

| Experiment | Oligo 1 ($^{32}$P-labelled) (BB1) | Oligo 2 (BB0) | Oligo 3 (Template) | Oligo 4 (Competitor oligo) | Oligo 5 (Competitor template) |
|---|---|---|---|---|---|
| A | Ah 202 (1 pmol) | Ah 156 (5 pmol) | Ah 154 (5 pmol) | Ah 249 (500 pmol) | Ah 250 (500 pmol) |
| B | Ah 202 (1 pmol) | Ah 156 (5 pmol) | Ah 154 (5 pmol) | Ah 249 (500 pmol) | |
| C | Ah 202 (0.01 pmol) | Ah 251 (0.05 pmol) | Ah 256 (0.05 pmol) | Ah 249 (5 pmol) | Ah 257 (5 pmol) |
| D | Ah 202 (0.01 pmol) | Ah 251 (0.05 pmol) | Ah 256 (0.05 pmol) | Ah 249 (5 pmol) | |
| E | Ah 202 (1 pmol) | Ah 251 (5 pmol) | Ah 154 (5 pmol) | | |
| F | Ah 202 (1 pmol) | Ah 251 (5 pmol) | Ah 154 (5 pmol) | Ah 249 (500 pmol) | Ah 263 (500 pmol) |

Anneal from 80° C. to 20° C. (−1° C./30 sek) for A-D and from 80° C. to 20° C. (−1° C./1 min) for E and F. E and F is diluted 100 times after annealing in buffer B. Then add 5 µl 500 mM DMT-MM (Prepared according to Kunishima et al.

Tetrahedron (2001), 57, 1551) dissolved in H$_2$O. Incubate at various temperatures o/n, then analyze by 10% urea polyacrylamide gel electrophoresis.

Figure 17:
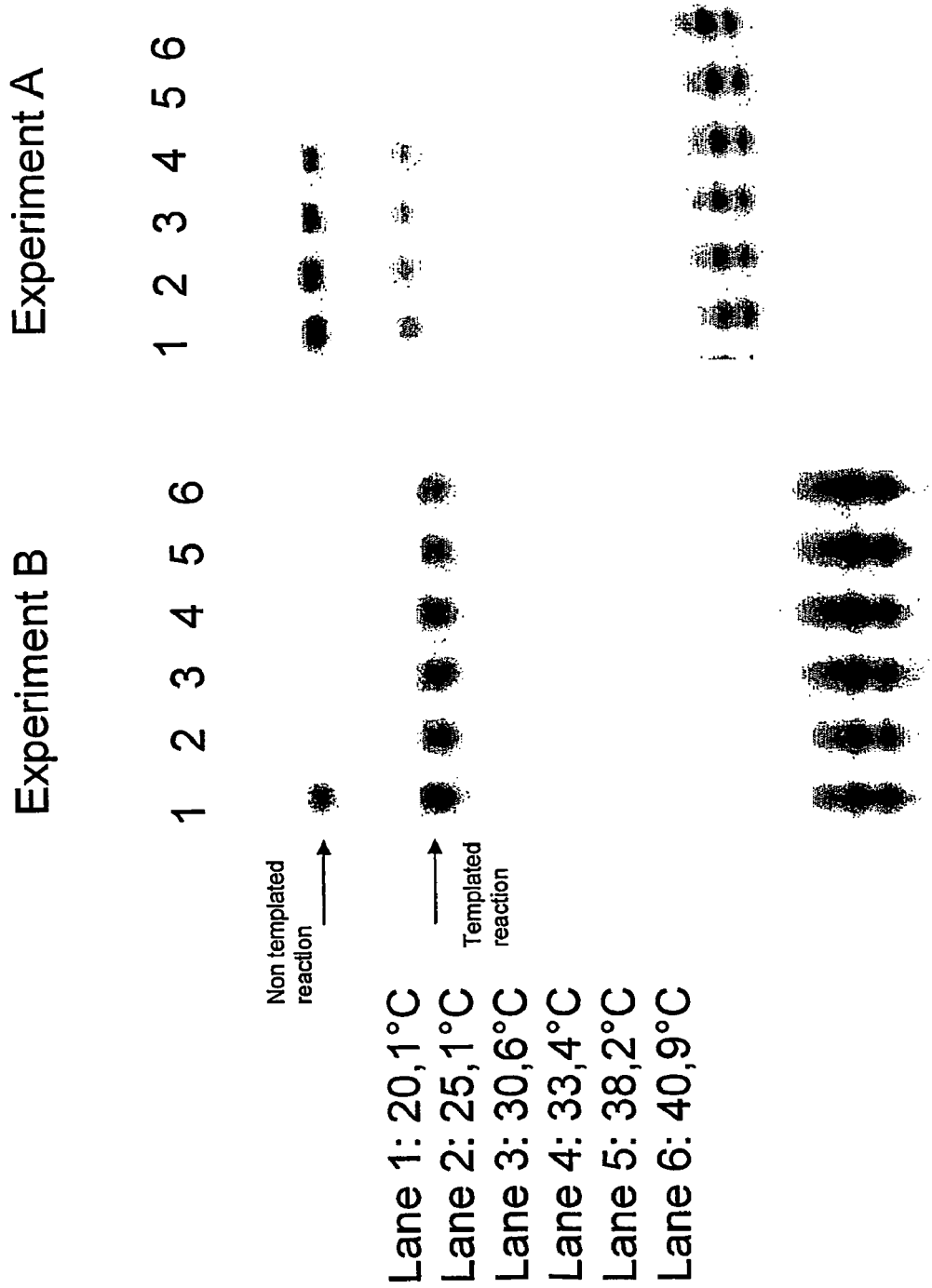
FIG. 17 shows the results of experiment A and B in example 15.
Figure 18:
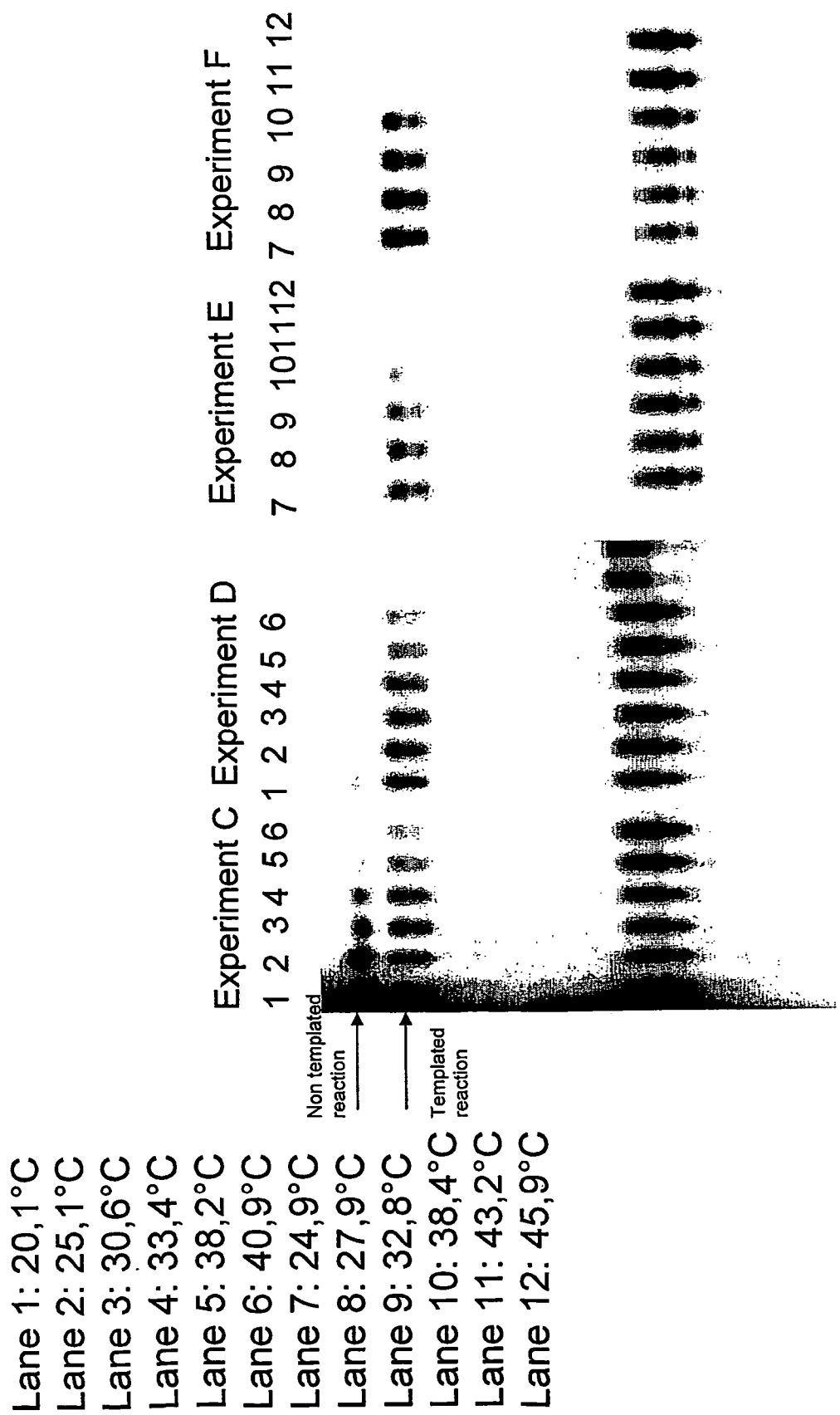
FIG. 18 shows the results of experiment D, E, and F reported in Example 16.

The results are shown in FIG. 17 (Experiment A and B) and FIG. 18 (Experiment C, D, E and F).

Conclusions:

A templated-independent reaction is often observed at 20° C. This artefact is presumably not mediated by the zipper box in the template, as it is observed even when the competitor template (carrying the zipper box) is not included in the incubation mixture (see e.g. FIG. 17, exp. B, lane 1). Annealing at a high concentration, followed by dilution and reaction at the resulting low concentration eliminates template independent reactions, but maintains efficient annealing of building block oligos at the template prior to the reaction step (compare the efficient cross-linking and the absence of template independent reaction of experiments E and F with the less attractive experiments A, B, C and D).

Example 16

In order to examine the effect of the zipper box in set-up B, when the building block is annealed at position 3, an experiment was performed using two different building block oligos, one of which has a 6-meric zipper box (six nucleotides of the building block oligo anneals to the complementary zipper box on the template), and one of which has no zipper box.

Experimental.

Mix 10 µl Buffer A, relevant oligos in various concentrations (See table 11, below), and add H$_2$O to 50 µl.

TABLE XI

| Experiment | Oligo 1 ($^{32}$P-labelled) (BB1) | Oligo 2 (BB0) | Oligo 3 (Template) | Oligo 4 (Competitor oligo) |
|---|---|---|---|---|
| A | Ah 202 (0.01 pmol) | Ah 156 (0.05 pmol) | Ah 256 (0.05 pmol) | Ah 249 (5 pmol) |
| B | Ah 261 (0.01 pmol) | Ah 252 (0.05 pmol) | Ah 256 (0.05 pmol) | Ah 260 (5 pmol) |

Anneal from 80° C. to 20° C. (–1° C./30 sek). Then add 5 ul 500 mM DMT-MM (Prepared according to Kunishima et al. Tetrahedron (2001), 57, 1551) dissolved in H$_2$O. Incubate at various temperatures o/n, then analyze by 10% urea polyacrylamide gel electrophoresis.

Figure 19:
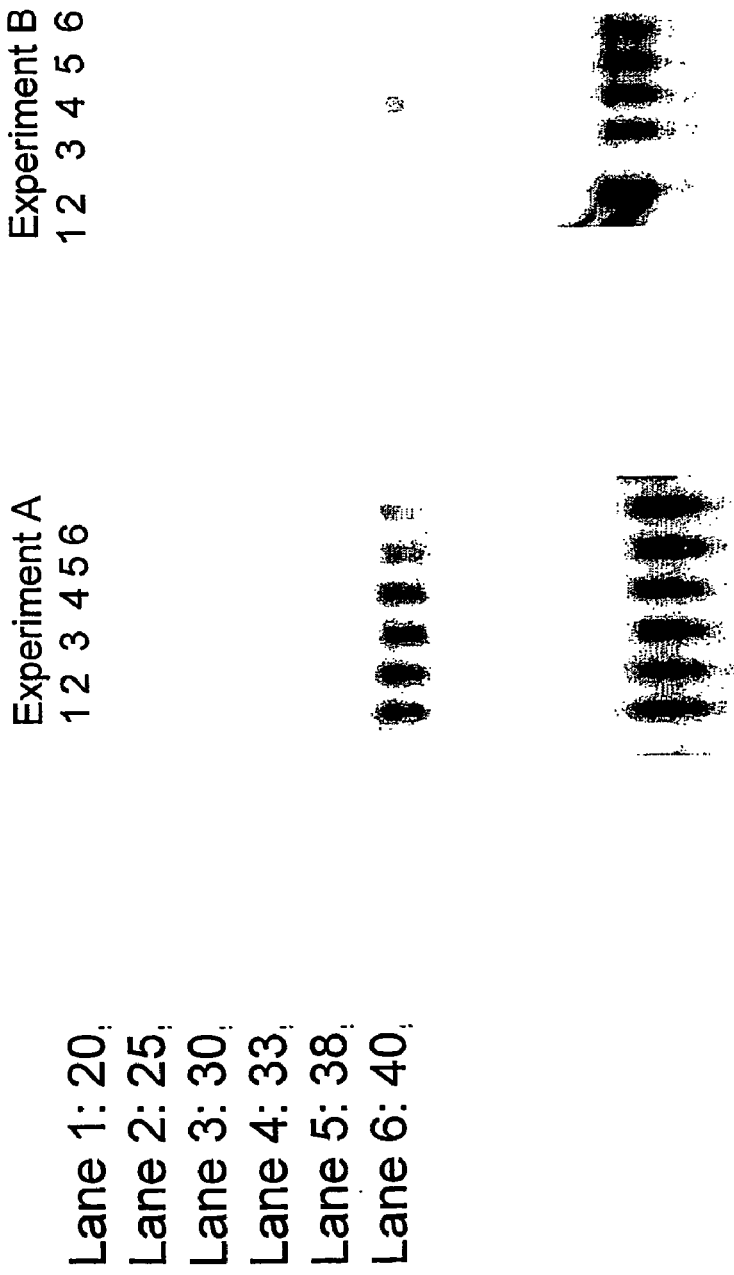
FIG. 19 discloses the results of experiment A and B reported in example 17.

The results are shown in FIG. 19.

Conclusion.

Experiment A employs a building block carrying a 6-meric zipper box, and a cross-linking efficiency of about 30% is observed (experiment A, lane 24). When a building block without a zipper box is employed (experiment B), no cross-linking is observed (the spot in lane 34 is an artefact on the film, and does not represent a cross-link). No cross-linking is observed, and even at 20° C. no reaction is observed (possibly because the building block does not carry a zipper box)

Example 17

We examined the cross-linking efficiency using zipper box lengths of 5, 6 or 7 nucleotides, in set-up B, using building blocks that anneal at position 3.

Experimental.

Mix 10 µl Buffer A, relevant oligos in various concentrations (See table XII, below), and add H$_2$O to 50 µl.

TABLE XII

| Experiment | Oligo 1 ($^{32}$P-labelled) (BB1) | Oligo 2 (BB0) | Oligo 3 (Template) | Oligo 4 (Competitor oligo) | Oligo 5 (Competitor template) |
|---|---|---|---|---|---|
| A | Ah 262 (1 pmol) | Ah 252 (5 pmol) | Ah 154 (5 pmol) | | |
| B | Ah 262 (1 pmol) | Ah 252 (5 pmol) | Ah 154 (5 pmol) | Ah 260 (500 pmol) | Ah 263 (500 pmol) |
| C | Ah 202 (1 pmol) | Ah 251 (5 pmol) | Ah 154 (5 pmol) | | |
| D | Ah 202 (1 pmol) | Ah 251 (5 pmol) | Ah 154 (5 pmol) | Ah 249 (500 pmol) | Ah 263 (500 pmol) |
| E | Ah 255 (1 pmol) | Ah 252 (5 pmol) | Ah 154 (5 pmol) | | |
| F | Ah 255 (1 pmol) | Ah 252 (5 pmol) | Ah 154 (5 pmol) | Ah 260 (500 pmol) | Ah 263 (500 pmol) |

Anneal from 80° C. to 20° C. (–1° C./min.). Dilute 100 times in buffer B+50 mM DMT-MM (Prepared according to Kunishima et al. Tetrahedron (2001), 57, 1551). Incubate at various temperatures o/n, then analyze by 10% urea polyacrylamide gel electrophoresis.

Figure 20:
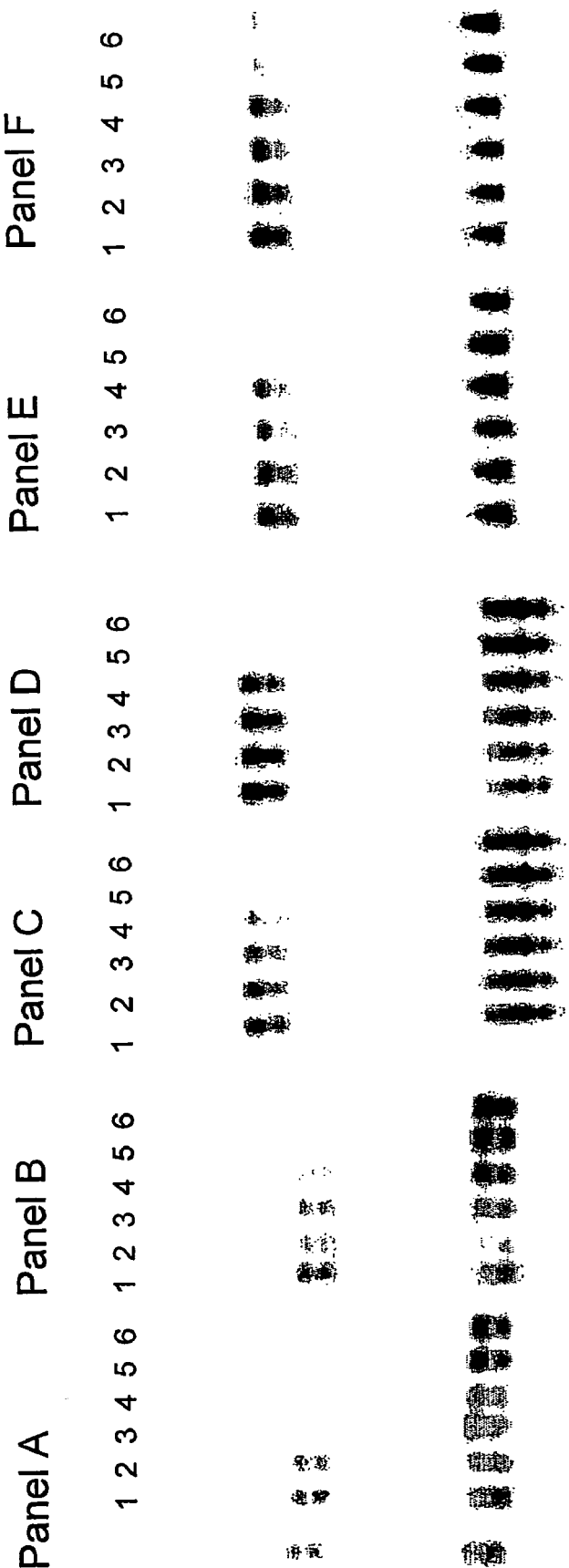
FIG. 20 discloses the results of example 17.

The results are shown in FIG. 20.

Conclusions.

Zipper boxes of length 5, 6 or 7 nucleotides mediate efficient cross-linking in the temperature range 24-28° C. (FIG. 20, Panel A, C, E). Under these conditions (where the annealing is at high concentration and the cross-linking at low concentration), no cross-linking to the competitor complex is observed (FIG. 20, Panel B, D and F).

Example 18

In this experiment we analyzed the cross-linking efficiency of various linker lengths in set-up A (the linker connects the anti-codon and the zipper box).

Experimental.

Mix 10 µl Buffer A, relevant oligos in various concentrations (See table XIII, below), and add H$_2$O to 50 µl.

TABLE XIII

| Experiment | Oligo 1 ($^{32}$P-labelled) (BB1) | Oligo 2 (BB0) | Oligo 3 (Template) |
|---|---|---|---|
| 1 | Ah 202 (1 pmol) | Ah 270 (10 pmol) | Ah 140 (5 pmol) |
| 2 | Ah 202 (1 pmol) | Ah 270 (10 pmol) | Ah 278 (5 pmol) |
| 3 | Ah 275 (1 pmol) | Ah 271 (10 pmol) | Ah 140 (5 pmol) |
| 4 | Ah 275 (1 pmol) | Ah 271 (10 pmol) | Ah 278 (5 pmol) |
| 5 | Ah 240 (1 pmol) | Ah 236 (10 pmol) | Ah 140 (5 pmol) |
| 6 | Ah 240 (1 pmol) | Ah 236 (10 pmol) | Ah 278 (5 pmol) |
| 7 | Ah 240 (1 pmol) | Ah 236 (10 pmol) | |
| 8 | Ah 272 (1 pmol) | Ah 270 (10 pmol) | Ah 140 (5 pmol) |
| 9 | Ah 272 (1 pmol) | Ah 270 (10 pmol) | Ah 278 (5 pmol) |
| 10 | Ah 273 (1 pmol) | Ah 271 (10 pmol) | Ah 140 (5 pmol) |
| 11 | Ah 273 (1 pmol) | Ah 271 (10 pmol) | Ah 278 (5 pmol) |
| 12 | Ah 274 (1 pmol) | Ah 236 (10 pmol) | Ah 140 (5 pmol) |

TABLE XIII-continued

| Experiment | Oligo 1 ($^{32}$P-labelled) (BB1) | Oligo 2 (BB0) | Oligo 3 (Template) |
|---|---|---|---|
| 13 | Ah 274 (1 pmol) | Ah 236 (10 pmol) | Ah 278 (5 pmol) |
| 14 | Ah 274 (1 pmol) | Ah 236 (10 pmol) | |
| 15 | Ah 155 (1 pmol) | Ah 270 (10 pmol) | Ah 140 (5 pmol) |
| 16 | Ah 155 (1 pmol) | Ah 270 (10 pmol) | Ah 278 (5 pmol) |
| 17 | Ah 277 (1 pmol) | Ah 271 (10 pmol) | Ah 140 (5 pmol) |
| 18 | Ah 277 (1 pmol) | Ah 271 (10 pmol) | Ah 278 (5 pmol) |
| 19 | Ah 276 (1 pmol) | Ah 236 (10 pmol) | Ah 140 (5 pmol) |
| 20 | Ah 276 (1 pmol) | Ah 236 (10 pmol) | Ah 278 (5 pmol) |
| 21 | Ah 276 (1 pmol) | Ah 236 (10 pmol) | |

Anneal from 80° C. to 200 C (−1° C./min.). Add 5 µl 500 mM DMT-MM (Prepared according to Kunishima et al. *Tetrahedron* (2001), 57, 1551). Incubate at 10° C. for 5 sec. and then 35° C. for 1 sec. Repeat o/n, then analyze by 10% urea polyacrylamide gel electrophoresis.

Figure 21:
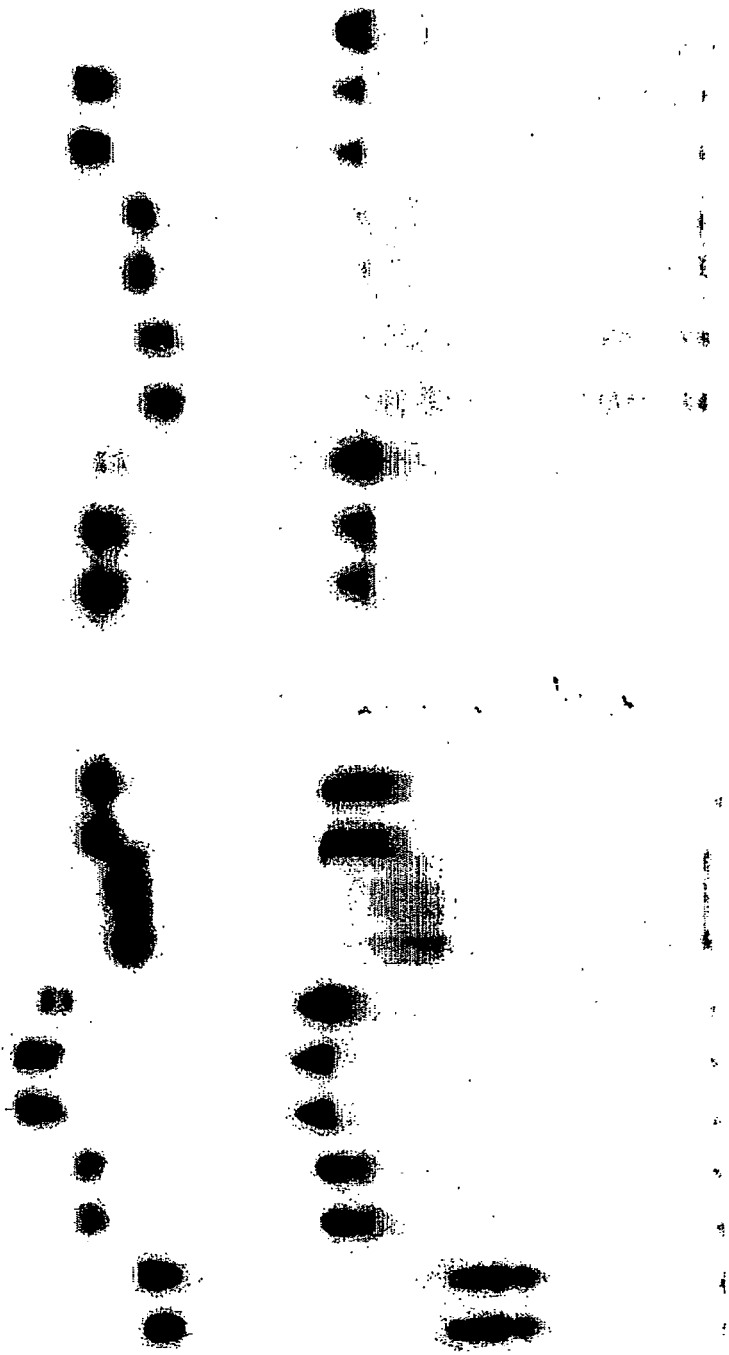
FIG. 21 shows the results of the experiments conducted in example 18.

The results are shown in FIG. 21.

Conclusions.

Two aspects are examined: i) The influence of linker length on cross-linking efficiency (linker lengths 0, 2, and 5 nucleotides are examined), ii) The importance of spacing between the two reacting building blocks. FIG. 21, Lanes 1-6 involve a building block oligo annealed to position 3; Lane 7 involves the same building block, however, no template is present in lane 7. Lanes 8-13 involve a building block oligo annealed to position 2; lane 14 involve the same building block oligo, however, no template is present. Lanes 15-20 involve a building block oligo annealed to position 1; lane 21 involve the same oligo, and no template is present. Lanes 1, 3, 5, 8, 10, 12, 15, 17, 19 uses templates where the spacing between the bound building block oligos is one nucleotide larger than the templates used in experiments of lane 2, 4, 6, 9, 11, 13, 16, 18, and 20.

The optimal linker length as regards cross-linking efficiency is 0 nucleotides at all positions (FIG. 21, lanes 1, 2 for position 3; lanes 8, 9 for position 2; lanes 15, 16 for position. Separations of 0 or 1 nucleotides between building blocks bound to position 1 and 0, has no effect on the efficiency of cross-linking between the two building blocks (FIG. 21, compare e.g. lanes 1 and 2). Very high efficiencies of cross-linking are observed, from all three positions. Using a zipper box of 5 nucleotides, the reaction efficiency is approximately 50%, 95% and 95% when the building block oligo is annealed at position 3, 2 and 1 respectively, and the linker length is 0 nucleotides (FIG. 21, lanes 1, 2 and 8, 9 and 15, 16).

Example 19

In this example, in experiments 5, 8, 14 and 17, we analyzed the cross-linking efficiency of various linker lengths in set-up B.

Experimental.

Mix 10 µl Buffer A, relevant oligos in various concentrations (See table XIV, below), and add H$_2$O to 50 µl.

TABLE XIV

| Experiment | Oligo 1 ($^{32}$P-labelled) (BB1) | Oligo 2 (BB0) | Oligo 3 (Template) |
|---|---|---|---|
| 1 | Ah 240 (5 pmol) | | |
| 2 | Ah 240 (5 pmol) | Ah 82 (10 pmol) | Ah 136 (10 pmol) |
| 3 | Ah 240 (5 pmol) | Ah 82 (10 pmol) | Ah 140 (10 pmol) |
| 4 | Ah 240 (5 pmol) | Ah 82 (10 pmol) | |
| 5 | Ah 240 (5 pmol) | Ah 156 (10 pmol) | Ah 154 (10 pmol) |
| 6 | Ah 240 (5 pmol) | Ah 156 (10 pmol) | |
| 7 | Ah 202 (5 pmol) | | |
| 8 | Ah 202 (5 pmol) | Ah 156 (10 pmol) | Ah 154 (10 pmol) |
| 9 | Ah 203 (5 pmol) | Ah 156 (10 pmol) | |
| 10 | Ah 203 (5 pmol) | | |
| 11 | Ah 203 (5 pmol) | Ah 156 (10 pmol) | Ah 154 (10 pmol) |
| 12 | Ah 203 (5 pmol) | Ah 156 (10 pmol) | |
| 13 | Ah 36 (5 pmol) | | |
| 14 | Ah 36 (5 pmol) | Ah 156 (10 pmol) | Ah 154 (10 pmol) |
| 15 | Ah 36 (5 pmol) | Ah 156 (10 pmol) | |
| 16 | Ah 142 (5 pmol) | | |
| 17 | Ah 142 (5 pmol) | Ah 156 (10 pmol) | Ah 154 (10 pmol) |
| 18 | Ah 142 (5 pmol) | Ah 156 (10 pmol) | |

Anneal from 80° C. to 20° C. (−1° C./min.). Add 5 µl 500 mM DMT-MM (Prepared according to Kunishima et al. *Tetrahedron* (2001), 57, 1551). Incubate at 10° C. for 5 sec. and then 35° C. for 1 sec. Repeat o/n, then analyze by 10% urea polyacrylamide gel electrophoresis.

Figure 22:
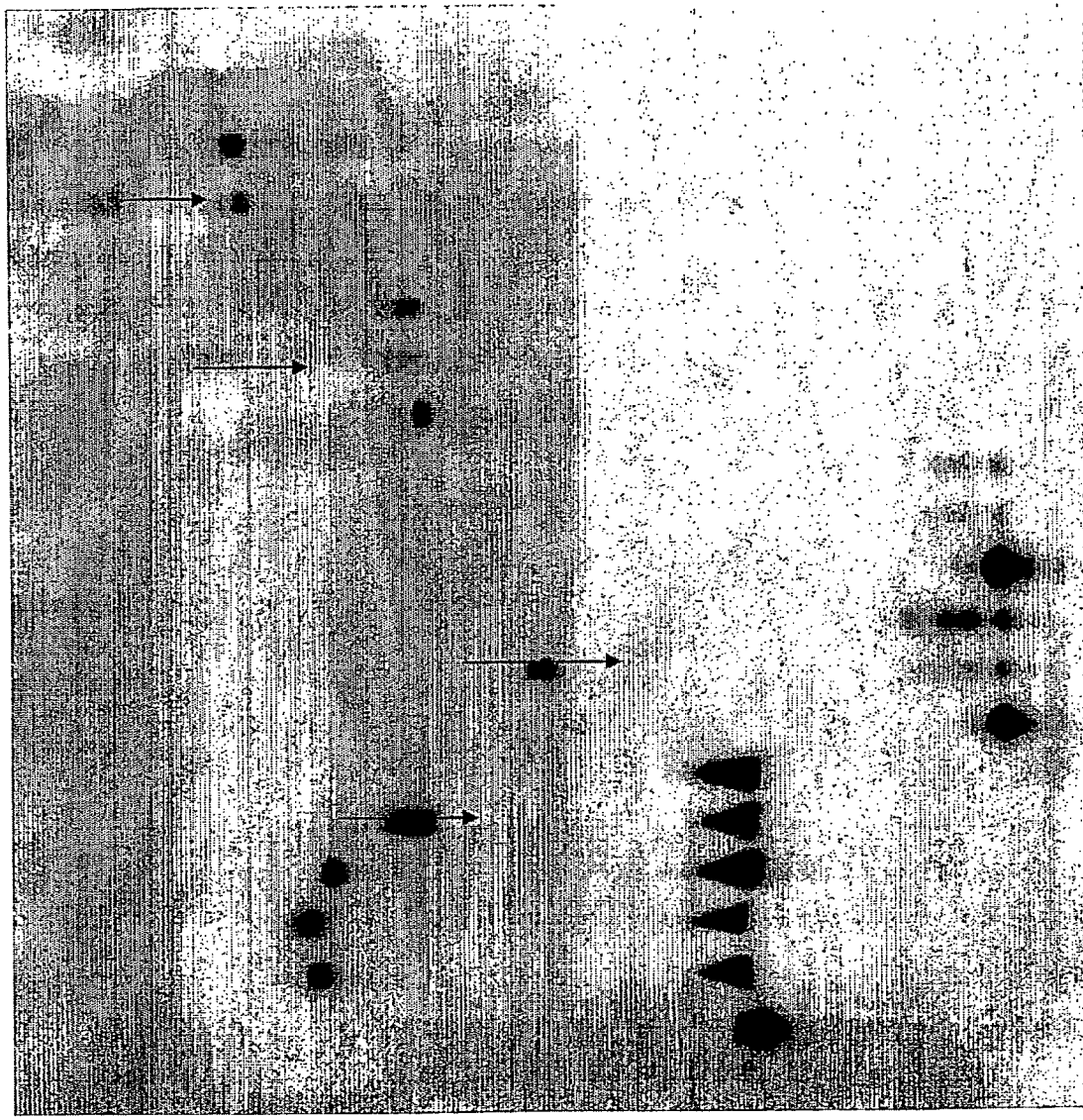
FIG. 22 shows the results of the experiments disclosed in example 19.

The results are shown in FIG. 22.

Conclusions.

The experiments measure reaction efficiency between a building block oligo bound at position 3 in the oligo setup B. Linker lengths of 0, 5, 30 and 50 nucleotides mediates reaction efficiencies of appr. 90% (lane 8), 50% (lane 5), 2040 % (lane 14) and 20-40 % (lane 17) respectively. In other words, a linker length of 0 nucleotides is optimal for set-up B, as was also observed for set-up A. In setup B reaction efficiencies from position 2 and position 1 of approximately 75% and 90% have been achieved (data not shown).

Example 20

We tested the extent of template-independent reactions at various temperatures, using zipper box lengths of 5, 6, 7, or 8 nucleotides, under conditions where template-independent reactions are observed (i.e., both annealing and reaction is done at high template and building block concentrations).

Experimental.

Mix 2 µl Buffer A, relevant oligos in various concentrations (See table XV, below), and add H$_2$O to 10 µl.

TABLE XV

| Experiment | Oligo 1 ($^{32}$P-labelled) (BB1) | Oligo 2 (BB0) | Oligo 3 (Template) |
|---|---|---|---|
| A | Ah 36 (2 pmol) | Ah 51 (10 pmol) | Ah 38 (10 pmol) |
| B | Ah 36 (2 pmol) | Ah 51 (10 pmol) | |
| C | Ah 36 (2 pmol) | Ah 133 (10 pmol) | Ah 38 (10 pmol) |
| D | Ah 36 (2 pmol) | Ah 133 (10 pmol) | |
| E | Ah 36 (2 pmol) | Ah 134 (10 pmol) | Ah 38 (10 pmol) |
| F | Ah 36 (2 pmol) | Ah 134 (10 pmol) | |
| G | Ah 36 (2 pmol) | Ah 135 (10 pmol) | Ah 38 (10 pmol) |
| H | Ah 36 (2 pmol) | Ah 135 (10 pmol) | |

Anneal from 80° C. to 20° C. (−1° C./min.). Add 1 µl 500 mM DMT-MM (Prepared according to Kunishima et al. *Tetrahedron* (2001), 57, 1551). Incubate at various temperatures o/n, then analyze by 10% urea polyacrylamide gel electrophoresis.

Figure 23:
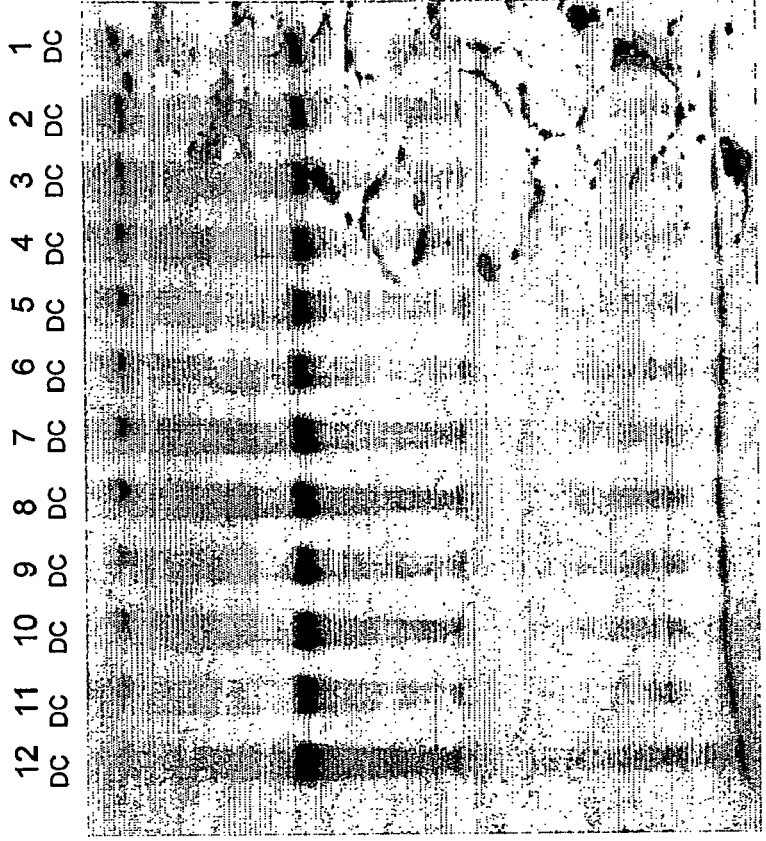
FIG. 23 shows the results of Experiments A to D reported in example 20.

The results are shown in FIG. 23 and 24.

TABLE XVI

| Experiment | Oligo 1 ($^{32}$P-labelled) (BB1) | Oligo 1+ | Oligo 2 (BB0) | Oligo 3 (Template) | Oligo 4 (Competitor Oligo) | Oligo 5 (Competitor template) |
|---|---|---|---|---|---|---|
| A | Ah 258 (1 pmol) | Ah 202 (10 pmol) | Ah 252 (10 pmol) | Ah 154 (5 pmol) | | |
| B | Ah 258 (1 pmol) | | Ah 252 (10 pmol) | Ah 154 (5 pmol) | | |
| C | Ah 258 (1 pmol) | Ah 202 (10 pmol) | Ah 252 (10 pmol) | Ah 154 (5 pmol) | Ah 260 (10 pmol) | Ah 279 (5 pmol) |
| D | Ah 258 (1 pmol) | | Ah 252 (10 pmol) | Ah 154 (5 pmol) | Ah 260 (10 pmol) | Ah 279 (5 pmol) |
| E | Ah 272 (1 pmol) | Ah 255 (10 pmol) | Ah 270 (10 pmol) | Ah 140 (5 pmol) | | |
| F | Ah 272 (1 pmol) | | Ah 270 (10 pmol) | Ah 140 (5 pmol) | | |

Conclusions:

Using a 5-meric zipper box (experiments A and B), no template-independent reaction is observed for temperatures between 9.9° C. and 50.8° C. (FIG. 23, lanes 1-12). Using a zipperbox of length 6, 7, or 8 nucleotides, a template-independent reaction is observed in the temperature range of 5-28° C., 5-32° C., and 5-35° C., respectively. When performing templated reactions that cannot be initiated by the experimenter (e.g. by addition of reagent), it is therefore recommended to perform annealing and reaction at a temperature that does not lead to template-independent reaction (e.g. 25° C., 30° C., 34° C., and 37° C. for zipper box lengths of 5-, 6-, 7-, and 8-nucleotides, respectively).

When performing reactions that can be initiated by the experimenter (e.g. by addition of reagent or UV-exposure) the complexes may be formed at lower temperatures, to ensure high degree of zipper box—zipper box complex formation, where after excess building block-oligos may be removed by washing, and then the reaction can be initiated. Because of the lower concentration of building block-oligos after the wash, the template-independent reaction will be much less significant.

Example 21

In a multistep procedure (where the building block-oligos are added to the template scaffold complex and reacted one at a time), it is important that the oligos (used in the previous step, and still bound to the template) do not interfere with the reaction of the last added building block-oligo.

We here examine whether the efficiency of cross-linking between building block oligos bound at position 2 and position 0 is affected by building block oligos bound at position 3, in both set-up A and B.

Experimental.

Mix 10 µl Buffer A, relevant oligos in various concentrations (See table XVI, below), and add H$_2$O to 50 µl.

Anneal from 80° C. to 30° C. (−1° C./min.) without BB1. Add BB1 and anneal again from 55° C. to 30° C. (−1° C./min). Dilute 100 times in buffer B +50 mM DMT-MM (Prepared according to Kunishima et al. *Tetrahedron* (2001), 57, 1551). Incubate at 30° C. o/n for A to D, and at 10° C. for 5 sec and then 35° C. for 1 sec repeat o/n for E and F, then analyze by 10% urea polyacrylamide gel electrophoresis.

Figure 25:
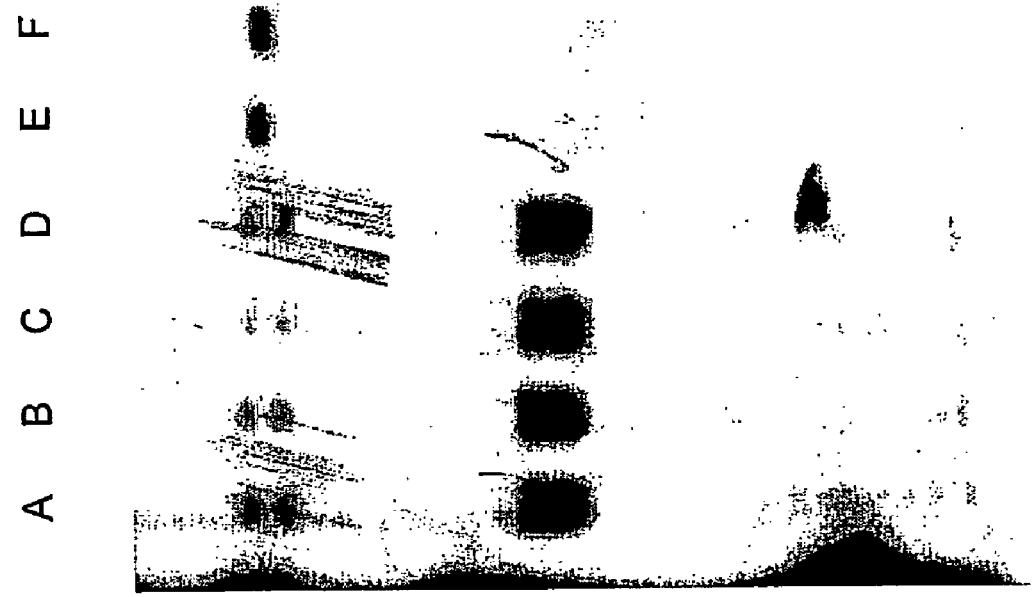
FIG. 25 shows the results of example 21.

The results are shown in FIG. 25.

Conclusions.

An occupied position 3 does not interfere with the cross-linking of building blocks bound at position 2 and 0 (FIG. 25, compare lane A with lane B, lane C with lane D, lane E with lane F).

The invention claimed is:

1. A method for synthesizing a templated molecule, comprising the steps of:
   a) providing at least one template comprising of one or more codons,
   b) providing a first functional entity attached to a first zipping oligonucleotide capable of reversible interaction with a second zipping oligonucleotide,
   c) providing one or more building blocks, each building block comprising a further functional entity linked to an anti-codon by a linker,
      wherein the anti-codon complements a codon of the template,
      wherein the further functional entity is connected to the second zipping oligonucleoticle capable of reversible interaction with the first zipping oligonucleotide attached to the first functional entity provided in step b), and
      wherein the further functional entity is capable of being chemically connected to the first functional entity provided in step b),
   d) contacting the components provided in steps a), b) and c) with each other under conditions allowing for i) specific hybridization of building block anti-codon(s) to the codon(s) of the template(s) and ii) dimerization of two zipping oligonucleotides attached to different functional entities,
   e) allowing a further functional entity of the one or more building blocks provided in step c) to form a chemical connection to the first functional entity provided in step b), and
   f) obtaining a templated molecule attached to the template which directed the synthesis thereof.

2. The method of claim 1, wherein steps d) and e) are repeated one or more times prior to obtaining in step f) the templated molecule attached to the template which directed the synthesis thereof.

3. The method of claim 1, wherein the first functional entity is covalently connected to the template.

4. The method of claim 1, wherein the first functional entity is hybridized to the template.

5. The method of claim 1, wherein the first functional entity forms part of a building block further comprising
   an anti-codon complementing a template codon,
   a linker connecting the anti-codon and the first functional entity, and
   a first zipping oligonucleotide connected to the first functional entity.

6. The method of claim 3, wherein the first functional entity forms part of a building block further comprising
   an anti-codon complementing a template codon,
   a linker connecting the anti-codon and the first functional entity, and
   a first zipping oligonucleotide connected to the first functional entity.

7. The method of claim 4, wherein the first functional entity forms part of a building block further comprising
   an anti-codon complementing a template codon,
   a linker connecting the anti-codon and the first functional entity, and
   a first zipping oligonucleotide connected to the first functional entity.

8. The method of claim 1, wherein the zipping oligonucleotide of the first functional entity is present in the template.

9. The method of claim 3, wherein the zipping oligonucleotide of the first functional entity is present in the template.

10. The method of claim 5, wherein the zipping oligonucleotide of the first functional entity is present in the template.

11. The method of claim 1, wherein the zipping oligonucleotides comprise complementary sequences of nucleic acids or nucleic acid analogs.

12. The method of claim 3, wherein the zipping oligonucleotides comprise complementary sequences of nucleic acids or nucleic acid analogs.

13. The method of claim 4, wherein the zipping oligonucleotides comprise complementary sequences of nucleic acids or nucleic acid analogs.

14. The method of claim 1, wherein the first functional entity is further connected to a sequence of nucleic acids complementing a sequence of nucleic acids harbored by the template.

15. The method of claim 3, wherein the first functional entity is further connected to a sequence of nucleic acids complementing a sequence of nucleic acids harbored by the template.

16. The method of claim 4, wherein the first functional entity is further connected to a sequence of nucleic acids complementing a sequence of nucleic acids harbored by the template.

17. The method of claim 1, wherein the zipping oligonucleotide forms part of the linker of the building block.

18. The method of claim 5, wherein the zipping oligonucleotide forms part of the linker of the building block.

19. The method of claim 8, wherein the zipping oligonucleotide is proximal to the functional entity.

20. The method of claim 17, wherein the zipping oligonucleotide is proximal to the functional entity.

21. The method of claim 17, wherein the zipping oligonucleotide is spaced from the first or further functional entity by no more than 2 nucleotides.

22. The method of claim 19, wherein the zipping oligonucleotide is spaced from the first or further functional entity by no more than 2 nucleotides.

23. The method of claim 21, wherein the zipping oligonucleotide and the first functional entity is spaced by no more than 2 nucleotides.

24. The method of claim 1, wherein the number of nucleotides which distance the first functional entity from the first zipping oligonucleotide is the same as the number of nucleotides which distance the further functional entity from the second zipping oligonucleotide.

25. The method of claim 1, wherein the zipping oligonucleotides comprise from 3 to 20 nucleotides.

26. The method of claim 25, wherein the zipping oligonucleotides comprise from 4 to 16 nucleotides.

27. The method of claim 26, wherein the zipping oligonucleotides comprise from 5 to 10 nucleotides.

28. The method of claim 1, wherein the linker in the building block between the anti-codon and the zipping oligonucleotide is a single bond.

29. The method of claim 5, wherein the linker in the building block between the anti-codon and the zipping oligonucleotide is a single bond.

30. The method of claim 1, wherein the hybridization of the building block anti-codon(s) to the template codons results in the formation of a codon:anti-codon hybrid, characterized by an annealing temperature, and the annealing temperature of the codon:anti-codon hybrid is higher than the annealing temperature of the hybridized zipping oligonucleotides.

31. The method of claim 30, wherein the difference between the annealing temperatures is 10° C. or more.

32. The method of claim 30, wherein the difference between the annealing temperatures is 25° C. or more.

33. The method of claim 1, wherein the conditions for allowing specific hybridization of the building block anticodon(s) to the codon(s) of the template(s) are distinct from the conditions allowing for optimal dimerisation of the two zipping oligonucleotides.

34. The method of claim 33, wherein the conditions for allowing specific hybridization of the building block anticodon(s) to the codon(s) of the template include a concentration of codons and/or anticodons, which is higher than the concentration of codons and/or anticodons used for dimerisation of the two zipping oligonucleotides.

35. The method of claim 34, wherein the concentration during hybridization of codon(s) and anti-codons is at least 10 times higher than the concentration used for dimerisation of the two zipping oligonucleotides.

36. The method of claim 1, wherein the contacting according to step d) is performed by alternating the temperature below and above the annealing temperature of the hybridized zipping oligonucleotides.

37. The method of claim 36, wherein a plurality of temperature alternations are performed.

38. The method of claim 36, wherein the highest temperature is below the annealing temperature of the codon:anticodon hybrid.

39. The method of claim 1, wherein the template codons have from 3 to 30 nucleotides.

40. The method of claim 1, wherein at least two codons of the template are arranged in sequence next to each other and are separated by a spacer group.

41. The method of claim 40, wherein the template comprises further codons.

42. The method of claim 41, wherein each further codon is separated by a spacer nucleotide sequence.

43. The method of claim 40, wherein each spacer nucleotide sequence identifies the position of a corresponding codon.

44. The method of claim 40, wherein the spacer nucleotide sequence contains a region of high affinity ensuring that the hybridization of the template with the anti-codon(s) occur in frame.

45. The method of claim 40, wherein the spacer nucleotide sequence adjusts the codon:anti-codon annealing temperature.

46. The method of claim 1, wherein the number of template codons is from 2 to 100.

47. The method of claim 46, wherein the number of template codons is from 3 to 15.

48. The method of claim 1, wherein the functional entity of the building block is a precursor of the functional entity which is incorporated into the templated molecule.

49. The method of claim 48, wherein the structure of the functional entity is changed as a result of the incorporation of the functional entity into the templated molecule during its synthesis.

50. The method of claim 1, wherein a functional entity of the one or more building blocks has from 1 to 10 reactive groups.

51. The method of claim 50, wherein a building block featuring only one reactive group is used for generating end positions of polymers.

52. The method of claim 50, wherein building blocks having two reactive groups are used for generating the body part of a polymer.

53. The method of claim 50, wherein building blocks having two reactive groups are used for generating scaffolds capable of being reacted with further functional entities.

54. The method of claim 53, wherein functional entities having two or more reactive groups are used for reactions with a scaffold in the form of a core structure comprising several reactive groups, wherein said reactions result in the formation of different templated molecules.

55. The method of claim 53, wherein the reactions of the reactive groups are aided by fill-in groups or catalysts.

56. The method of claim 1, wherein the anti-codon, the linker and the second zipping oligonucleotide of the one or more building block(s) forms a contiguous, linear oligonucleotide.

57. The method of claim 1, wherein building block anticodons are annealed to the template before the functional entities are connected to each other through a chemical reaction.

58. The method of claim 1, wherein individual building blocks are added separately and contacted with the template.

59. The method of claim 2, wherein building blocks contacting the template in a first reaction cycle result in the formation of codon:anti-codon hybrids with a lower annealing temperature than the annealing temperature of the codon:anti-codon hybrids which are formed when subsequently added, further building blocks are contacting the template in a second or further reaction cycle.

60. The method of claim 59, wherein the annealing temperature of codon:anti-codon hybrids in the second or further reaction cycle results in maintaining only second or further round building blocks in contact with the template, while the majority of the anti-codons of previous synthesis round building blocks, or anti-codons of non-reacted building blocks, become single stranded and are displaced from the template.

61. The method of claim 2, wherein the anti-codon of a building block remain annealed to the template after the transfer of a building block functional entity to a scaffold and during a subsequent reaction cycle.

62. The method of claim 2, wherein the anti-codon of a reacted building block is removed from the template prior to a repetition of steps d) and e).

63. The method of claim 1 comprising the further step of transferring the templated molecule to an anchorage point on the template, or to a nucleotide sequence complementing the template, to establish a chemical connection between the template and the templated molecule which allows the even further steps of denaturing enrichment or denaturing post-templating modification of the templated molecule to be performed.

64. The method of claim 63, wherein the chemical connection is a covalent chemical bond.

65. The method of claim 63, wherein the hybrid formed between the complementing nucleotide sequence and the template has a higher annealing temperature than the annealing temperature of hybrid(s) formed between any of the building block anticodons and the template.

66. The method of claim 65, wherein stringency conditions are used during templated molecule enrichment which result in the clearance of used building blocks from the template.

67. The method of claim 1, wherein the first functional entity is a scaffold which is reacted with two or more functional entities.

68. The method of claim 67, wherein the scaffold is reacted with functional entities emanating from building blocks.

69. The method of claim 67, wherein the scaffold comprises two or more reactive groups.

70. The method of claim 67, wherein the scaffold remains attached to the template through-out the synthesis of the templated molecule.

71. The method of claim 1, wherein the scaffold forms part of a building block the anti-codon of which is annealed to a flanking position of the template, which flanking position is not located between the template codons.

72. The method of claim 1, wherein the template comprises two or more codons, and wherein said building blocks attached to said two or more codons through their anti-codons have identical, complementary zipping oligonucleotides capable of dimerising in an ordered way.

73. The method of claim 72, wherein the hybridization of codon(s) to anti-codon(s) and the dimerisation of zipping oligonucleotides occur in separate steps, wherein the conditions for specific hybridization of codon(s) to anti-codon(s) of the template(s) are distinct from the conditions for dimerisation of the zipping oligonucleotides.

74. The method of claim 73, wherein the step of dimerisation of the zipping oligonucleotides is carried out under conditions ensuring that codons and anti-codons remain attached and under conditions allowing a reaction between functional entities on different building blocks.

75. The method of claim 1, wherein the codon is a series of nucleotides in the form of nucleobases on a backbone, wherein said nucleobases are selected from the group consisting of natural nucleobases and non-natural nucleobases obeying Watson-Crick hydrogen bonding rules.

76. The method of claim 75, wherein the nucleobases are selected from the group consisting of adenine, guanine, thymine, cytosine, uracil, purine, xanthine, diaminopurine, 8-oxo-$N^6$-methyladenine, 7-deazaxanthine, 7-deazaguanine, $N^4N^4$-ethanocytosin, $N^6,N^6$-ethano-2,6-diamino-purine, 5-methylcytosine, 5-($C^3C^6$)-alkynylcytosine, 5-fluorouracil, 5-bromouracil, pseudoisocytosine, 2-hydroxy-5-methyl-4-triazolopyridine, isocytosine, isoguanine and inosine.

77. The method of claim 75, wherein the backbone contains a sugar moiety and an internucleoside linker.

78. The method of claim 77, wherein the backbone is a pentose selected from ribose, 2'-deoxyribose, 2'-O-methyl-ribose, 2'-flour-ribose and 2'-4'-O-methylene-ribose (LNA).

79. The method of claim 78, wherein the nucleobase is attached to the 1' position of the pentose.

80. The method of claim 78, wherein the internucleoside linker connects the 3' end of a preceding monomer to a 5' end of a succeeding monomer when the sugar moiety of the backbone is a pentose.

81. The method of claim 80, wherein the internucleoside linker is a phosphodiester bond.

82. The method of claim 80, wherein the internucleoside linker is a bond selected from phosphorothioate bonds, methylphosphonate bonds, phosphoramidate bonds, phosphotriester bonds and phosphodithioate bonds.

83. The method of claim 1, wherein the template is immobilised on a solid support.

84. The method of claim 83, wherein the solid support is a bead.

85. The method of claim 83, wherein a biotin group is incorporated in the template, and wherein the solid support is as matrix material coated with streptavidin.

86. The method of claim 1, wherein the first functional entity is linked to the template through a selectively cleavable linker which enables the separation of the synthesized, template-directed molecule from the template at a predetermined time.

87. The method of claim 86, wherein the first functional entity is a scaffold.

88. A method for generating a library of different bifunctional complexes, said method comprising the steps of subjecting a plurality of templates to the method according to claim 1, thereby generating a library of different bifunctional complexes each comprising a templated molecule attached to the template or complementary template which directed the synthesis of the templated molecule.

89. The method of claim 88, wherein the number of different bifunctional complexes in the library is at least $10^3$.

90. The method of claim 88, wherein the number of different bifunctional complexes in the library is at least $10^6$.

91. The method of claim 88, wherein the number of different bifunctional complexes in the library is at least $10^9$.

92. The method of claim 88, wherein a plurality of different templates is provided in step a) and wherein a plurality of different building blocks is provided in step c).

93. A method for generating a library of different bifunctional complexes, said method comprising the steps of subjecting a plurality of templates simultaneously to the method according to claim 1, thereby generating a library of different bifunctional complexes each comprising a templated molecule attached to the template or complementary template which directed the synthesis of the templated molecule.

94. The method of claim 88, wherein the templated molecules of the library are synthesized by sequentially contacting the templates with subsets of building blocks to be used in the synthesis if the templated molecules.

95. The method of claim 88, wherein each template comprises a number of coding sections, and wherein each coding section specifies one or more unique codons.

96. The method of claim 95, wherein the coding sections are positioned in a linear sequence with individual coding sections positioned immediately next to each other.

97. The method of claim 96, wherein the coding sections are interspaced by a spacer sequence.

98. The method of claim 95, wherein the template is branched.

99. The method of claim 95, wherein each template has from 2 to 50 coding regions.

100. The method of claim 95, wherein each template has from 3 to 30 coding regions.

101. The method of claim 95, wherein each template has from 4 to 15 coding regions.

102. The method of claim 99, wherein the number of unique codons in each coding region is the same.

103. The method of claim 99, wherein each coding region contains a different number of unique codons.

104. The method of claim 99, wherein each coding region contains a single unique codon.

105. The method of claim 88, comprising the further step of subjecting the library of bifunctional complexes to an enrichment comprising the steps of:
  i) exposing the library to conditions enriching the library with complexes having a predetermined activity,
  ii) amplifying the complexes of the enriched library, thereby obtaining amplification product(s),
  iii) obtaining an enriched library having a higher ratio of complexes comprising templated molecules with the predetermined activity.

106. The method of claim 105, wherein the amplification of the complexes of the enriched library comprises the steps of contacting the library of complexes with amplification means, amplifying the templates or the complementing templates, and conducting the method using the amplification product(s) as templates.

107. The method of claim 105, wherein steps i) and ii) are repeated from 2 to 5 times.

108. The method of claim 107, wherein generated complexes are identified after the completion of each cycle of repetition.

109. The method of claim 107, wherein the complexes are identified after the last repetition cycle.

110. The method of claim 108, wherein the identification after the enrichment involves determination of the sequence of the template and/or structural determination of the templated molecule and/or the entire complex having the predetermined activity.

111. The method of 105, wherein enrichment of library complexes is obtained by screening for complexes having an affinity for or an effect on a target molecule.

112. The method of claim 111, wherein the target molecule is selected from soluble receptors, cell surface receptors, enzyme inhibitors and surface epitopes.

113. The method of claim 111, wherein the target molecule is selected from receptors, enzymes, hormones, transcription factors, ion channels and DNA.

114. The method of claim 113, wherein the target molecule is selected from receptors and enzymes.

115. The method of claim 114, wherein the target molecule is selected from G protein coupled receptors and proteases.

116. The method of claim 1, comprising the further step of contacting the templated molecule with a target molecule selected from receptors, enzymes, hormones, transcription factors, ion channels and DNA, and identifying a templated molecule contacting a target molecule as an agonist or an antagonist for the target molecule.

117. A bifunctional complex comprising a templated molecule attached to the template which directed the synthesis thereof, wherein said template is further attached to at least two zipping oligonucleotides capable of reversibly dimerizing in an ordered way, said bifunctional complex being obtainable by the method of claim 1, wherein at least one of the following conditions applies:
  (i) the templated molecule is a beta-peptide,
  (ii) the templated molecule is a gamma-peptide,
  (iii) the templated molecule is an omega-peptide,
  (iv) the templated molecule is a cyclohexane- and cyclopentanebackbone modified beta-peptide,
  (v) the templated molecule is a vinylogous polypeptide,
  (vi) the templated molecule is a peptide having prosthetic group(s),
  (vii) the templated molecule is an aliphatic polycycle,
  (viii) the templated molecule is an aromatic polycycle,
  (ix) the templated molecule is a polyheterocycle,
  (x) the templated molecule is a monofunctional, difunctional or trifunctional, nonaromatic carbocycle,
  (xi) the templated molecule is a monocyclic, bicyclic or tricyclic hydrocarbon,
  (xii) the templated molecule is a monofunctional, difunctional or trifunctional nonaromatic heterocycle,
  (xiii) the templated molecule is a monocyclic, bicyclic or tricyclic heterocycles,
  (xiv) the templated molecule is a bridged polycyclic heterocycle,
  (xv) the templated molecule is a monofunctional, difunctional or trifunctional aromatic carbocycle,
  (xvi) the templated molecule is a monocyclic, bicyclic or tricyclic aromatic carbocycle,
  (xvii) the templated molecule is a monofunctional, difunctional or trifunctional aromatic heterocycle,
  (xviii) the templated molecule is a monocyclic, bicyclic or tricyclic heterocycle, or
  (xix) the templated molecule is a steroid.

118. The bifunctional complex according to claim 117, wherein the templated molecule is a beta-peptide.

119. The bifunctional complex according to claim 117, wherein the templated molecule is a gamma-peptide.

120. The bifunctional complex according to claim 117, wherein the templated molecule is an omega-peptide.

121. The bifunctional complex according to claim 117, wherein the templated molecule is a cyclohexane and cyclopentane-backbone modified beta-peptide.

122. The bifunctional complex according to claim 117, wherein the templated molecule is a vinylogous polypeptide.

123. The bifunctional complex according to claim 117, wherein the templated molecule is a peptide having prosthetic group(s).

124. The bifunctional complex according to claim 117, wherein the templated molecule is an aliphatic polycycle.

125. The bifunctional complex according to claim 117, wherein the templated molecule is an aromatic polycycle.

126. The bifunctional complex according to claim 117, wherein the templated molecule is a polyheterocycle.

127. The bifunctional complex according to claim 117, wherein the templated molecule is a monofunctional, difunctional or trifunctional, nonaromatic carbocycle.

128. The bifunctional complex according to claim 117, wherein the templated molecule is a monocyclic, bicyclic or tricyclic hydrocarbon.

129. The bifunctional complex according to claim 117, wherein the templated molecule is a monofunctional, difunctional or trifunctional nonaromatic heterocycle.

130. The bifunctional complex according to claim 117, wherein the templated molecule is a monocyclic, bicyclic or tricyclic heterocycles.

131. The bifunctional complex according to claim 117, wherein the templated molecule is a bridged polycyclic heterocycle.

132. The bifunctional complex according to claim 117, wherein the templated molecule is a monofunctional, difunctional or trifunctional aromatic carbocycle.

133. The bifunctional complex according to claim 117, wherein the templated molecule is a monocyclic, bicyclic or tricyclic aromatic carbocycle.

134. The bifunctional complex according to claim 117, wherein the templated molecule is a monofunctional, difunctional or trifunctional aromatic heterocycle.

135. The bifunctional complex according to claim 117, wherein the templated molecule is a monocyclic, bicyclic or tricyclic heterocycle.

136. The bifunctional complex according to claim 117, wherein the templated molecule is a steroid.

137. A library of different bifunctional complexes according to claim 117.

138. The library according to claim 137, wherein each bifunctional complex comprises a different templated molecule.

139. The library according to claim 137, wherein the number of different bifunctional complexes in the library is at least $10^3$.

140. The library according to claim 137, wherein the number of different bifunctional complexes in the library is at least $10^6$.

141. The library according to claim 137, wherein the number of different bifunctional complexes in the library is at least $10^9$.

142. A bifunctional complex comprising a templated molecule attached to the template which directed the synthesis thereof, wherein said template is further attached to at least two zipping oligonucleotides capable of reversibly dimerizing in an ordered way, said bifunctional complex being obtainable by the method of claim 1, wherein the templated molecule is not a polynucleotide.

143. The bifunctional complex according to claim 141, wherein the templated molecule is a monofunctional, difunctional or trifunctional open-chain hydrocarbon.

144. The bifunctional complex according to claim 141 wherein the templated molecule is a bridged polycyclic hydrocarbon.

145. The method of claim 1 wherein the chemical connection of the further functional entity to the first functional entity, referred to in steps (c) and (e), is a covalent connection.

* * * * *

UNITED STATES PATENT AND TRADEMARK OFFICE
CERTIFICATE OF CORRECTION

PATENT NO. : 7,413,854 B2  Page 1 of 1
APPLICATION NO. : 10/507121
DATED : August 19, 2008
INVENTOR(S) : Pedersen et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (237) days Delete the phrase "by 237 days" and insert -- by 387 days --

Signed and Sealed this

Sixth Day of April, 2010

David J. Kappos
*Director of the United States Patent and Trademark Office*

SEQUENCE LISTING

<160> NUMBER OF SEQ ID NOS: 61

<210> SEQ ID NO 1
<211> LENGTH: 15
<212> TYPE: DNA
<213> ORGANISM: artificial sequence
<220> FEATURE:
<223> OTHER INFORMATION: Building block oligo used in examples 1 to 11
<220> FEATURE:
<221> NAME/KEY: misc_feature
<222> LOCATION: (15)..(15)
<223> OTHER INFORMATION: Carboxy-modifier C2 dT (obtained from Glen
      Research, catalogue #10-1035-90)

<400> SEQUENCE: 1
gctactcgta cgagn                                                           15

<210> SEQ ID NO 2
<211> LENGTH: 15
<212> TYPE: DNA
<213> ORGANISM: artificial sequence
<220> FEATURE:
<223> OTHER INFORMATION: Building block oligo used in examples 1 to 11
<220> FEATURE:
<221> NAME/KEY: misc_feature
<222> LOCATION: (15)..(15)
<223> OTHER INFORMATION: Amino-modifier C2 dT (obtained from Glen
      Research catalogue #10-1037-90)

<400> SEQUENCE: 2
gctactcgta cgagn                                                           15

<210> SEQ ID NO 3
<211> LENGTH: 15
<212> TYPE: DNA
<213> ORGANISM: artificial sequence
<220> FEATURE:
<223> OTHER INFORMATION: Building block oligo used in examples 1 to 11
<220> FEATURE:
<221> NAME/KEY: misc_feature
<222> LOCATION: (15)..(15)
<223> OTHER INFORMATION: Amino modifier C6 dT (obtained from Glen
      Research, catalogue #10-1039-90)

<400> SEQUENCE: 3
gctactcgta cgagn                                                           15

<210> SEQ ID NO 4
<211> LENGTH: 15
<212> TYPE: DNA
<213> ORGANISM: Artificial sequence
<220> FEATURE:
<223> OTHER INFORMATION: Building block oligo used in examples 1 to 11
<220> FEATURE:
<221> NAME/KEY: misc_feature
<222> LOCATION: (1)..(1)
<223> OTHER INFORMATION: Carboxy-modifier C2 dT (obtained from Glen
      Research, catalogue #10-1035-90)

<400> SEQUENCE: 4
ncacttgcag acagc                                                           15

<210> SEQ ID NO 5
<211> LENGTH: 15
<212> TYPE: DNA
<213> ORGANISM: Artificial sequence
<220> FEATURE:
<223> OTHER INFORMATION: Building block oligo used in examples 1 to 11

```
<220> FEATURE:
<221> NAME/KEY: misc_feature
<222> LOCATION: (1)..(1)
<223> OTHER INFORMATION: Amino-modifier C2 dT (obtained from Glen
      Research, catalogue #10-1037-90)

<400> SEQUENCE: 5
ncacttgcag acagc                                                          15

<210> SEQ ID NO 6
<211> LENGTH: 15
<212> TYPE: DNA
<213> ORGANISM: Artificial sequence
<220> FEATURE:
<223> OTHER INFORMATION: Building block oligo used in examples 1 to 11
<220> FEATURE:
<221> NAME/KEY: misc_feature
<222> LOCATION: (1)..(1)
<223> OTHER INFORMATION: Amino modifier C6 dT (obtained from Glen
      Research, catalogue #10-1039-90)

<400> SEQUENCE: 6
ncacttgcag acagc                                                          15

<210> SEQ ID NO 7
<211> LENGTH: 14
<212> TYPE: DNA
<213> ORGANISM: Artificial sequence
<220> FEATURE:
<223> OTHER INFORMATION: Building block oligo used in examples 1 to 11

<400> SEQUENCE: 7
gctactcgta cgag                                                           14

<210> SEQ ID NO 8
<211> LENGTH: 15
<212> TYPE: DNA
<213> ORGANISM: Artificial sequence
<220> FEATURE:
<223> OTHER INFORMATION: Building block oligo used in examples 1 to 11
<220> FEATURE:
<221> NAME/KEY: misc_feature
<222> LOCATION: (15)..(15)
<223> OTHER INFORMATION: Carboxy-modifier C2 dT (obtained from Glen
      Research, catalogue #10-1035-90)

<400> SEQUENCE: 8
gctactggca tcggn                                                          15

<210> SEQ ID NO 9
<211> LENGTH: 15
<212> TYPE: DNA
<213> ORGANISM: Artificial sequence
<220> FEATURE:
<223> OTHER INFORMATION: Building block oligo used in examples 1 to 11
<220> FEATURE:
<221> NAME/KEY: misc_feature
<222> LOCATION: (15)..(15)
<223> OTHER INFORMATION: Amino-modifier C2 dT (obtained from Glen
      Research, catalogue #10-1037-90)

<400> SEQUENCE: 9
gctactggca tcggn                                                          15

<210> SEQ ID NO 10
<211> LENGTH: 15
<212> TYPE: DNA
<213> ORGANISM: Artificial sequence
<220> FEATURE:
```

<223> OTHER INFORMATION: Building block oligo used in examples 1 to 11
<220> FEATURE:
<221> NAME/KEY: misc_feature
<222> LOCATION: (1)..(1)
<223> OTHER INFORMATION: Amino-modifier C2 dT (obtained from Glen
      Research, catalogue #10-1037-90)

<400> SEQUENCE: 10
ncacttgcag acagc                                                       15

<210> SEQ ID NO 11
<211> LENGTH: 56
<212> TYPE: DNA
<213> ORGANISM: Artificial sequence
<220> FEATURE:
<223> OTHER INFORMATION: Building block oligo used in examples 1 to 11
<220> FEATURE:
<221> NAME/KEY: misc_feature
<222> LOCATION: (56)..(56)
<223> OTHER INFORMATION: Carboxy-modifier C2 dT (obtained from Glen
      Research, catalogue #10-1035-90)

<400> SEQUENCE: 11
cgacctctgg attgcatcgg tcatggctga ctgtccgtcg aatgtgtcca gttacn         56

<210> SEQ ID NO 12
<211> LENGTH: 56
<212> TYPE: DNA
<213> ORGANISM: Artificial sequence
<220> FEATURE:
<223> OTHER INFORMATION: Building block oligo used in examples 1 to 11
<220> FEATURE:
<221> NAME/KEY: Artificial sequence
<222> LOCATION: (1)..(1)
<223> OTHER INFORMATION: Amino modifier C6 dT (obtained from Glen
      Research, catalogue #10-1039-90)
<220> FEATURE:
<221> NAME/KEY: misc_feature
<222> LOCATION: (1)..(1)
<223> OTHER INFORMATION: n is a, c, g, or t

<400> SEQUENCE: 12
ngtaactgga ctgtaagctg cctgtcagtc ggtactgacc tgtcgagcat ccagct         56

<210> SEQ ID NO 13
<211> LENGTH: 56
<212> TYPE: DNA
<213> ORGANISM: Artificial sequence
<220> FEATURE:
<223> OTHER INFORMATION: misc_feature
<220> FEATURE:
<221> NAME/KEY: misc_feature
<222> LOCATION: (1)..(1)
<223> OTHER INFORMATION: Amino modifier C6 dT (obtained from Glen
      Research, catalogue #10-1039-90)

<400> SEQUENCE: 13
ngtaacaccT gtgtaagctg cctgtcagtc ggtactgacc tgtcgagcat ccagct         56

<210> SEQ ID NO 14
<211> LENGTH: 56
<212> TYPE: DNA
<213> ORGANISM: Artificial sequence
<220> FEATURE:
<223> OTHER INFORMATION: Building block oligo used in examples 1 to 11
<220> FEATURE:
<221> NAME/KEY: misc_feature
<222> LOCATION: (1)..(1)
<223> OTHER INFORMATION: Amino modifier C6 dT (obtained from Glen
      Research, catalogue #10-1039-90)

<400> SEQUENCE: 14
ncattgacct gtgtaagctg cctgtcagtc ggtactgacc tgtcgagcat ccagct        56

<210> SEQ ID NO 15
<211> LENGTH: 56
<212> TYPE: DNA
<213> ORGANISM: Artificial sequence
<220> FEATURE:
<223> OTHER INFORMATION: Building block oligo used in examples 1 to 11
<220> FEATURE:
<221> NAME/KEY: misc_feature
<222> LOCATION: (3)..(3)
<223> OTHER INFORMATION: Amino modifier C6 dT (obtained from Glen
      Research, catalogue #10-1039-90)

<400> SEQUENCE: 15
agnaacacct gtgtaagctg cctgtcagtc ggtactgacc tgtcgagcat ccagct        56

<210> SEQ ID NO 16
<211> LENGTH: 58
<212> TYPE: DNA
<213> ORGANISM: Artificial sequence
<220> FEATURE:
<223> OTHER INFORMATION: Building block oligo used in examples 1 to 11
<220> FEATURE:
<221> NAME/KEY: misc_feature
<222> LOCATION: (1)..(1)
<223> OTHER INFORMATION: Amino modifier C6 dT (obtained from Glen
      Research, catalogue #10-1039-90)

<400> SEQUENCE: 16
nttgtaactg gactgtaagc tgcctgtcag tcggtactga cctgtcgagc atccagct      58

<210> SEQ ID NO 17
<211> LENGTH: 58
<212> TYPE: DNA
<213> ORGANISM: Artificial sequence
<220> FEATURE:
<223> OTHER INFORMATION: Building block oligo used in examples 1 to 11
<220> FEATURE:
<221> NAME/KEY: misc_feature
<222> LOCATION: (58)..(58)
<223> OTHER INFORMATION: Amino-modifier C2 dT (obtained from Glen
      Research, catalogue #10-1035-90)

<400> SEQUENCE: 17
cgacctctgg attgcatcgg tcatggctga ctgtccgtcg aatgtgtcca gttacttn      58

<210> SEQ ID NO 18
<211> LENGTH: 30
<212> TYPE: DNA
<213> ORGANISM: Artificial sequence
<220> FEATURE:
<223> OTHER INFORMATION: Template used in examples 1 to 11

<400> SEQUENCE: 18
gctgtctgca agtgaaccga tgccagtagc                                     30

<210> SEQ ID NO 19
<211> LENGTH: 40
<212> TYPE: DNA
<213> ORGANISM: Artificial sequence
<220> FEATURE:
<223> OTHER INFORMATION: Template used in examples 1 to 11

<400> SEQUENCE: 19
agctggatgc tcgacaggtc ccgatgcaat ccagaggtcg                          40

<210> SEQ ID NO 20
<211> LENGTH: 51
<212> TYPE: DNA
<213> ORGANISM: Artificial sequence
<220> FEATURE:
<223> OTHER INFORMATION: Template used in examples 1 to 11
<220> FEATURE:
<221> NAME/KEY: misc_feature
<222> LOCATION: (51)..(51)
<223> OTHER INFORMATION: Biotin phosphoramidite (obtained from Glen
    Research, Catalogue #10-1953-95)

<400> SEQUENCE: 20
gctgtctgca agtgaactcg tacgagtagc gacagtcgac atcggtcacg n            51

<210> SEQ ID NO 21
<211> LENGTH: 52
<212> TYPE: DNA
<213> ORGANISM: Artificial sequence
<220> FEATURE:
<223> OTHER INFORMATION: Template used in examples 1 to 11
<220> FEATURE:
<221> NAME/KEY: misc_feature
<222> LOCATION: (51)..(51)
<223> OTHER INFORMATION: Biotin phosphoramidite (obtained from Glen
    Research, Catalogue #10-1953-95)
<220> FEATURE:
<221> NAME/KEY: misc_feature
<222> LOCATION: (52)..(52)
<223> OTHER INFORMATION: n is a, c, g, or t

<400> SEQUENCE: 21
gctgtctgca agtgacactc gtacgagtag cgacagtcga catcggtcac gn           52

<210> SEQ ID NO 22
<211> LENGTH: 53
<212> TYPE: DNA
<213> ORGANISM: Artificial sequence
<220> FEATURE:
<223> OTHER INFORMATION: Template used in examples 1 to 11
<220> FEATURE:
<221> NAME/KEY: misc_feature
<222> LOCATION: (53)..(53)
<223> OTHER INFORMATION: Biotin-amedit

<400> SEQUENCE: 22
gctgtctgca agtgacgact cgtacgagta gcgacagtcg acatcggtca cgn          53

<210> SEQ ID NO 23
<211> LENGTH: 81
<212> TYPE: DNA
<213> ORGANISM: Artificial sequence
<220> FEATURE:
<223> OTHER INFORMATION: Template used in examples 1 to 11
<220> FEATURE:
<221> NAME/KEY: misc_feature
<222> LOCATION: (81)..(81)
<223> OTHER INFORMATION: Biotin phosphoramidite (obtained from Glen
    Research, Catalogue #10-1953-95)

<400> SEQUENCE: 23
gctgtctgca agtgacgact gatccagtga catgcgtacc atcgaactcg tacgagtagc   60
gacagtcgac atcggtcacg n                                             81

<210> SEQ ID NO 24
<211> LENGTH: 47
<212> TYPE: DNA
<213> ORGANISM: Artificial sequence
<220> FEATURE:

```
<223> OTHER INFORMATION: Trisamine scaffold oligo building block used in
      example 12
<220> FEATURE:
<221> NAME/KEY: misc_feature
<222> LOCATION: (46)..(46)
<223> OTHER INFORMATION: Carboxy-modifier C2 dT (obtained from Glen
      Research, catalogue #10-1035-90)

<400> SEQUENCE: 24
gacctgtcga gcatccagct tcatgggaat tcctcgtcca caatgnt                47

<210> SEQ ID NO 25
<211> LENGTH: 52
<212> TYPE: DNA
<213> ORGANISM: Artificial sequence
<220> FEATURE:
<223> OTHER INFORMATION: building block oligo used in example 13
<220> FEATURE:
<221> NAME/KEY: misc_feature
<222> LOCATION: (1)..(1)
<223> OTHER INFORMATION: Thiol modifier (obtained from Glen Research,
      catalogue #10-1053-95)

<400> SEQUENCE: 25
ncattgacct gtctgccbtg tcagtcggta ctgtggtaac gcggatcgac ct          52

<210> SEQ ID NO 26
<211> LENGTH: 62
<212> TYPE: DNA
<213> ORGANISM: Artificial sequence
<220> FEATURE:
<223> OTHER INFORMATION: Oligo building block used in example 13
<220> FEATURE:
<221> NAME/KEY: misc_feature
<222> LOCATION: (1)..(1)
<223> OTHER INFORMATION: Thiol modifier (obtained from Glen Research,
      catalogue #10-1053-95)

<400> SEQUENCE: 26
ncattgacct gaaccatgbt aagctgcctg tcagtcggta ctacgactac gttcaggcaa  60
ga                                                                62

<210> SEQ ID NO 27
<211> LENGTH: 81
<212> TYPE: DNA
<213> ORGANISM: Artificial sequence
<220> FEATURE:
<223> OTHER INFORMATION: Template oligo used in example 14
<220> FEATURE:
<221> NAME/KEY: misc_feature
<222> LOCATION: (1)..(1)
<223> OTHER INFORMATION: Biotin phosphoramidite (obtained from Glen
      Research, Catalogue #10-1953-95)

<400> SEQUENCE: 27
ntcttgcctg aacgtagtcg taggtcgatc cgcgttacca gagctggatg ctcgacaggt  60
cccgatgcaa tccagaggtc g                                           81

<210> SEQ ID NO 28
<211> LENGTH: 31
<212> TYPE: DNA
<213> ORGANISM: Artificial sequence
<220> FEATURE:
<223> OTHER INFORMATION: DNA oligos for building blocks used in
      examples 15 to 20
<220> FEATURE:
<221> NAME/KEY: misc_feature
<222> LOCATION: (1)..(1)
<223> OTHER INFORMATION: Amino modifier C6 dT (obtained from Glen
```

-continued

Research, catalogue #10-1039-90)

<400> SEQUENCE: 28
ngtaacacct ggacctgtcg agcatccagc t                                    31

<210> SEQ ID NO 29
<211> LENGTH: 23
<212> TYPE: DNA
<213> ORGANISM: Artificial sequence
<220> FEATURE:
<223> OTHER INFORMATION: DNA oligos for building blocks used in examples
      15 to 20
<220> FEATURE:
<221> NAME/KEY: misc_feature
<222> LOCATION: (23)..(23)
<223> OTHER INFORMATION: Carboxy-modifier C2 dT (obtained from Glen
      Research, catalogue #10-1035-90)

<400> SEQUENCE: 29
tctggattgc atcgggagtt acn                                             23

<210> SEQ ID NO 30
<211> LENGTH: 56
<212> TYPE: DNA
<213> ORGANISM: Artificial sequence
<220> FEATURE:
<223> OTHER INFORMATION: DNA oligos for building blocks used in examples
      15 to 20
<220> FEATURE:
<221> NAME/KEY: misc_feature
<222> LOCATION: (1)..(1)
<223> OTHER INFORMATION: Amino modifier C6 dT (obtained from Glen
      Research, catalogue #10-1039-90)

<400> SEQUENCE: 30
ngtaactcct gtgtaagctg cctgtcagtc ggtactgacc tgtcgagcat ccagct         56

<210> SEQ ID NO 31
<211> LENGTH: 56
<212> TYPE: DNA
<213> ORGANISM: Artificial sequence
<220> FEATURE:
<223> OTHER INFORMATION: DNA oligos for building blocks used in examples
      15 to 20
<220> FEATURE:
<221> NAME/KEY: misc_feature
<222> LOCATION: (1)..(1)
<223> OTHER INFORMATION: Amino modifier C6 dT (obtained from Glen
      Research, catalogue #10-1039-90)

<400> SEQUENCE: 31
ngtaactgct gtgtaagctg cctgtcagtc ggtactgacc tgtcgagcat ccagct         56

<210> SEQ ID NO 32
<211> LENGTH: 56
<212> TYPE: DNA
<213> ORGANISM: Artificial sequence
<220> FEATURE:
<223> OTHER INFORMATION: DNA oligos for building blocks used in examples
      15 to 20
<220> FEATURE:
<221> NAME/KEY: misc_feature
<222> LOCATION: (1)..(1)
<223> OTHER INFORMATION: Amino modifier C6 dT (obtained from Glen
      Research, catalogue #10-1039-90)

<400> SEQUENCE: 32
ngtaactggt gtgtaagctg cctgtcagtc ggtactgacc tgtcgagcat ccagct         56

```
<210> SEQ ID NO 33
<211> LENGTH: 76
<212> TYPE: DNA
<213> ORGANISM: Artificial sequence
<220> FEATURE:
<223> OTHER INFORMATION: DNA oligos for building blocks used in examples
      15 to 20
<220> FEATURE:
<221> NAME/KEY: misc_feature
<222> LOCATION: (76)..(76)
<223> OTHER INFORMATION: Carboxy-modifier C2 dT (obtained from Glen
      Research, catalogue #10-1035-90)

<400> SEQUENCE: 33
cgacctctgg attgcatcgg tcatttttt tttttttttt ttttggctga ctgtccgtcg     60
aatgtgtcca gttacn                                                    76

<210> SEQ ID NO 34
<211> LENGTH: 21
<212> TYPE: DNA
<213> ORGANISM: Artificial sequence
<220> FEATURE:
<223> OTHER INFORMATION: DNA oligos for building blocks used in examples
      15 to 20
<220> FEATURE:
<221> NAME/KEY: misc_feature
<222> LOCATION: (1)..(1)
<223> OTHER INFORMATION: Amino modifier C6 dT (obtained from Glen
      Research, catalogue #10-1039-90)

<400> SEQUENCE: 34
ngacctgtcg agcatccagc t                                              21

<210> SEQ ID NO 35
<211> LENGTH: 21
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (21)..(21)
<223> OTHER INFORMATION: Carboxy-modifier C2 dT (obtained from Glen
      Research, catalogue #10-1035-90)

<400> SEQUENCE: 35
tctggattgc atcgggttac n                                              21

<210> SEQ ID NO 36
<211> LENGTH: 21
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (21)..(21)
<223> OTHER INFORMATION: Carboxy-modifier C2 dT (obtained from Glen
      Research, catalogue #10-1035-90)

<400> SEQUENCE: 36
tctggattgc atcggttttt n                                              21

<210> SEQ ID NO 37
<211> LENGTH: 31
<212> TYPE: DNA
<213> ORGANISM: Artificial sequence
<220> FEATURE:
<223> OTHER INFORMATION: DNA oligos for building blocks used in examples 15 to 20
<220> FEATURE:
```

```
<221> NAME/KEY: misc_feature
<222> LOCATION: (1)..(1)
<223> OTHER INFORMATION: Amino-modifier 5 (obtained from Glen
      Research, catalogue #10-1905-90)

<400> SEQUENCE: 37
ngtaacacct ggacctgtcg agcatccagc t                              31

<210> SEQ ID NO 38
<211> LENGTH: 31
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (31)..(31)
<223> OTHER INFORMATION: Carboxy-modifier C2 dT (obtained from Glen
      Research, catalogue #10-1035-90)

<400> SEQUENCE: 38
cgacctctgg attgcatcgg gcacggttac n                              31

<210> SEQ ID NO 39
<211> LENGTH: 31
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (1)..(1)
<223> OTHER INFORMATION: Amino modifier C6 dT (obtained from Glen
      Research, catalogue #10-1039-90)

<400> SEQUENCE: 39
nctggacagc tcgtaggtcg tttttttttt t                              31

<210> SEQ ID NO 40
<211> LENGTH: 21
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (1)..(1)
<223> OTHER INFORMATION: Amino modifier C6 dT (obtained from Glen
      Research, catalogue #10-1039-90)

<400> SEQUENCE: 40
ngacctgtcg agcatccagc t                                         21

<210> SEQ ID NO 41
<211> LENGTH: 21
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (1)..(1)
<223> OTHER INFORMATION: Carboxy-modifier C2 dT (obtained from Glen
      Research, catalogue #10-1035-90)

<400> SEQUENCE: 41
ngacctgtcg agcatccagc t                                         21

<210> SEQ ID NO 42
```

```
<211> LENGTH: 27
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (27)..(27)
<223> OTHER INFORMATION: Amino modifier C6 dT (obtained from Glen
      Research, catalogue #10-1039-90)

<400> SEQUENCE: 42
cgacctctgg attgcatcgg tgttacn                                              27

<210> SEQ ID NO 43
<211> LENGTH: 26
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (26)..(26)
<223> OTHER INFORMATION: Amino modifier C6 dT (obtained from Glen
      Research, catalogue #10-1039-90)

<400> SEQUENCE: 43
acgactacgt tcaggcaaga gttacn                                               26

<210> SEQ ID NO 44
<211> LENGTH: 31
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (1)..(1)
<223> OTHER INFORMATION: Carboxy-modifier C2 dT (obtained from Glen
      Research, catalogue #10-1035-90)

<400> SEQUENCE: 44
nctggacagc tcgtaggtcg ttttttttt t                                          31

<210> SEQ ID NO 45
<211> LENGTH: 21
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (21)..(21)
<223> OTHER INFORMATION: Amino modifier C6 dT (obtained from Glen
      Research, catalogue #10-1039-90)

<400> SEQUENCE: 45
cgacctctgg attgcatcgg n                                                    21

<210> SEQ ID NO 46
<211> LENGTH: 25
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (25)..(25)
<223> OTHER INFORMATION: Amino modifier C6 dT (obtained from Glen
      Research, catalogue #10-1039-90)
```

```
<400> SEQUENCE: 46
cgacctctgg attgcatcgg ttacn                                         25

<210> SEQ ID NO 47
<211> LENGTH: 26
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (1)..(1)
<223> OTHER INFORMATION: Amino-modifier 5 (obtained from Glen Research, catalogue #
      10-1905-90)

<400> SEQUENCE: 47
ngtaacgacc tgtcgagcat ccagct                                        26

<210> SEQ ID NO 48
<211> LENGTH: 28
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (1)..(1)
<223> OTHER INFORMATION: Amino-modifier 5 (obtained from Glen Research, catalogue #
      10-1905-90)

<400> SEQUENCE: 48
ngtaactgga cctgtcgagc atccagct                                      28

<210> SEQ ID NO 49
<211> LENGTH: 26
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (26)..(26)
<223> OTHER INFORMATION: Carboxy-modifier C2 dT (obtained from Glen Research, catalogue #
      10-1035-90)

<400> SEQUENCE: 49
acgactacgt tcaggcaaga gttacn                                        26

<210> SEQ ID NO 50
<211> LENGTH: 28
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (28)..(28)
<223> OTHER INFORMATION: Carboxy-modifier C2 dT (obtained from Glen Research, catalogue #
      10-1035-90)

<400> SEQUENCE: 50
acgactacgt tcaggcaaga gcgttacn                                      28

<210> SEQ ID NO 51
<211> LENGTH: 31
<212> TYPE: DNA
<213> ORGANISM: Artificial sequence
<220> FEATURE:
<223> OTHER INFORMATION: DNA oligos for building blocks used in examples 15 to 20
```

```
<220> FEATURE:
<221> NAME/KEY: misc_feature
<222> LOCATION: (31)..(31)
<223> OTHER INFORMATION: Carboxy-modifier C2 dT (obtained from Glen Research, catalogue #
      10-1035-90)

<400> SEQUENCE: 51
acgactacgt tcaggcaaga gcacggttac n                                          31

<210> SEQ ID NO 52
<211> LENGTH: 28
<212> TYPE: DNA
<213> ORGANISM: Artificial sequence
<220> FEATURE:
<223> OTHER INFORMATION: DNA oligos for building blocks used in examples 15 to 20
<220> FEATURE:
<221> NAME/KEY: misc_feature
<222> LOCATION: (28)..(28)
<223> OTHER INFORMATION: Carboxy-modifier C2 dT (obtained from Glen Research, catalogue #
      10-1035-90)

<400> SEQUENCE: 52
cgacctctgg attgcatcgg gcgttacn                                              28

<210> SEQ ID NO 53
<211> LENGTH: 31
<212> TYPE: DNA
<213> ORGANISM: Artificial sequence
<220> FEATURE:
<223> OTHER INFORMATION: Oligo building block used in examples 15 to 20
<220> FEATURE:
<221> NAME/KEY: misc_feature
<222> LOCATION: (31)..(31)
<223> OTHER INFORMATION: Carboxy-modifier C2 dT (obtained from Glen Research, catalogue #
      10-1035-90)

<400> SEQUENCE: 53
ctggtaacgc ggatcgacct gcacggttac n                                          31

<210> SEQ ID NO 54
<211> LENGTH: 28
<212> TYPE: DNA
<213> ORGANISM: Artificial sequence
<220> FEATURE:
<223> OTHER INFORMATION: Oligo building block used in examples 15 to 20
<220> FEATURE:
<221> NAME/KEY: misc_feature
<222> LOCATION: (28)..(28)
<223> OTHER INFORMATION: Carboxy-modifier C2 dT (obtained from Glen Research, catalogue #
      10-1035-90)

<400> SEQUENCE: 54
ctggtaacgc ggatcgacct gcgttacn                                              28

<210> SEQ ID NO 55
<211> LENGTH: 80
<212> TYPE: DNA
<213> ORGANISM: Artificial sequence
<220> FEATURE:
<223> OTHER INFORMATION: Template oligo used in examples 15 to 20

<400> SEQUENCE: 55
agctggatgc tcgacaggtc aggtcgatcc gcgttaccag tcttgcctga acgtagtcgt           60
ccgatgcaat ccagaggtcg                                                      80

<210> SEQ ID NO 56
<211> LENGTH: 87
<212> TYPE: DNA
```

```
<213> ORGANISM: Artificial sequence
<220> FEATURE:
<223> OTHER INFORMATION: Template oligo used in examples 15 to 20

<400> SEQUENCE: 56
agctggatgc tcgacaggtc aagtaacagg tcgatccgcg ttaccagtct tgcctgaacg    60
tagtcgtccg atgcaatcca gaggtcg                                       87

<210> SEQ ID NO 57
<211> LENGTH: 36
<212> TYPE: DNA
<213> ORGANISM: Artificial sequence
<220> FEATURE:
<223> OTHER INFORMATION: Template oligo used in examples 15 to 20

<400> SEQUENCE: 57
cgacctacga gctgtccaga agtaacaggt cgatcc                             36

<210> SEQ ID NO 58
<211> LENGTH: 90
<212> TYPE: DNA
<213> ORGANISM: Artificial sequence
<220> FEATURE:
<223> OTHER INFORMATION: Template oligo used in examples 15 to 20

<400> SEQUENCE: 58
agctggatgc tcgacaggtc aagtaacacc aggtcgatcc gcgttaccag tcttgcctga    60
acgtagtcgt ccgatgcaat ccagaggtcg                                    90

<210> SEQ ID NO 59
<211> LENGTH: 86
<212> TYPE: DNA
<213> ORGANISM: Artificial sequence
<220> FEATURE:
<223> OTHER INFORMATION: Template oligo used in examples 15 to 20

<400> SEQUENCE: 59
cgacctacga gctgtccaga agtaacaggt cgatccgcgt taccagtctt gcctgaacgt    60
agtcgtctgg tcacgtggat ccttga                                        86

<210> SEQ ID NO 60
<211> LENGTH: 81
<212> TYPE: DNA
<213> ORGANISM: Artificial sequence
<220> FEATURE:
<223> OTHER INFORMATION: Template oligo used in examples 15 to 20

<400> SEQUENCE: 60
agctggatgc tcgacaggtc gaggtcgatc cgcgttacca gtcttgcctg aacgtagtcg    60
tccgatgcaa tccagaggtc g                                             81

<210> SEQ ID NO 61
<211> LENGTH: 85
<212> TYPE: DNA
<213> ORGANISM: Artificial sequence
<220> FEATURE:
<223> OTHER INFORMATION: Template oligo used in examples 15 to 20

<400> SEQUENCE: 61
cgacctacga gctgtccaga agtaactttt tttttttttt tttttttttt tttttttttt    60
tttttctggt cacgtggatc cttga                                         85
```